United States Patent
Robinson et al.

(10) Patent No.: US 12,041,850 B2
(45) Date of Patent: Jul. 16, 2024

(54) LUMINESCENT COMPOUNDS

(71) Applicant: CHROMATWIST LIMITED, Wolverhampton (GB)

(72) Inventors: Alex Robinson, Wolverhampton (GB); Jon Preece, Wolverhampton (GB); Gregory O'Callaghan, Wolverhampton (GB); Karolis Virzbickas, Wolverhampton (GB); Owen Jones, Wolverhampton (GB); Dennis Zhao, Wolverhampton (GB); Michael Butlin, Wolverhampton (GB); Sareena Sund, Wolverhampton (GB)

(73) Assignee: CHROMATWIST LIMITED, Wolverhampton (GB)

( * ) Notice: Subject to any disclaimer, the term of this patent is extended or adjusted under 35 U.S.C. 154(b) by 933 days.

(21) Appl. No.: 16/982,889

(22) PCT Filed: Mar. 21, 2019

(86) PCT No.: PCT/GB2019/050809
§ 371 (c)(1),
(2) Date: Sep. 21, 2020

(87) PCT Pub. No.: WO2019/180445
PCT Pub. Date: Sep. 26, 2019

(65) Prior Publication Data
US 2021/0005824 A1    Jan. 7, 2021

(30) Foreign Application Priority Data
Mar. 21, 2018    (GB) .................................... 1804511

(51) Int. Cl.
*C07D 263/52*    (2006.01)
*C07D 409/04*    (2006.01)
(Continued)

(52) U.S. Cl.
CPC ......... *H10K 85/657* (2023.02); *C07D 263/52* (2013.01); *C07D 409/04* (2013.01);
(Continued)

(58) Field of Classification Search
CPC .. H10K 85/657; H10K 85/615; H10K 85/655; H10K 85/6574; H10K 50/125;
(Continued)

(56) References Cited

U.S. PATENT DOCUMENTS

| 2002/0070662 A1 | 6/2002 | Moriyama et al. |
| 2003/0171412 A1 | 9/2003 | Malamas et al. |

(Continued)

FOREIGN PATENT DOCUMENTS

| CN | 101967147 | 2/2011 |
| CN | 105503897 | 4/2016 |

(Continued)

OTHER PUBLICATIONS

Jan Najbar et al., "External Heavy Atom Effect on Decay of The Triplet State of Aromatic Hydrocarbons. II. The Decay Functions of Phosphorescence Andof ESR Signals of Triphenylene in The Presence of Iodide Ions," Journal of Luminescence, vol. 11, Issues 3-4, Dec. 1975-Feb. 1976, pp. 215-226.

(Continued)

*Primary Examiner* — Taylor V Oh
(74) *Attorney, Agent, or Firm* — Nixon & Vanderhye PC

(57) ABSTRACT

Polycyclic aromatic hydrocarbon derivatives represented by the following general formula: (I) wherein R independently represents an aromatic group and/or an aliphatic group; Q is one of a cyclic aliphatic hydrocarbon, a cyclic aromatic hydrocarbon, a polycyclic hydrocarbon, a polycyclic aromatic hydrocarbon, and/or a fused polycyclic aromatic hydrocarbon; wherein the substituents independently com- (Continued)

prise one or more of a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group; p is an integer of 1 to 2; q is an integer of 1 to 4; $Y^1$ and $Y^2$ independently represent one or more of a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group; and x is an integer of 0, 1, 2, 3, 4, 5, 6, 7, 8, 9, 10 or more.

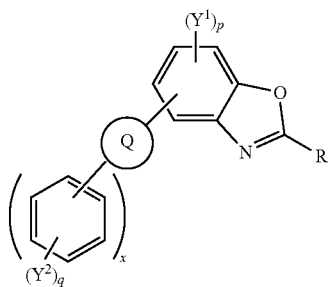

10 Claims, 20 Drawing Sheets

(51) Int. Cl.
  *C09K 11/06* (2006.01)
  *H10K 85/60* (2023.01)
  *H10K 50/125* (2023.01)

(52) U.S. Cl.
  CPC ............ *C09K 11/06* (2013.01); *H10K 85/615* (2023.02); *H10K 85/655* (2023.02); *H10K 85/6574* (2023.02); *C09K 2211/1018* (2013.01); *H10K 50/125* (2023.02)

(58) Field of Classification Search
  CPC .... H10K 50/11; C07D 263/52; C07D 409/04; C07D 413/04; C09K 11/06; C09K 2211/1018; C07C 2603/42; C07C 217/94; Y02E 10/549
  USPC ........................................................ 548/223
  See application file for complete search history.

(56) References Cited

U.S. PATENT DOCUMENTS

| 2014/0047976 A1 | 2/2014 | Yeong et al. |
| 2016/0322569 A1 | 11/2016 | Yen |
| 2018/0040829 A1 | 2/2018 | Lee et al. |

FOREIGN PATENT DOCUMENTS

| CN | 105713003 | 6/2016 |
| CN | 104672226 | 12/2017 |
| CN | 107573328 | 1/2018 |
| EP | 0 847 228 | 6/1998 |
| JP | 2013-071922 | 4/2013 |
| WO | 95/25710 | 9/1995 |

OTHER PUBLICATIONS

Exam Report issued on Jun. 15, 2022 in corresponding European Application 19714752.3, 8 pages.
May 27, 2023 Office Action issued in Chinese Patent Application No. 201980033490.6, pp. 1-13.
Maksim V. Sednev et al., "Fluorescent dyes with large Stokes shifts for super-resolution optical microscopy of biological objects: a review," Methods and Applications in Fluorescence 3, Oct. 22, 2015, Apr. 20, 2004, 29 pages.
Jack W. Levell et al., "Fluorescence Enhancement by Symmetry Breaking in a Twisted Triphenylene Derivative," J. Phys. Chem. A, Oct. 1, 2010, 114, pp. 13291-13295.
Minrong Zhu et al., "Blue fluorescent emitters: design tactics and applications in organic light-emitting diodes," Chem. Soc. Rev. Jun. 21, 2013, 42(12), pp. 4963-4976.
Neville Boden et al., "Novel Discotic Liquid Crystals created by Electrophilic Aromatic Substitution," J. Mater. Chem., 1995, 5(12), pp. 2275-2281.
James A. Jordan-Hore et al., "Oxidative Pd(II)-Catalyzed C-H Bond Amination to Carbazole at Ambient Temperature" JACS Communications, Aug. 11, 2008, J. Am. Chem. Soc. 2008, 130, pp. 16184-16186.
Judith E. Berlier et al., "Quantitative Comparison of Long-wavelength Alexa Fluor Dyes to Cy Dyes: Fluorescence of the Dyes and Their Bioconjugates," The Journal of Histochemistry & Cytochemistry, vol. 51(12) 2003, pp. 1699-1712.
Richard C. Powell, "Singlet Exciton Energy Transfer in Organic Solids," Journal of Luminescence vol. 11, Sep.-Nov. 1975, pp. 1-45.
International Search Report for PCT/GB2019/050809, mailed Jul. 15, 2019, 17 pages.
Search Report for GB1804511.2, dated Nov. 6, 2018, 5 pages.
Kumar et al., "Novel triphenylenoimidazole discotic liquid crystals", Tetrahedron Letters, vol. 52, No. 41, Aug. 7, 2011, pp. 5363-5367.
PubChem Compound, Dec. 24, 2015, XP002791093.
PubChem Compound, Dec. 24, 2015, XP002791093, 4 pages.

Compound1

| Compound Structure | Compound Number |
|---|---|
| 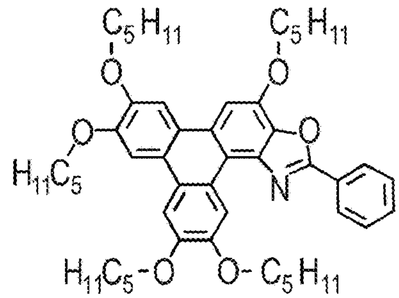 | 2 |
| 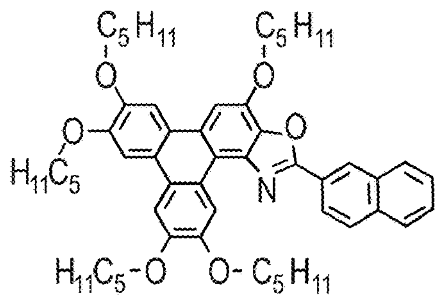 | 3 |
| 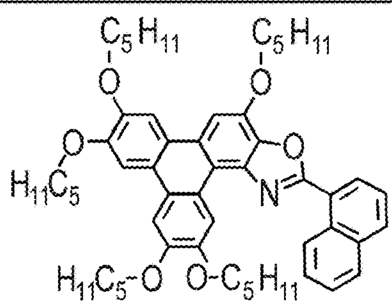 | 4 |
| 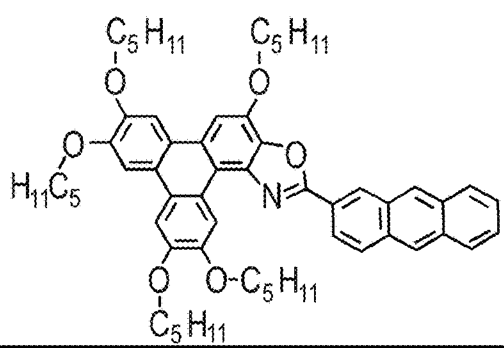 | 5 |
| 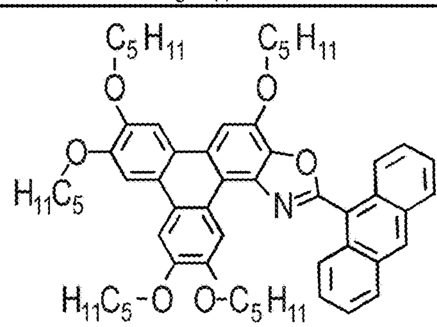 | 6 |

| Compound Structure | Compound Number |
|---|---|
| (structure) | 7 |
| (structure) | 8 |
| (structure) | 9 |
| (structure) | 10 |
| (structure) | 11 |

Fig. 7B

| | |
|---|---|
|  | 24 |
|  | 25 |
|  | 26 |
|  | 27 |
| wherein R=$C_5H_{11}$ in four cases and H in one case  | 28 |
|  | 29 |

| Structure | # |
|---|---|
| (structure with C5H11-O groups, phenyl, oxazole, OH) | 30 |
| (structure with HO, OH groups and methyl oxazole) | 31 |
| (structure with H3COC2H4OC2H4OC2H4O- groups, OC5H11, methyl oxazole) | 32 |
| (structure with MeO, OMe, H11C5-O, O-C5H11 groups, butyl oxazole) | 33 |
| (structure with MeO, OMe, H11C5-O, O-C5H11 groups, phenyl oxazole) | 34 |
| (structure with MeO, OMe, H11C5-O, O-C5H11 groups, 4-cyanophenyl oxazole) | 35 |

Fig. 7F

LUMINESCENT COMPOUNDS

This application is the U.S. national phase of International Application No. PCT/GB2019/050809 filed 21 Mar. 2019, which designated the U.S. and claims priority to GB Patent Application No. 1804511.2 filed 21 Mar. 2018, the entire contents of each of which are hereby incorporated by reference.

This invention relates generally to organic luminescent compounds. More specifically, although not exclusively, this invention relates to novel luminescent polycyclic aromatic hydrocarbon, e.g. triphenylene, derivatives, methods of synthesising the same, uses of the same, and devices comprising the same.

Luminescent compounds are widely used in industrial and research applications as, for example, dyes, probes, sensors, and in electronic devices. These molecules emit light under external energy excitation from sources such as light and/or electrical current.

In photoluminescence, under light irradiation a luminescent compound will absorb light of a specific wavelength and re-emit light of a different wavelength. The type of photoemission observed depends on the molecular structure of the compound.

The difference between the maximum excitation wavelength and the emission wavelength of a luminescent compound is known as the Stokes shift. For use as dyes, probes and/or sensors in industrial applications, it is advantageous for luminescent compounds to possess a large Stokes shift, often defined as greater than 8000 cm$^{-1}$ i.e. a comparatively large difference between the excitation wavelength and emission wavelength. This is advantageous because it minimises the reabsorption of light from the emission of the molecule.

A drawback of many fluorescent dyes with large Stokes shifts is their relatively low brightness, this being defined as the product of the molar extinction coefficient and fluorescence quantum yield. Additionally, dyes with large Stokes shifts often suffer from poor photostability (Methods Appl. Fluoresc. 3 (2015) 042004).

Organometallic complexes that are luminescent often have a large Stokes shift. However, these contain metal centres, e.g. osmium, ruthenium, iridium, rhenium and so on, which are rare, expensive, the complexes are often difficult to synthesise and often toxic. Luminescent organic molecules are often easier to synthesise, but usually exhibit a Stokes shift of relatively smaller magnitude.

In contrast, in electroluminescence, a luminescent compound will emit light in response to an electric current. One of the main applications for this phenomenon is in electronic devices containing OLEDs (Organic Light Emitting Diodes). The OLED material is a layer of a luminescent organic compound, which is situated between two electrodes, one of which is typically transparent. This technology is used in digital displays in electronic devices such as televisions screens, computer monitors, mobile phones, electroluminescent lighting panels and so on.

It is advantageous for luminescent compounds for use in electroluminescent applications to exhibit high brightness. Brightness is defined as the product of the molar extinction coefficient (E) and fluorescence quantum yield ($\phi$) divided by 1000. Consequently, it is advantageous for luminescent compounds to exhibit a high molar extinction coefficient (E) (defined by the Beer-Lambert law, in which A is absorbance, c is the molar concentration of the luminescent compound, and I is the path length), and also a high quantum yield ($\phi$) as a measure of efficiency.

It is well known that polycyclic aromatic hydrocarbons exhibit luminescent properties. One such class of compound is triphenylene and its derivatives. For example, triphenylene may be functionalised with alkoxy chains appended to the periphery of the molecule. In addition, these derivatives exhibit discotic liquid crystalline (DLC) behaviour (J. Nabar and A. Chodkowska, J. Luminescence, 1975, 11, 215). Discotic liquid crystalline behaviour is characterised in that disc-shaped molecules form stacks or columns in a mesophase, which allows charge transfer through π stacking, enabling the material to be electrically semi-conductive in the stacking direction. This DLC behaviour, combined with the luminescent properties, is particularly useful for application in technologies such as electronic devices using OLEDs (Organic Light Emitting Diodes), LEDs (Light Emitting Diodes), and for use in solar cells.

It is also known for luminescent compounds to exhibit photoconductivity, in which compounds exhibit increased electrical conductivity in the presence of light by converting the light energy into current. It is known to utilise compounds with good photoconductivity in devices such as solar cells.

Although many luminescent triphenylene derivatives have been synthesised and characterised (Levell et. al. J. Phys. Chem. A., 2010, 114, 13291, for example), it remains a challenge to provide triphenylene derivatives with the advantageous properties described above, i.e. large Stokes shift, high brightness, high molar extinction coefficient, and high quantum yield. Furthermore, it remains a challenge to provide a range of luminescent compounds that emit wavelengths throughout the visible spectrum. Specifically, blue emitters are a particular challenge to provide (Chem Soc Rev. 2013 Jun. 21; 42(12):4963-76).

Furthermore, it remains a challenge to provide luminescent triphenylene derivatives wherein the absorption and the emission energies can be predicted and tuned by design and synthesis to result in specific and desired visible colours (Methods Appl. Fluoresc. 3 (2015) 042004).

Accordingly, a first aspect of the invention provides polycyclic aromatic hydrocarbon derivatives represented by the following general formula:

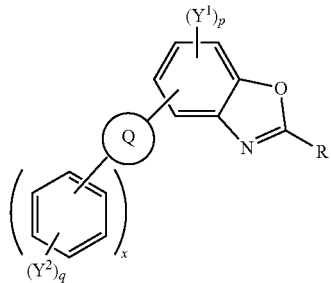

wherein R independently represents an aromatic group and/or an aliphatic group;

Q is one of a cyclic aliphatic hydrocarbon, a cyclic aromatic hydrocarbon, a polycyclic hydrocarbon, a polycyclic aromatic hydrocarbon, and/or a fused polycyclic aromatic hydrocarbon; wherein the substituents independently comprise one or more of a hydrogen atom, a deuterium atom, a fluorine atom, a chlorine atom, a bromine atom, a carbon atom, an oxygen atom (e.g. an alkylated oxygen atom), a nitrogen atom (e.g.

an alkylated nitrogen atom), a cyano group, a nitro group, an alkyl group and/or an aryl group;

p is an integer of 1 to 2;

q is an integer of 1 to 4;

$Y^1$ and $Y^2$ independently represent one or more of a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group;

and x is an integer of 0, 1, 2, 3, 4, 5, 6, 7, 8, 9, 10 or more.

In embodiments, Q may represent $C_6H_4$. In embodiments, Q is a polycyclic aromatic hydrocarbon, for example, Q may be one of naphthalene, anthracene, phenanthrene, tetracene, chrysene, triphenylene, pyrene, pentacene, benzo[a]pyrene, corannulene, benzo[ghi]perylene, coronene, ovalene, fullerene, and/or benzo[c]fluorene. Q may be any isomer of the polycyclic aromatic hydrocarbons described, for example, 1-napthalene, 2-napthalene, 2-anthracene, 9-anthracene. The polycyclic aromatic hydrocarbon group may be substituted with other moieties such as aryl groups, alkyl groups, heteroatoms, and/or other electron withdrawing or electron donating groups.

Q is bonded to other six membered rings, e.g. aromatic six membered rings, and/or substituted aromatic six membered rings. The number of six membered rings bonded to Q is represented by the integer x wherein x is 0, 1, 2, 3, 4, 5, 6, 7, 8, 9, 10 or more.

In an embodiment, Q is an aromatic six-membered ring, and x an integer of 2 or above, e.g. 2, 3, 4, 5 or above 5.

In embodiments, the polycyclic aromatic hydrocarbon, e.g. triphenylene, derivatives may be represented by the following general formula:

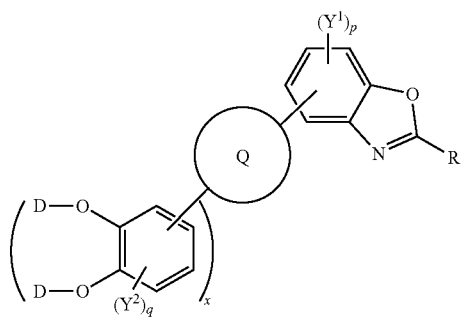

wherein D is a hydrogen atom, a deuterium atom, a silicon atom, or a carbon atom;

p is an integer of 1 to 2;

q is an integer of 1 to 2;

$Y^1$ and $Y^2$ independently represent one or more of a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group;

and x is an integer of 0, 1, 2, 3, 4, 5, 6, 7, 8, 9, 10 or more.

For example, D may be a linear or branched alkyl chain, an aryl group, or a combination thereof.

The polycyclic aromatic hydrocarbon, e.g. the triphenylene, derivatives may be represented by the following general formula:

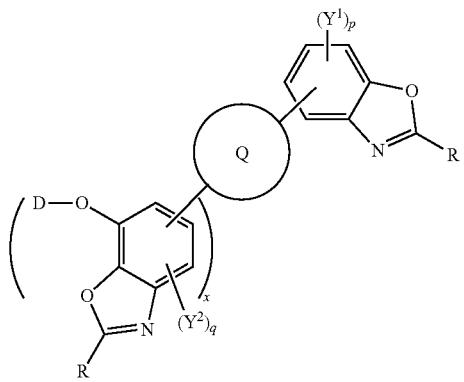

wherein D is a hydrogen atom, a deuterium atom, a silicon atom, or a carbon atom p is an integer of 1 to 2;

q is an integer of 1;

$Y^1$ and $Y^2$ independently represent one or more of a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group;

and x is an integer of 0, 1, 2, 3, 4, 5, 6, 7, 8, 9, 10 or more.

For example, D may be a linear or branched alkyl chain, an aryl group, or a combination thereof.

A further aspect of the invention provides polycyclic aromatic hydrocarbon derivatives, represented by the following general formula:

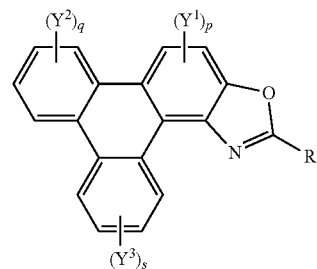

wherein R independently represents an aromatic group and/or an aliphatic group;

p is an integer of 1 to 2;

q and s are independently integers of 1 to 4;

$Y^1$, $Y^2$, and $Y^3$ independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group (e.g. a phenol group).

In embodiments, the polycyclic aromatic hydrocarbon derivative may be a triphenylene derivative. In alternative embodiments, the polycyclic aromatic hydrocarbon derivative may comprise a fused polycyclic aromatic hydrocarbon comprising six 6-membered rings.

$Y^1$, $Y^2$, and $Y^3$ may comprise a carboxylic acid group, a glycol, an alkoxy, a thioalkoxy, an amino, an acetate, an amide, a thioamide, a thioester, an azo, and/or a silyl group. Additionally or alternatively, $Y^1$, $Y^2$, and $Y^3$ may comprise an alkyl group. The alkyl group(s) may be a straight chain, or may comprise a branched chain, and/or may be further functionalised. Additionally or alternatively, $Y^1$, $Y^2$, and $Y^3$ may comprise an aryl group. The aryl group(s) may be unsubstituted or may be further functionalised.

The integer p may be 1 to 2. The integer q may be 1, 2, 3, or 4. The integer s may be 1, 2, 3, or 4.

A yet further aspect of the invention provides polycyclic aromatic hydrocarbon derivatives, represented by the following general formula:

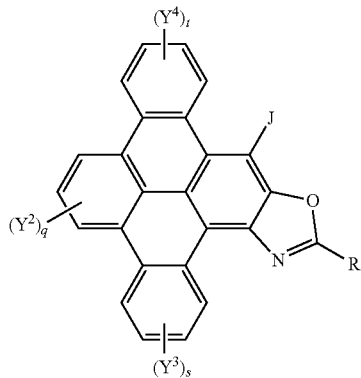

wherein R independently represents an aromatic group and/or an aliphatic group;
q is independently an integer of 1 to 3;
s is independently an integer of 1 to 4;
t is independently an integer of 1 to 4;
$Y^2$, $Y^3$, and $Y^4$ and J independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group (e.g. a phenol group).

In embodiments, the polycyclic aromatic hydrocarbon derivatives are triphenylene derivatives, represented by the following general formula:

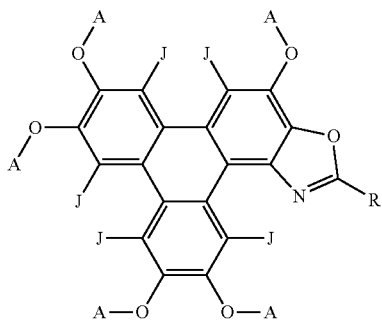

wherein R independently represents an aromatic group and/or an aliphatic group;
A independently represents a hydrogen atom, an aryl group, an alkyl group comprising 1 to 20 carbons (e.g. 1 to 15 carbons, or 1 to 10 carbons, or 10, 9, 8, 7, 6, 5, 4, 3, 2 or 1 carbons) or an alkyl ether;
J independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group (e.g. a phenol group).

In embodiments, A may be $C_5H_{11}$ and/or $C_4H_9$. In embodiments, A represents a polyethylene glycol (PEG) group (e.g. $C_2H_4OC_2H_4OC_2H_4OCH_3$.

In embodiments, the triphenylene derivative may not be the compound wherein A is $C_5H_{11}$, J is H and R is $C_4H_9$.

In embodiments, the polycyclic aromatic hydrocarbons are represented by the following general formula:

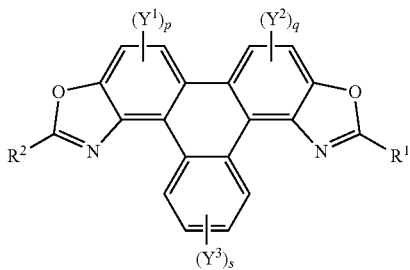

wherein $R^1$ and $R^2$ independently represents an aromatic group and/or an aliphatic group;
p and q are independently an integer of 1 to 2;
s is an integer of 1 to 4;
$Y^1$, $Y^2$, and $Y^3$ independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group.

In embodiments, the polycyclic aromatic hydrocarbons are triphenylene derivatives represented by the following general formula:

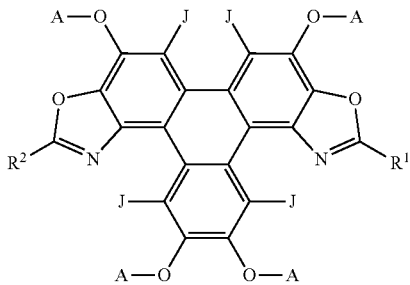

wherein $R^1$ and $R^2$ independently represents an aromatic group and/or an aliphatic group;
A independently represents a hydrogen atom, an aryl group, an alkyl group comprising 1 to 20 carbons (e.g. 1 to 15 carbons, or 1 to 10 carbons, or 10, 9, 8, 7, 6, 5, 4, 3, 2 or 1 carbons) or an alkyl ether;
J independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group.

In embodiments, A may be $C_5H_{11}$ and/or $C_4H_9$. In embodiments, A represents a polyethylene glycol (PEG) group (e.g. $C_2H_4OC_2H_4OC_2H_4OCH_3$.

In embodiments, the polycyclic aromatic hydrocarbons are represented by the following general formula:

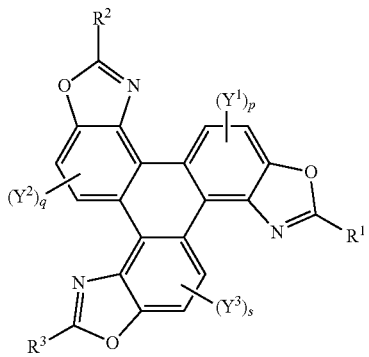

wherein $R^1$, $R^2$, $R^3$ independently represent an aromatic group and/or an aliphatic group;

p, q, and s are each independently an integer of 1 to 2;

$Y^1$, $Y^2$, and $Y^3$ independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group.

In embodiments, the polycyclic aromatic hydrocarbons are triphenylene derivatives represented by the following general formula:

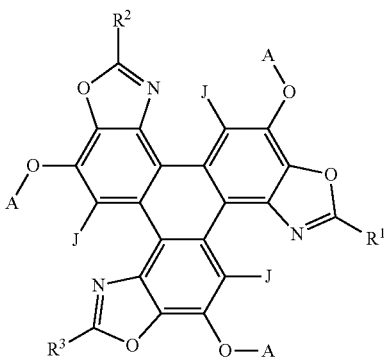

wherein $R^1$, $R^2$, $R^3$ independently represent an aromatic group and/or an aliphatic group;

A independently represents a hydrogen atom, an aryl group, an alkyl group comprising 1 to 20 carbons (e.g. 1 to 15 carbons, or 1 to 10 carbons, or 10, 9, 8, 7, 6, 5, 4, 3, 2 or 1 carbons) or an alkyl ether;

J independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group.

In embodiments, A comprises further functionality, for example, A may further comprise fluorine atoms, chlorine atoms, cyano groups, nitro groups, glycol, alkoxy, thioalkoxy, polyethylene glycol, amino, acetate, carboxylic acid, amide, thioamide, thioester, azo, and/or silyl groups.

In embodiments, J comprises or represents an aryl group, e.g. a phenol group. Additionally or alternatively, J comprises a halogen atom, e.g. fluorine, chlorine, bromine, or iodine.

In embodiments, R, $R^1$, $R^2$, or $R^3$ may be an alkyl group, for example, a straight or branched alkyl chain. In embodiments, at least one of R, $R^1$, $R^2$, $R^3$ may be a methyl, ethyl, propyl, butyl group.

In embodiments wherein R, $R^1$, $R^2$, or $R^3$ is an aromatic group, the aromatic group may be one of, or a combination of, an aromatic hydrocarbon group, and/or an aromatic heterocyclic group.

In embodiments wherein R, $R^1$, $R^2$, or $R^3$ is an aromatic hydrocarbon group, the aromatic hydrocarbon group may comprise one of, or a combination of, a phenyl ring and/or a substituted phenyl ring. There may be one, two, three, four, or five additional substituents on the phenyl ring. The substituents are bonded directly to the phenyl ring, and may be one of, or a combination of, fluorine, chlorine, bromine, iodine, a hydroxyl group, an amine group, a nitro group, an alkoxy group, a carboxylic acid, an amide, a cyano group, a trifluoromethyl, an ester, an alkene an alkyne, an azide, an azo, an isocyanate, a ketone, an aldehyde, an alkyl group consisting of a hydrocarbon chain, or a hydrocarbon ring, an alkyl group consisting of other heteroatoms such as fluorine, chlorine, bromine, iodine, oxygen, nitrogen, and/or sulphur. The alkyl group may comprise a hydroxyl group, an amine group, a nitro group, an ether group, a carboxylic acid, an amide, a cyano group, trifluoromethyl, an ester, an alkene an alkyne, an azide, an azo, an isocyanate, a ketone, an aldehyde, for example. The substituents may be another aromatic group, for example, R may comprise a phenyl substituted with a further phenyl ring. In embodiments, the R group may be a phenyl ring, substituted with a second phenyl ring, which in turn is substituted with a third phenyl ring.

In embodiments wherein R, $R^1$, $R^2$, or $R^3$ is an aromatic group, the aromatic group may be a polycyclic aromatic hydrocarbon, for example, naphthalene, anthracene, phenanthrene, tetracene, chrysene, triphenylene, pyrene, pentacene, benzo[a]pyrene, corannulene, benzo[ghi]perylene, coronene, ovalene, fullerene, and/or benzo[c]fluorene. The R group may be bonded to the triphenylene derivative by any isomer of the polycyclic aromatic hydrocarbons described, for example, 1-napthalene, 2-napthalene, 2-anthracene, 9-anthracene. The polycyclic aromatic hydrocarbon group may be substituted with other moieties such as aryl groups, alkyl groups, heteroatoms, and/or other electron withdrawing or electron donating groups.

In embodiments wherein R, $R^1$, $R^2$, or $R^3$ is an aromatic heterocyclic group, the heterocyclic group may be a three membered ring, a four membered ring, a five membered ring, a six membered ring, a seven membered ring, an eight membered ring, a nine membered ring, a ten membered ring, or a fused ring. In embodiments, the heterocyclic group may be furan, benzofuran, isobenzofuran, pyrrole, indole, isoindole, thiophene, benzothiophene, benzo[c]thiophene, imidazole, benzimidazole, purine, pyrazole, indazole, oxazole, benzoxazole, isoxazole, benzisoxazole, thiazole, benzothiazole, pyridine, quinoline, isoquinoline, pyrazine, quinoxaline, acridine, pyrimidine, quinozoline, pyridazine, cinnoline, phthalazine, 1,2,3-triazine, 1,2,4-triazine, 1,3,5-triazine.pyridine or thiophene.

In embodiments wherein R, $R^1$, $R^2$, or $R^3$ is an aliphatic group, the aliphatic group may be one of, or a combination of, an n-alkyl chain, a branched alkyl chain, an alkyl chain comprising unsaturated moieties, an alkyl chain comprising heteroatoms, for example, fluorine, chlorine, bromine, iodine, oxygen, sulphur, nitrogen. The alkyl chain may comprise unsaturated portions, comprising alkenes, or aromatic moieties. The alkyl chain may comprise functional groups for further derivatisation of the polycyclic aromatic hydrocarbon, e.g. triphenylene, derivative. For example, the functional groups may be one or more of an azide, a carbonyl group, an alcohol, a halogen, or an alkene.

In embodiments, In embodiments wherein R, $R^1$, $R^2$, or $R^3$ comprise a crown ether.

The polycyclic aromatic hydrocarbon, e.g. triphenylene, derivatives may be used, for example, as luminescent dyes for use in devices.

A further aspect of the invention provides a device comprising the polycyclic aromatic hydrocarbon derivatives, e.g. the triphenylene derivatives. The device may be an electronic device, for example, an organic electroluminescent device, a thin-film transistor and/or an OPV (organic photovoltaic) device. The electronic device may comprise a digital display, the digital display comprising the polycyclic aromatic hydrocarbon derivatives, e.g. the triphenylene derivatives, of the present invention, for example, a liquid crystal display. The digital display may be in a television screen, a computer monitor, a mobile phone screen, a games console, for example. The organic electroluminescent device may comprise a pair of electrodes and one or more layers interposed therebetween, wherein the one or more layers comprise one or more of the polycyclic aromatic hydrocarbon derivatives, e.g. the triphenylene derivatives.

The device may be for the use of detecting species, for example, ions, e.g. metal ions. For example, the polycyclic aromatic hydrocarbon derivative, e.g. the triphenylene derivative, may comprise a moiety that is capable of binding to a species, e.g. an ion. The moiety may be tagged to or integrated into, i.e. covalently bonded to, the polycyclic aromatic hydrocarbon derivatives, e.g. the triphenylene derivative. Binding of a species to a polycyclic aromatic hydrocarbon derivative, e.g. a triphenylene derivative, may elicit a luminescent response. The luminescent response may be recorded to quantitatively or qualitatively measure the presence of the species, e.g. in solution. The moiety may be one or more of a crown ether, a multidentate ligand, a bidentate ligand or a monodentate ligand. The moiety may be the R group of the polycyclic aromatic hydrocarbon, e.g. triphenylene, derivatives. The polycyclic aromatic hydrocarbon, e.g. triphenylene, derivative, e.g. comprising a moiety that is capable of binding to a species, e.g. metal ions. The triphenylene derivatives may be spin coated onto a dipstick. The dipstick may comprise a UV LED (light emitting diode). The LED may be illuminated in the presence of specific species upon binding to the polycyclic aromatic hydrocarbon derivatives, e.g. the triphenylene derivative, e.g. ions, metal ions. The LED illumination may be specific to a specific species that is bound to the polycyclic aromatic hydrocarbon derivatives, e.g. the triphenylene derivative, i.e. a specific wavelength of light, wavelength A, is emitted by the LED upon binding to a specific species, species A, and a different wavelength of light, wavelength B, is emitted by the LED upon binding to a specific species, species B.

The device may be used in biofluorescent microscopy techniques. The device may comprise the polycyclic aromatic hydrocarbon derivatives, e.g. the triphenylene derivatives, as a luminescent dye that may be used to label or tag biological, or non-biological samples, which may include DNA or proteins or antigens or biomarkers.

The device may comprise a polymer, or a pre-polymer, and/or a resin composition for use in printing, for example, for use in 3D printing plastic products comprising the polycyclic aromatic hydrocarbon derivatives, e.g. the triphenylene derivatives. The polycyclic aromatic hydrocarbon, e.g. triphenylene, derivatives may be used as a dopant in the device.

The polycyclic aromatic hydrocarbon derivatives, e.g. the triphenylene derivative(s), of the device may emit light in the visible spectrum, i.e. between 380 nm and 750 nm. The polycyclic aromatic hydrocarbon derivatives, e.g. the triphenylene derivative(s), of the device may exhibit a Stokes shift of between 8000 $cm^{-1}$ to 25,000 $cm^{-1}$, for example, between 15,000 $cm^{-1}$ to 25,000 $cm^{-1}$. The polycyclic aromatic hydrocarbon derivatives, e.g. the triphenylene derivative(s), of the device may exhibit a conductivity value of $5.0\times10^{-13}$ S $cm^{-1}$, and $1.5\times10^{-11}$ S $cm^{-1}$, for example, between $6\times10^{-12}$ S $cm^{-1}$ and $1.5\times10^{-11}$ S $cm^{-1}$.

The polycyclic aromatic hydrocarbon derivative, e.g. the triphenylene derivative(s), of the device may) exhibit a photoconductivity when irradiated at 350 nm of between $1.5\times10^{-10}$ S $cm^{-1}$ and $1\times10^{-3}$ S $cm^{-1}$, for example, between $1\times10^{-8}$ S cm−1 and $1\times10^{-3}$ cm−1.

A yet further aspect of the invention provides a compound for the fabrication of the triphenylene derivatives comprising the structure:

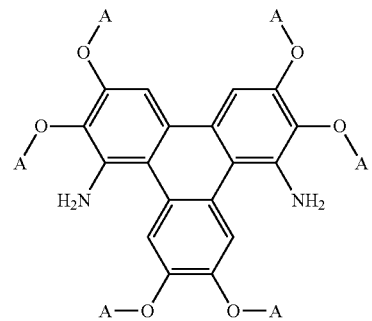

wherein A independently represents a hydrogen atom, an aryl group, an alkyl group comprising 1 to 20 carbons (e.g. 1 to 15 carbons, or 1 to 10 carbons, or 10, 9, 8, 7, 6, 5, 4, 3, 2 or 1 carbons) or an alkyl ether.

Preferably, in this embodiment A represents an alkyl chain, for example, comprising between 1 to 10 carbon atoms, e.g. 1, 2, 3, 4, 5, 6, 7, 8, 9, or 10 carbon atoms, e.g. A is $C_5H_{11}$.

A yet further aspect of the invention provides a method of synthesising polycyclic aromatic hydrocarbon derivatives (P1) comprising the general formula:

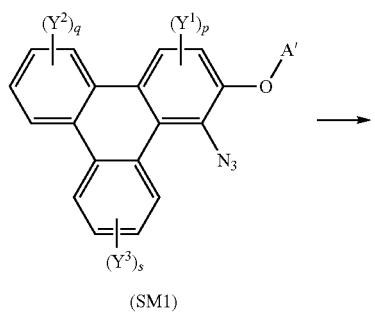

(SM1)

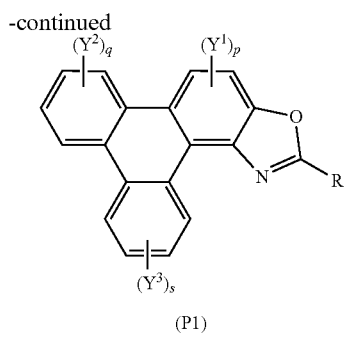

(P1)

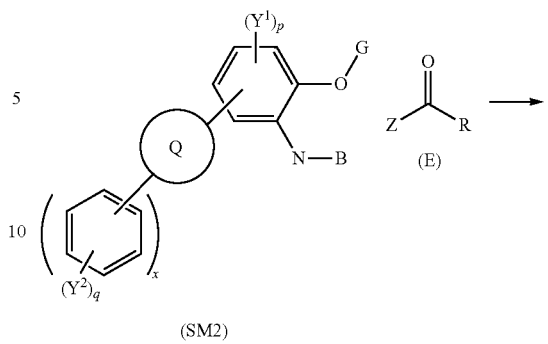

(SM2)

(P2)

wherein R represents an aliphatic group;
A' represents an alkyl chain comprising between 3 to 20 carbons;
p is an integer of 1 to 2;
q and s are independently integers of 1 to 4;
$Y^1$, $Y^2$, and $Y^3$ independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group (e.g. a phenol group).

In this embodiment, (SM1) represents the polycyclic aromatic hydrocarbon core and (P1) represents a triphenylene derivative. In this embodiment, A' represents an alkyl chain comprising between 3 to 20 carbons, e.g. 4, 5, 6, 7, 8, 9, 10, 11, 12, 13, 14, 15, 16, 17, 18, 19, or 20 carbons. In this embodiment, R represents an alkyl chain with one fewer carbon atoms to that of A'. For example, preferably, A' comprises a linear alkyl chain comprising five carbons, i.e. $C_5H_{11}$ and R comprises a linear alkyl chain comprising four carbons, i.e. $C_4H_9$. The method may involve the polycyclic aromatic hydrocarbon, e.g. triphenylene, core (SM1) undergoing an intramolecular rearrangement to produce polycyclic aromatic hydrocarbon, e.g. triphenylene, derivative (P1).

The method may comprise the use of a solvent, for example, an inert solvent. The method may comprise heating the polycyclic aromatic core (SM1) under pressure to produce the polycyclic aromatic hydrocarbon derivative (P1).

In embodiments, the method may comprise a catalyst, for example, a transition metal catalyst. The transition metal catalyst may be a rhodium catalyst, e.g. $[[CH_3(CH_2)_6CO_2]_2Rh]_2$. The method may comprise heating to reflux in the presence of a transition metal catalyst, for example, a rhodium catalyst, e.g. $[[CH_3(CH_2)_6CO_2]_2Rh]_2$ using toluene as the solvent.

A yet further aspect of the invention provides a method of synthesising polycyclic aromatic hydrocarbon derivatives (P2), the method comprising the general formula:

wherein (SM2) represents the polycyclic aromatic hydrocarbon core, (P2) represents the polycyclic aromatic hydrocarbon derivative;
Q is one of a substituted or unsubstituted cyclic aliphatic hydrocarbon, a substituted or unsubstituted cyclic aromatic hydrocarbon, a substituted or unsubstituted polycyclic hydrocarbon, a substituted or unsubstituted polycyclic aromatic hydrocarbon, and/or a substituted or unsubstituted fused polycyclic aromatic hydrocarbon; wherein the substituents comprise one or more of a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group;
p is an integer of 1 to 2;
q is an integer of 1 to 4;
$Y^1$ and $Y^2$ independently represent one or more of a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group;
and x is an integer of 0, 1, 2, 3, 4, 5, 6, 7, 8, 9, 10 or more;
G is a carbon atom;
N is a nitrogen atom;
B is one or more hydrogen atoms; and
wherein (E) represents the reagent;
R independently represents an aromatic group and/or an aliphatic group;
Z is one of an oxygen atom, a derivatised oxygen atom, a chlorine atom, or a bromine atom, or any good leaving group.

In embodiments, the nitrogen atom may be an amine ($NH_2$) wherein B comprises two hydrogen atoms.

In embodiments, the method of synthesising polycyclic aromatic hydrocarbon derivatives (P3) comprises the general formula:

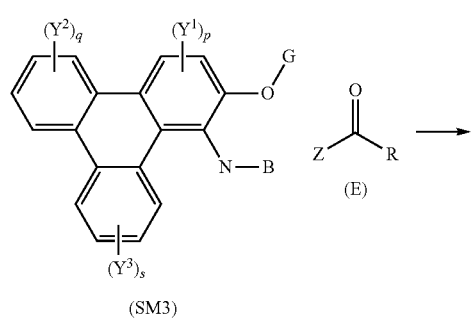

(SM3)

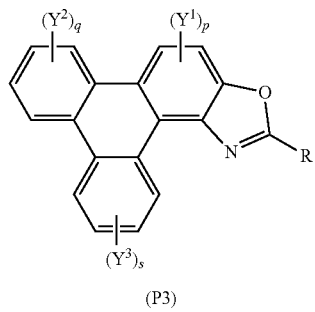

(P3)

wherein (SM3) represents the polycyclic aromatic hydrocarbon core, (P3) represents the polycyclic aromatic hydrocarbon derivative, p is an integer of 1 to 2;

q and s are integers of 1 to 4;

$Y^1$, $Y^2$, and $Y^3$ independently represent one or more of a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group;

G is a carbon atom;

N is a nitrogen atom;

B is one or more hydrogen atoms;

(E) represents the reagent;

R independently represents an aromatic group and/or an aliphatic group;

Z is one of an oxygen atom, a derivatised oxygen atom, a chlorine atom, or a bromine atom, or any good leaving group;

and wherein the polycyclic aromatic hydrocarbon core (SM3) and the reagent (E) undergo an intermolecular coupling reaction to produce the polycyclic aromatic hydrocarbon derivative (P3).

In embodiments, (E) represents the reagent, wherein R is an aromatic group and/or an aliphatic group, and group Z may be one of an oxygen atom or a derivatised oxygen atom, e.g. an OH group; a chlorine atom, or a bromine atom, or any good leaving group. Reagent (E) may be an acyl chloride or a carboxylic acid. The method may involve the polycyclic aromatic hydrocarbon core (SM3) and the reagent (E) undergoing an intermolecular coupling reaction to produce the polycyclic aromatic hydrocarbon derivative (P3).

In embodiments, the method of synthesising polycyclic aromatic hydrocarbon derivatives (P4) comprises the general formula:

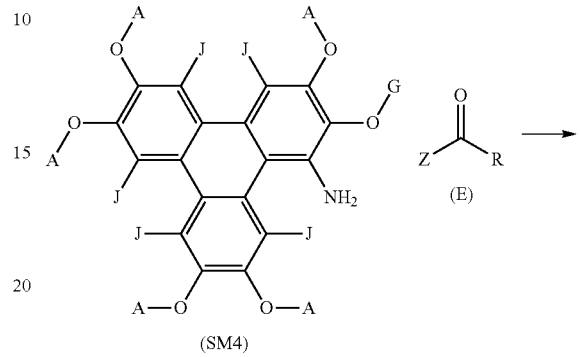

(SM4)

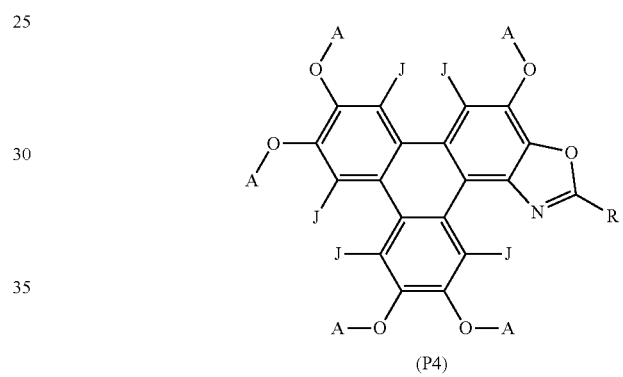

(P4)

wherein (SM4) represents a triphenylene core, (P4) represents a triphenylene derivative;

A independently represents a hydrogen atom, an aryl group, an alkyl group comprising 1 to 20 carbons (e.g. 1 to 15 carbons, or 1 to 10 carbons, or 10, 9, 8, 7, 6, 5, 4, 3, 2 or 1 carbons);

J independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group.

G is a carbon atom;

(E) represents the reagent;

R independently represents an aromatic group and/or an aliphatic group;

Z is one of an oxygen atom, a derivatised oxygen atom, a chlorine atom, or a bromine atom, or any good leaving group;

and wherein the triphenylene core (SM4) and the reagent (E) undergo an intermolecular coupling reaction to produce the triphenylene derivative (P4).

In embodiments, the method of synthesising triphenylene derivatives (100) comprises the general formula:

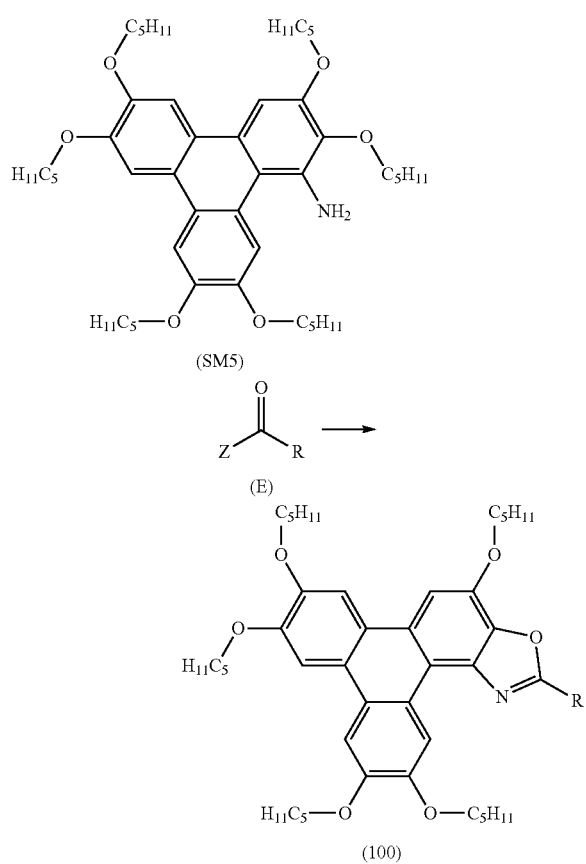

(SM5)

(E)

(100)

wherein R independently represents an aromatic group and/or an aliphatic group.

A yet further aspect of the invention provides a method of synthesising polycyclic aromatic hydrocarbon derivatives (P6), comprising the general formula:

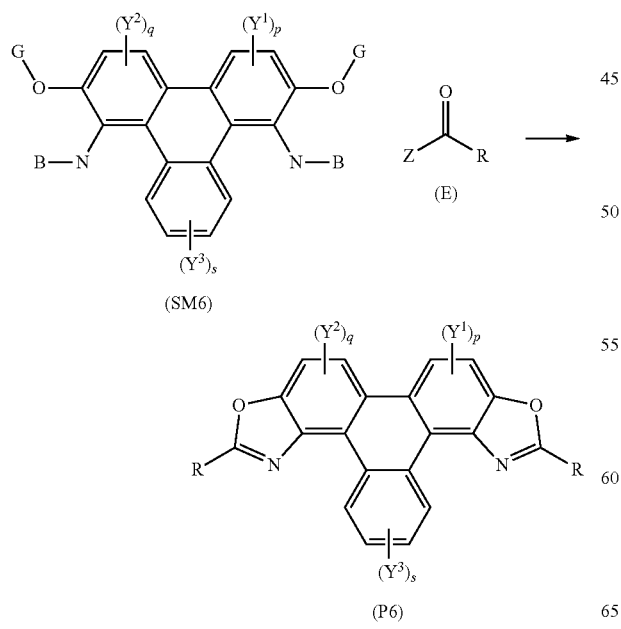

(SM6)

(E)

(P6)

wherein (SM6) represents a polycyclic aromatic hydrocarbon core, (P6) represents a polycyclic aromatic hydrocarbon derivative;

p is an integer of 1 to 2;
q is an integer of 1 to 2;
s is an integer of 1 to 4;
$Y^1$, $Y^2$, and $Y^3$ independently represent one or more of a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group;
G independently represents a substituted carbon atom;
N is a nitrogen atom;
B is one or more hydrogen atoms;
(E) represents the reagent;
R independently represents an aromatic group and/or an aliphatic group;
Z is one of an oxygen atom, a derivatised oxygen atom, a chlorine atom, or a bromine atom, or any good leaving group;
and wherein the polycyclic aromatic hydrocarbon core (SM6) and the reagent (E) undergo an intermolecular coupling reaction to produce the polycyclic aromatic hydrocarbon derivative (P6).

The method of synthesising polycyclic aromatic hydrocarbon derivatives (P7) may comprise the general formula:

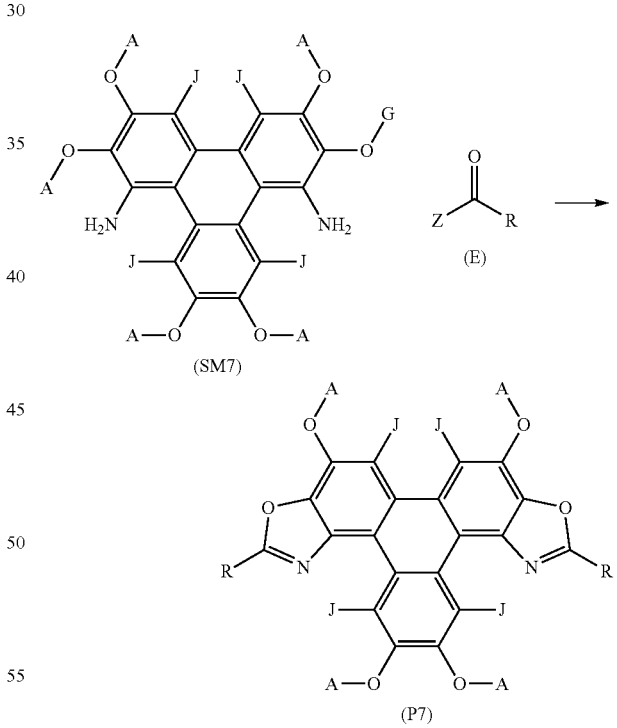

(SM7)

(E)

(P7)

wherein (SM7) represents a triphenylene core, (P7) represents a triphenylene derivative;
A independently represents a hydrogen atom, an aryl group, an alkyl group comprising 1 to 20 carbons (e.g. 1 to 15 carbons, or 1 to 10 carbons, or 10, 9, 8, 7, 6, 5, 4, 3, 2 or 1 carbons);
J independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group (e.g. a phenol group).

G independently represents a substituted carbon atom;
(E) represents the reagent;
R independently represents an aromatic group and/or an aliphatic group;
Z is one of an oxygen atom, a derivatised oxygen atom, a chlorine atom, or a bromine atom;

and wherein the triphenylene core (SM7) and the reagent (E) undergo an intermolecular coupling reaction to produce triphenylene derivative (P7).

The method may comprise synthesising triphenylene derivatives, wherein the triphenylene core starting material comprises the formula:

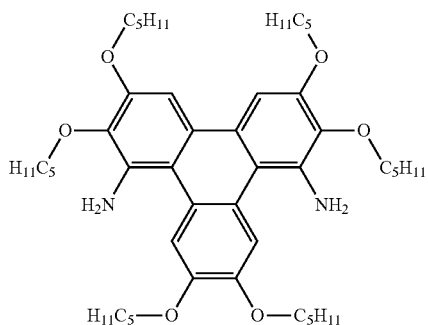

A yet further aspect of the invention provides a method of synthesising polycyclic aromatic hydrocarbon derivatives (P8), comprising the general formula:

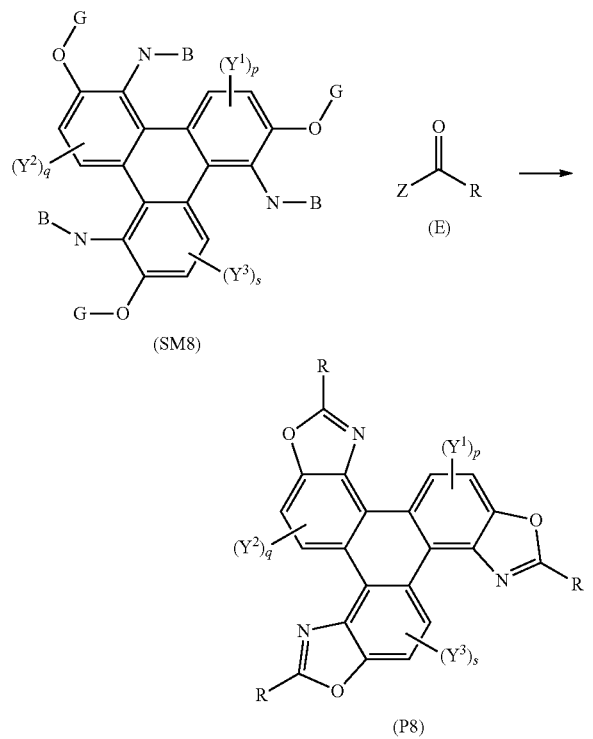

wherein (SM8) represents a polycyclic aromatic hydrocarbon core, (P8) represents a polycyclic aromatic hydrocarbon derivative;

p, q, and s are independently an integer of 1 to 2;
$Y^1$, $Y^2$, and $Y^3$ independently represent one or more of a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group;
G independently represents a substituted carbon atom;
N is a nitrogen atom;
B is one or more hydrogen atoms;
(E) represents the reagent;
R independently represents an aromatic group and/or an aliphatic group;
Z is one of an oxygen atom, a derivatised oxygen atom, a chlorine atom, or a bromine atom, or any good leaving group;

and wherein the polycyclic aromatic hydrocarbon core (SM8) and the reagent (E) undergo an intermolecular coupling reaction to produce the polycyclic aromatic hydrocarbon derivative (P8).

The method may comprise synthesising triphenylene derivatives (P9) comprising the general formula:

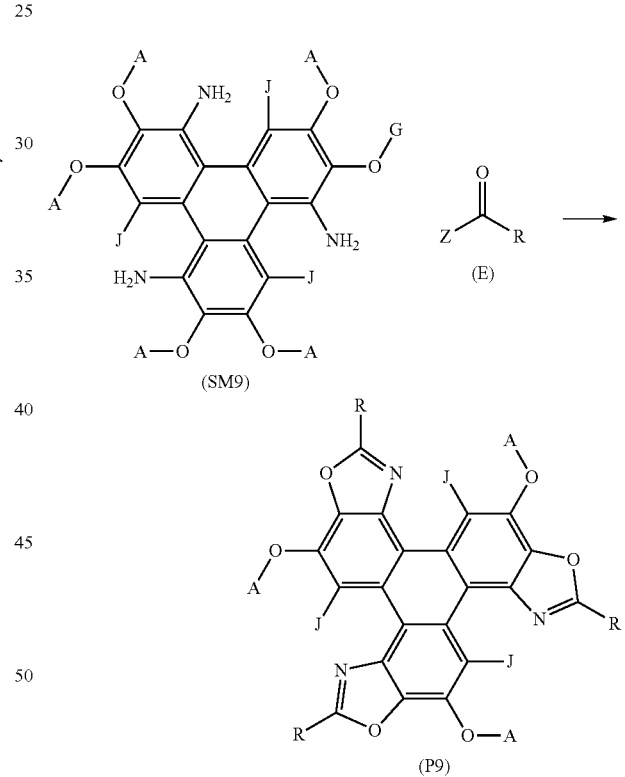

wherein (SM9) represents a triphenylene core, (P9) represents a triphenylene derivative;
A independently represents a hydrogen atom, an aryl group, an alkyl group comprising 1 to 20 carbons (e.g. 1 to 15 carbons, or 1 to 10 carbons, or 10, 9, 8, 7, 6, 5, 4, 3, 2 or 1 carbons);
J independently represent a hydrogen atom, a deuterium atom, a fluorine atom, a chlorine atom, a bromine atom, a carbon atom, an oxygen atom (e.g. an alkylated oxygen atom), a nitrogen atom (e.g. an alkylated nitrogen atom), a cyano group, a nitro group, an alkyl group and/or an aryl group (e.g. a phenol group).

G independently represents a substituted carbon atom;
(E) represents the reagent;
R independently represents an aromatic group and/or an aliphatic group;
Z is one of an oxygen atom, a derivatised oxygen atom, a chlorine atom, or a bromine atom;
and wherein the triphenylene core (SM9) and the reagent (E) undergo an intermolecular coupling reaction to produce triphenylene derivative (P9).

The method of synthesising triphenylene derivatives may comprise use of the starting material with the formula:

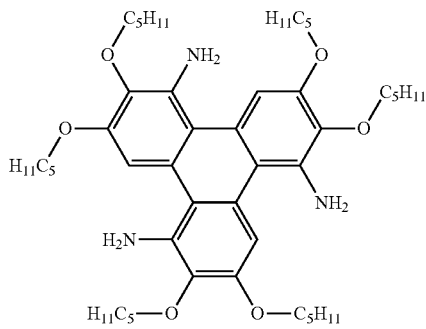

The method may further comprise a transition metal catalyst. The transition metal catalyst may be a rhodium based catalyst. Additionally or alternatively, the transition metal catalyst may be a palladium Pd(II) catalyst, for example, palladium acetate.

The method may further comprise a reagent to replace, in situ, group Z with a good leaving group.

The reagent (E) may be a carboxylic acid, for example, benzoic acid or a substituted benzoic acid. Alternatively, the reagent (E) may be an acyl chloride, for example, benzyl chloride or a substituted benzyl chloride.

The method may comprise heating the triphenylene core in a solvent, e.g. toluene, to reflux, in the presence of a palladium catalyst, e.g. Pd(OAc)$_2$, wherein Compound (E) is a carboxylic acid, i.e. Z is an OH group.

The method may further comprise a species to replace group Z with a good leaving group, for example, the species may be (diacetoxyiodo)benzene).

Alternatively, the method may comprise heating the polycyclic aromatic hydrocarbon core, e.g. the triphenylene core, in a solvent, e.g. toluene, to reflux, wherein Compound (E) is an acyl chloride, i.e. Z is a chlorine atom. The method may further comprise heating the reaction mixture to 240° C.

It is to be understood that the polycyclic aromatic derivatives may be further functionalised to produce analogues. For example, the polycyclic aromatic hydrocarbon derivatives, e.g. the triphenylene derivatives, may undergo bromination, e.g. using Br$_2$, to add a bromine atom to one or more aromatic carbon atoms. The bromine atom may act as a functional group to undergo further chemical transformations, e.g. to functionalise the polycyclic aromatic hydrocarbon derivatives with a phenol group. In embodiments, J may represent a bromine atom and/or a phenol group. The bromine atom and/or phenyl group may be used to further functionalise the polycyclic aromatic hydrocarbon derivative.

Additionally or alternatively, the alkyl groups of one or more of the alkoxy groups (e.g. the OC$_5$H$_{11}$ groups) may be de-alkylated to form hydroxyl (e.g. phenol) groups (e.g. using boron tribromide).

The polycyclic aromatic hydrocarbon derivatives may act as bio-labels or bio-probes.

Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible. For the avoidance of doubt, the terms "may", "and/or", "e.g.", "for example" and any similar term as used herein should be interpreted as non-limiting such that any feature so-described need not be present. Indeed, any combination of optional features is expressly envisaged without departing from the scope of the invention, whether or not these are expressly claimed. The applicant reserves the right to change any originally filed claim or file any new claim accordingly, including the right to amend any originally filed claim to depend from and/or incorporate any feature of any other claim although not originally claimed in that manner.

Embodiments of the invention will now be described by way of example only with reference to the accompanying drawings in which:

FIGS. 7A-7G are examples of polycyclic aromatic hydrocarbon derivatives according to examples of the invention;

Figure 1:
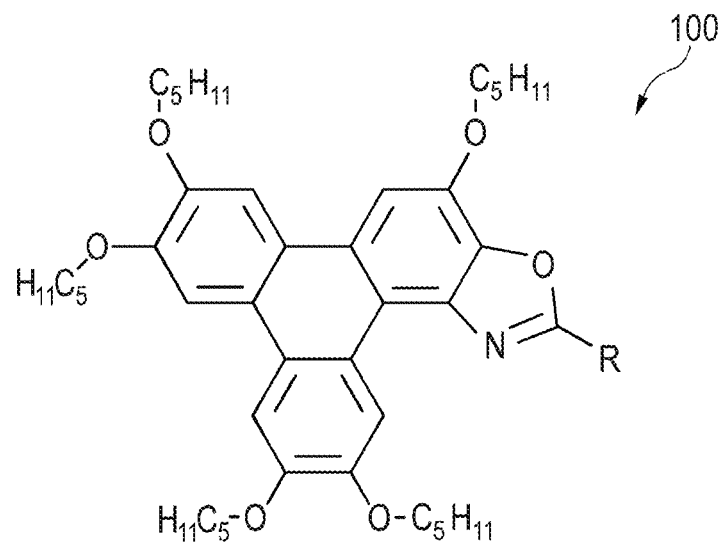
FIG. 1 is a representative structure of a series of triphenylene derivatives according to some embodiments of the invention.

Referring now to FIG. 1, there is shown a representative structure of a triphenylene derivative series 100 according to some embodiments of the invention. In this series, the R group is changed to provide analogues of the triphenylene derivative series 100. As is described in more detail below, the R group may be selected to alter the luminescent and/or other advantageous properties of the triphenylene derivative series 100.

Figure 2:
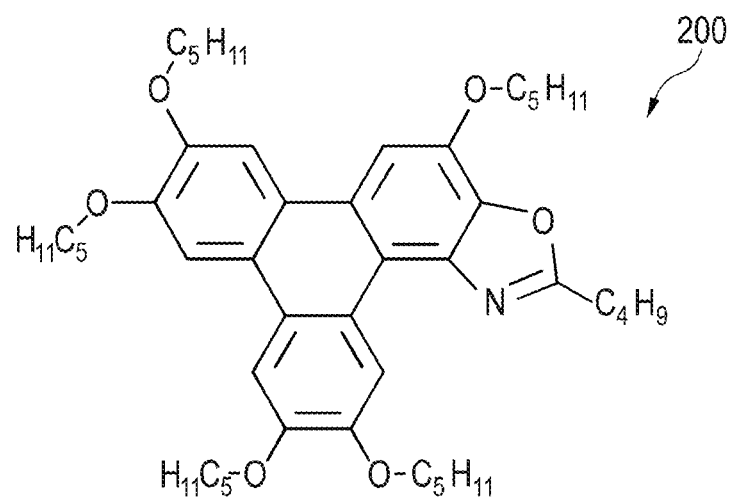
FIG. 2 is a triphenylene derivative according to a first example of the invention.
Figure 3:
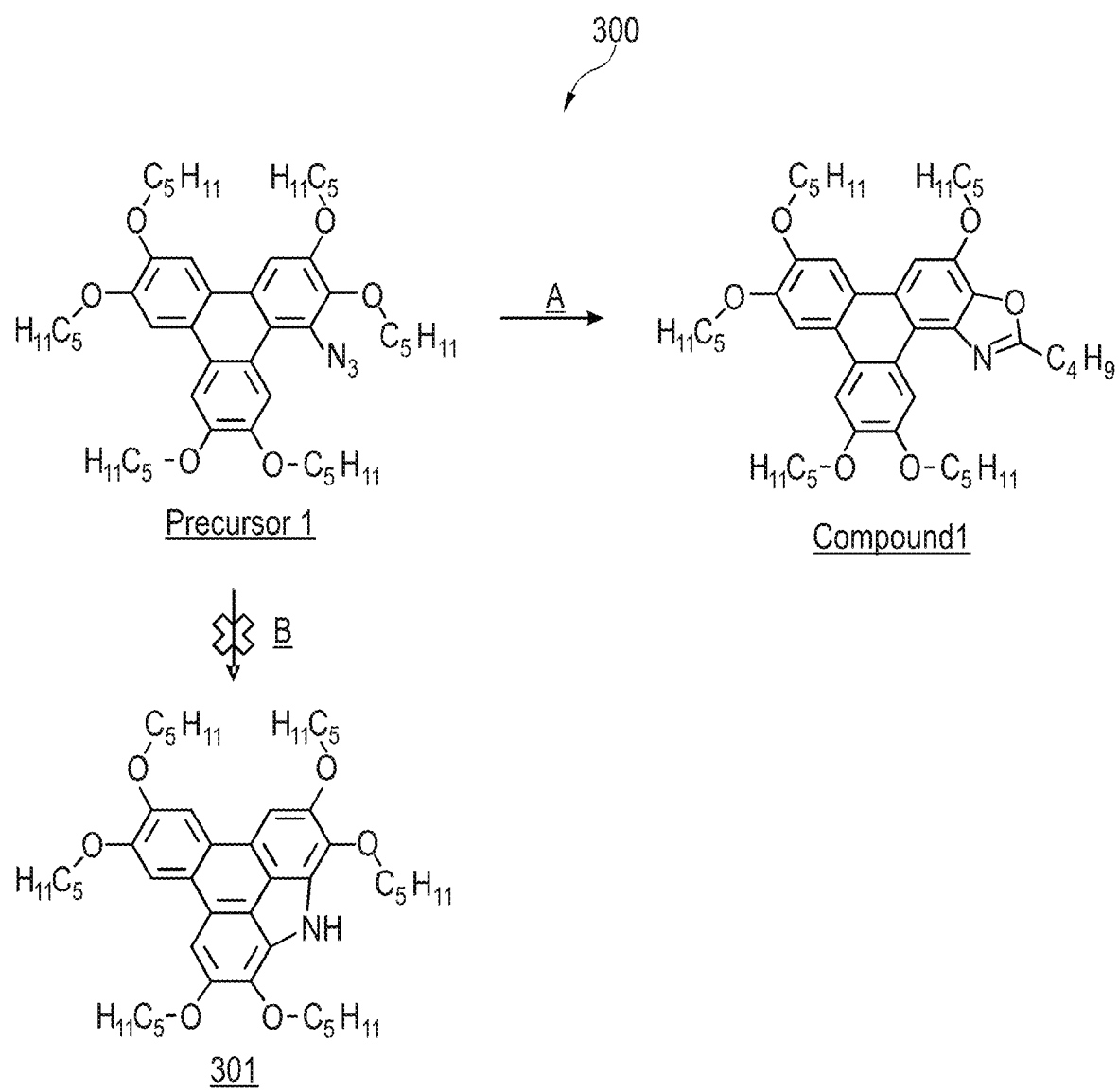
FIG. 3 is a method of synthesising a triphenylene derivative of the first embodiment of the invention, as shown in FIG. 2.

Referring now to FIG. 2, there is shown a triphenylene derivative 200, Compound 1, according to an embodiment of the invention. In this embodiment, the R group is an alkyl group of the formula $C_4H_9$. Referring also to FIG. 3, there is shown a schematic synthetic route 300 to Compound 1. There is shown two pathways, Pathway A and Pathway B, for a rearrangement reaction of Precursor 1, which is an azide (1-azido-2,3,6,7,10,11-hexakis(pentyloxy)triphenylene), under the reaction conditions of heating in xylene under nitrogen at 175° C. for 16 h. Pathway B, wherein Precursor 1 rearranges to produce a carbazole 301, was expected by the inventors to be successful. However, this is not observed. Instead, and unexpectedly, Pathway A, wherein Precursor 1 rearranges to produce Compound 1, was observed.

Without wishing to be bound by theory, it is thought that the reaction Precursor 1 in Pathway A proceeds via an intramolecular ring closure mechanism to lead to the formation of Compound 1 in quantitative yield. The carbazole 301 product was not observed. The method of synthesising Compound 1 is described in Example 1 below. It should be noted that Compound 1 is synthesised using the intramolecular route. We have found that other alkyl analogues (e.g. C7, C8 analogues) can be made in a similar fashion. Other embodiments of the invention require a different method of synthesis, which proceeds via a different chemical mechanism.

Figure 4:
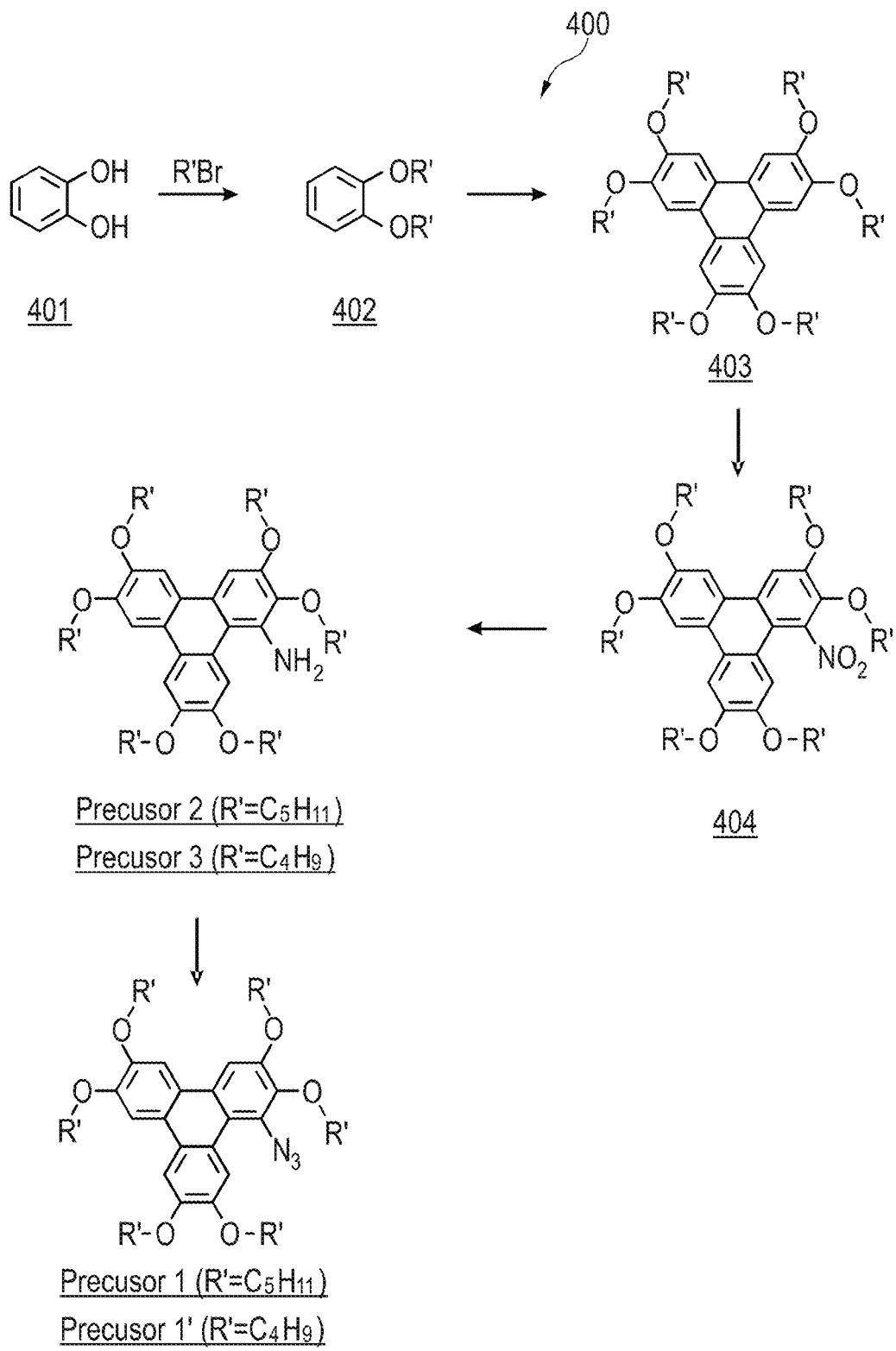
FIG. 4 is a schematic synthetic route of the prior art to the precursors of the triphenylene derivatives according to embodiments of the invention.

Referring now to FIG. 4, there is shown a schematic synthetic route 400 of the prior art (N. Boden et. al. J. Mater. Chem., 1995, 5, 2275) to produce Precursor 1, and in addition Precursor 2, which is an amine (2,3,6,7,10,11-hexakis(pentyloxy)-1-triphenylenylamine), and Precursor 3, which is an amine (2,3,6,7,10,11-hexabutoxy-1-triphenylenylamine). The full procedures to synthesise Precursor 1, Precursor 2, and Precursor 3, starting from catechol 401, are found in the prior art and are incorporated herein by reference.

Figure 5A:
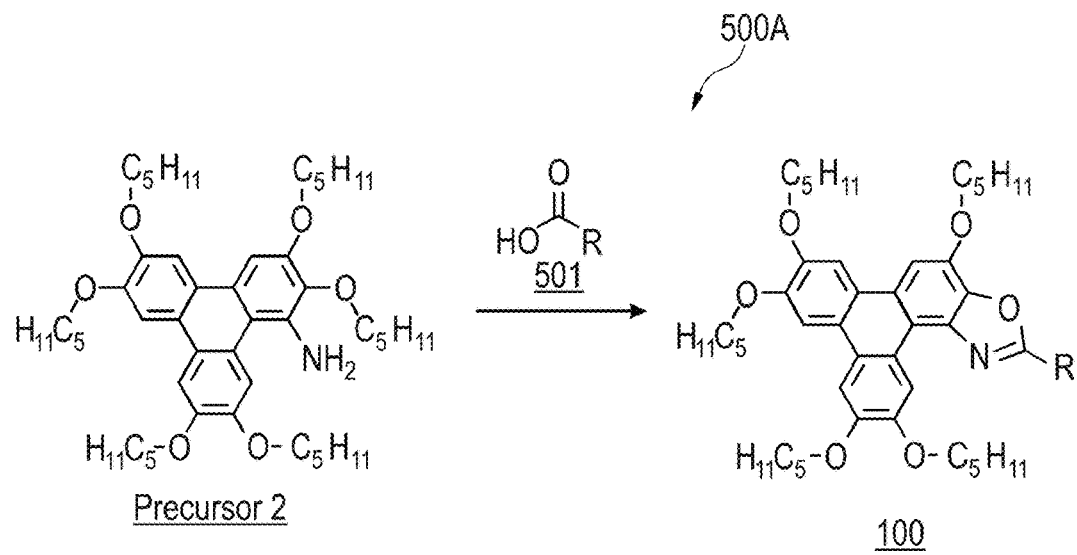
FIG. 5A is a schematic synthetic route for the synthesis of triphenylene derivatives according to embodiments of the invention, as shown in FIG. 1.

Referring now to FIG. 5A, there is shown a schematic synthetic route 500A for the formation of the triphenylene derivative series 100 of the present invention. There is shown Precursor 2, a carboxylic acid 501, and the triphenylene derivative series 100. The carboxylic acid 501 comprises an R group, which is incorporated into the oxazole moiety of the triphenylene derivative series 100. The R group may be an alkyl group, or an aryl group, i.e. the carbon atom bonded to the oxazole moiety in the triphenylene derivative series 100 may be either $sp^2$ or $sp^3$ hybridised.

The following general procedure may be followed to synthesise the triphenylene derivative series 100 using the method 500A of FIG. 5A. A solution of the appropriate carboxylic acid (1.31 mmol), palladium diacetate (0.005 mmol) and iodobenzene diacetate (0.157 mmol) in PhMe (5 mL) was heated at 70° C. under $N_2$ for 20 min. A solution of Precursor 2 (100 mg; 0.131 mmol) in PhMe (2 mL) was added and heated under reflux for 48-72 h, whilst stirring. The solution was cooled to room temperature and diluted with $CH_2Cl_2$ (20 mL). The organic phase was washed with aqueous NaOH (1M; 2×20 mL), separated and the organic phase was dried in vacuo. The crude black solid was purified by flash column chromatography (silica; 40% $CH_2Cl_2$: 60% n-hexane) to afford the triphenylene derivative series 100.

This method was based on a prior art method for the formation of a carbazole (J. A. Jordan-Hore, C. C. C. Johansson, M. Gulias, E. M. Beck, M. J. Gaunt, J. Am. Chem. Soc., 2008, 130, 16184-16186.) and, as previously stated, was surprisingly able to form the triphenyl derivative series 100, i.e. the triphenylene oxazole.

Figure 5B:
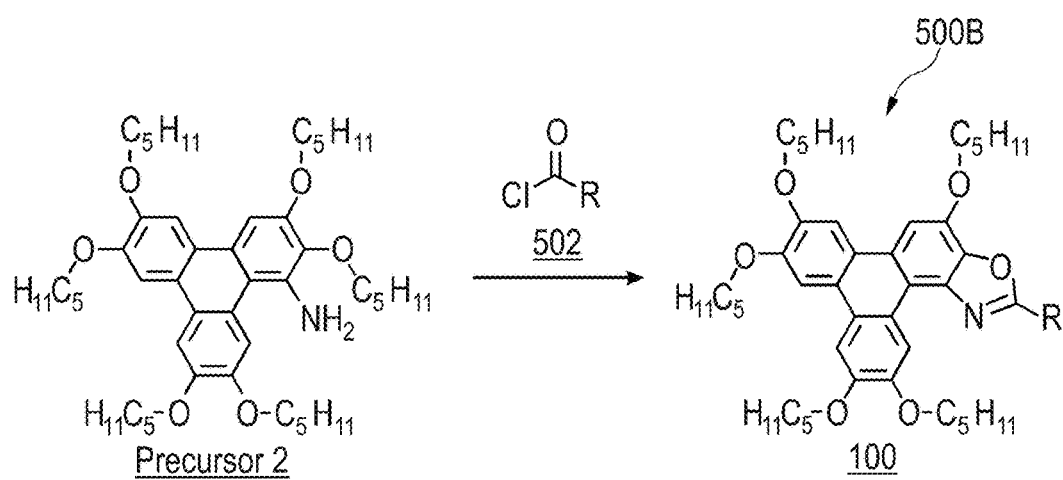
FIG. 5B is an alternative schematic synthetic route for the synthesis of triphenylene derivatives according to embodiments of the invention, as shown in FIG. 1.
Figure 5B:
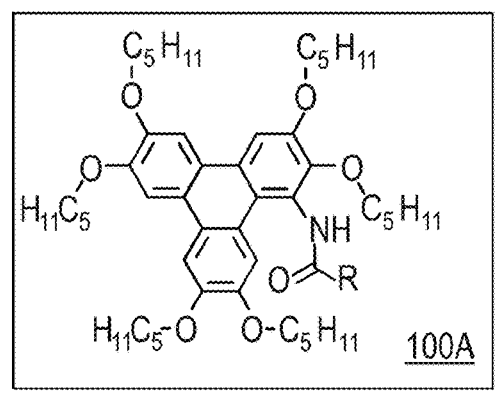

Referring also to FIG. 5B there is shown a schematic synthetic route 500B for the formation of the triphenylene derivative series 100 of the present invention. There is shown Precursor 2, an acyl chloride 502, and the triphenylene derivative series 100. There is further shown an intermediate amide 100A. In this method, the acyl chloride 502 comprises the R group, which is incorporated into the oxazole moiety of the triphenylene derivative series 100. As with the method 500A of FIG. 5A, the R group may be an alkyl group, or an aryl group, i.e. the carbon atom bonded to the oxazole moiety in the triphenylene derivative series 100 may be either $sp^2$ or $sp^3$ hybridised.

The following general procedure may be followed to synthesise the triphenylene derivative series 100 using the method 500B of FIG. 5B. A solution of Precursor 2 or Precursor 3 (100 mg; 0.132 mmol), the appropriate acyl chloride (0.658 mmol), and triethylamine (0.574 mmol) in PhMe (5 mL) was heated at reflux under $N_2$ for 18 hours whilst stirring. The resulting solution was further heated at 240° C. for 15 minutes. The solution was cooled to room temperature and diluted with $CH_2Cl_2$ (20 mL). The organic phase was washed with aqueous NaOH (1M; 2×20 mL), separated and the organic phase was dried in vacuo. The crude black solid was purified by flash column chromatography (silica; 40% $CH_2Cl_2$: 60% n-hexane) to afford the triphenylene derivative series 100.

Without wishing to be bound by theory, the inventors believe that the acyl chloride 502 forms an intermediate amide (shown in FIG. 5B as intermediate amide 100A) with the Precursor 2 in situ, which subsequently undergoes a ring closure to form the triphenylene derivative series 100. In contrast to that observed in FIG. 3 for Compound 1, the reactions of both method 500A and method 500B are intermolecular coupling reactions of the carboxylic acid or the acyl chloride with the Precursor 2. The intermediate amide 100A has been isolated for the method shown in FIG. 5B when R=Ph.

Advantageously, the methods of FIG. 5A and FIG. 5B enable a huge number of analogues of the triphenylene derivate 100 to be synthesised by varying the R group of the carboxylic acid 501 in the method 500A of FIG. 5A, or the acyl chloride 502 in the method 500B of FIG. 5B. The triphenylene derivative series 100 of the present invention exhibit a number of desirable properties, in particular desirable luminescent characteristics. Advantageously, the R group may be altered to 'tune' these properties. More advantageously, within the known parameters of this invention, the R group may be specifically selected to enable the 'tuning' of the desirable luminescent characteristics. This is demonstrated in detail in the section below.

Figure 6:
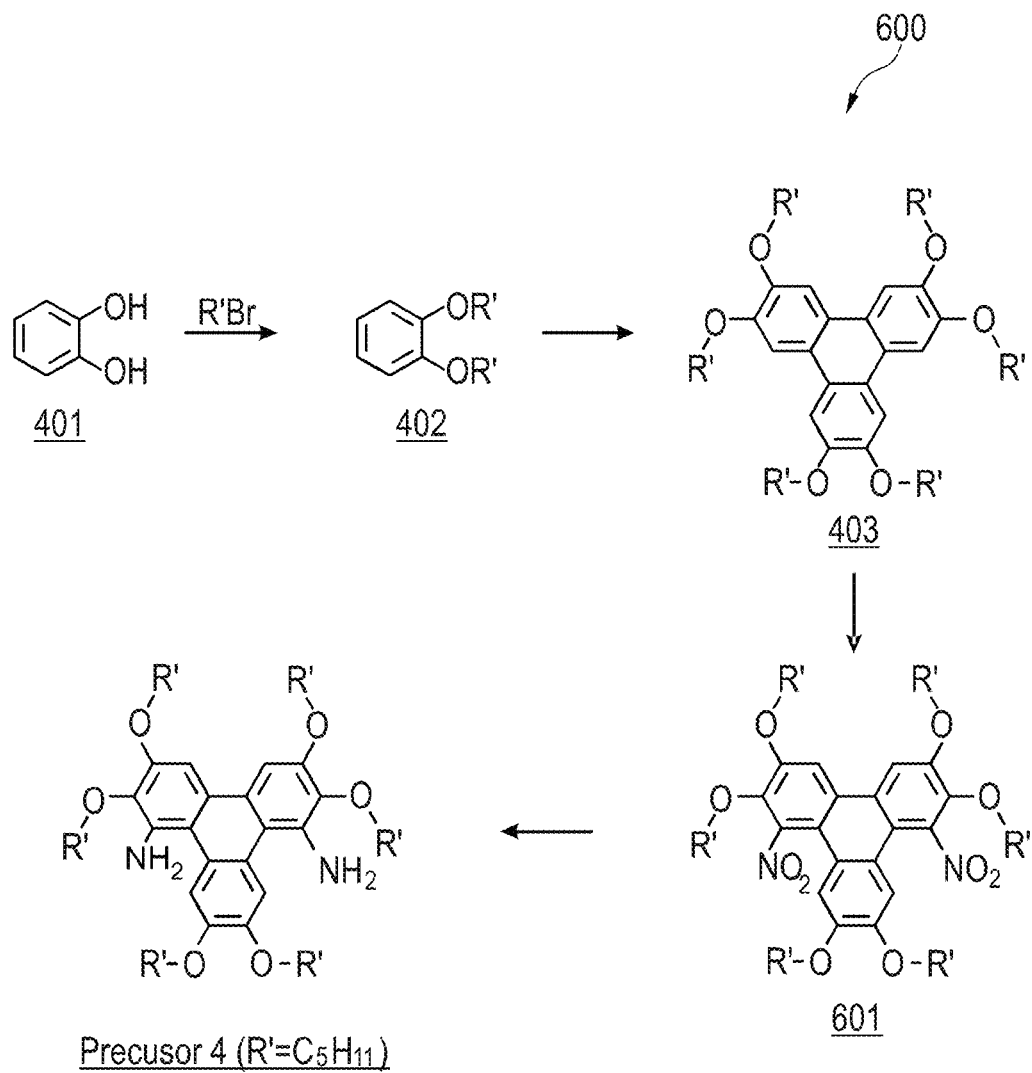
FIG. 6 is a schematic synthetic route to the precursor of the triphenylene derivatives according to further embodiments of the invention.
Figure 7A:
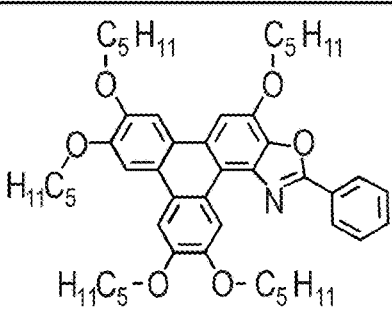
Figure 7A:
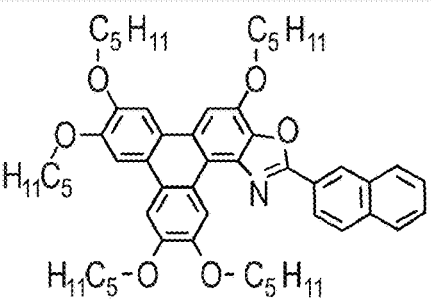
Figure 7A:
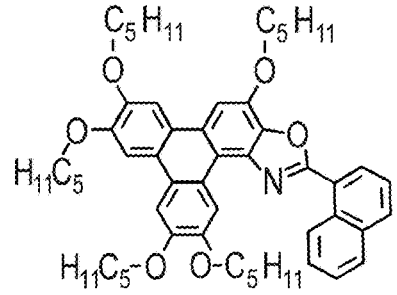
Figure 7A:
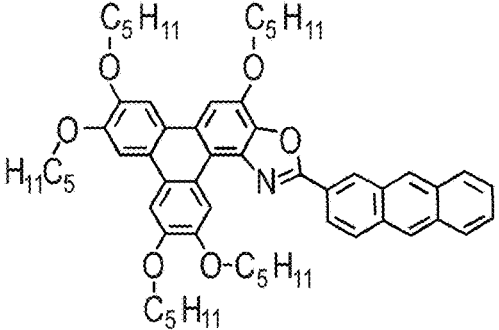
Figure 7A:
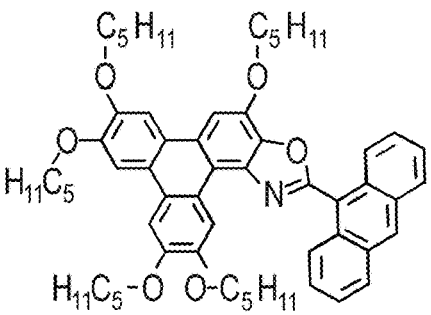
Figure 7C:
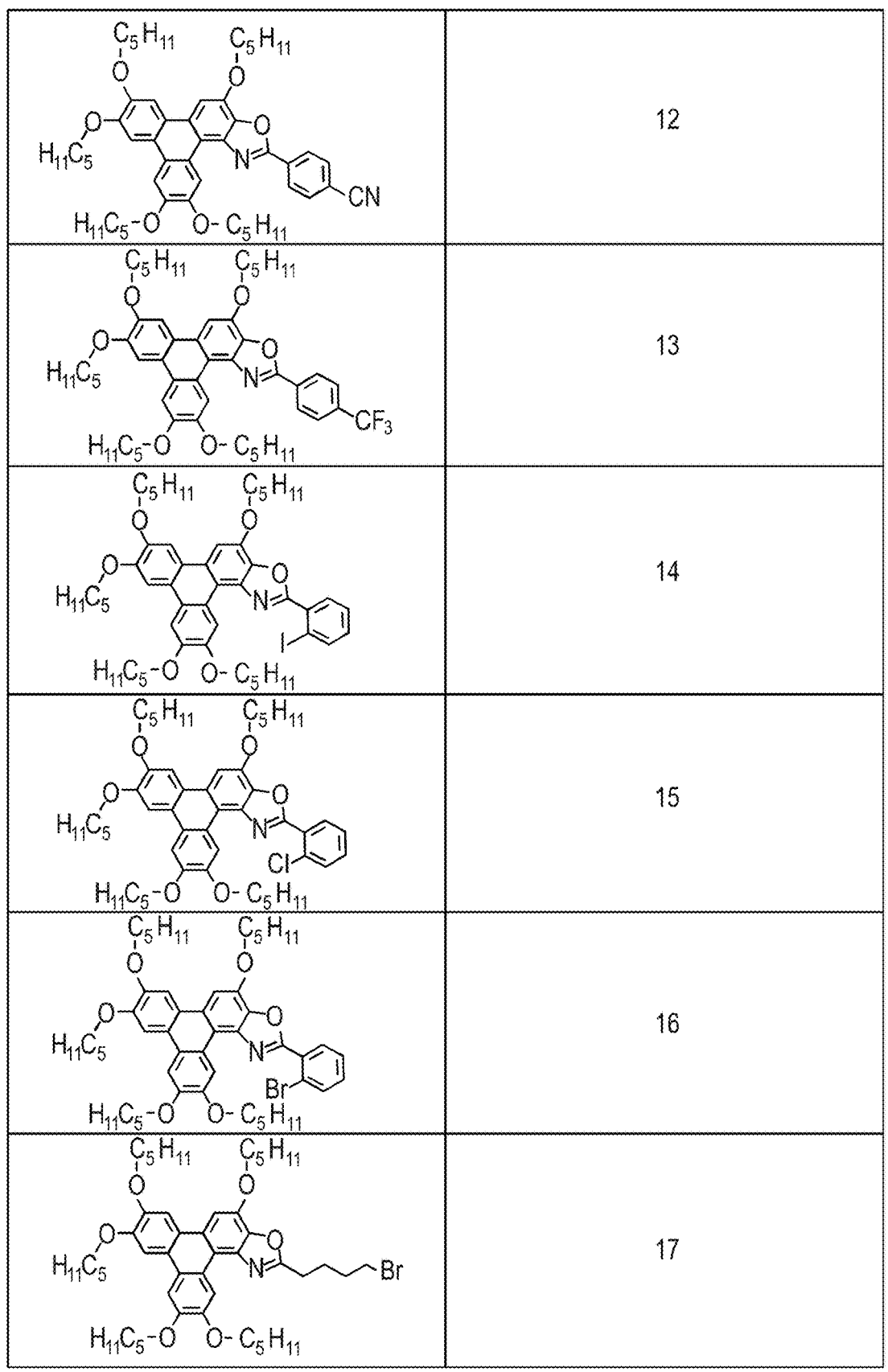
Figure 7D:
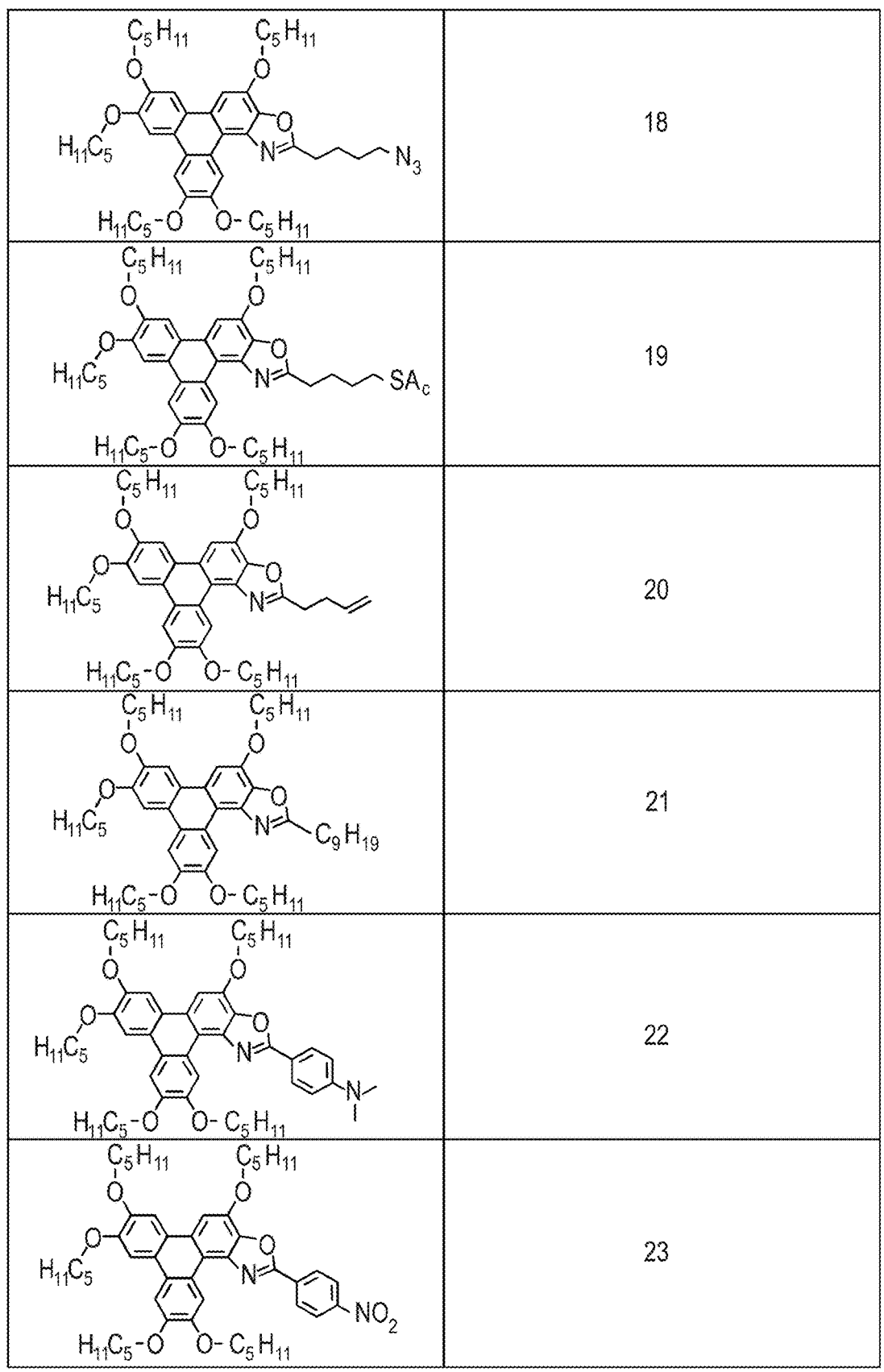
Figure 7E:
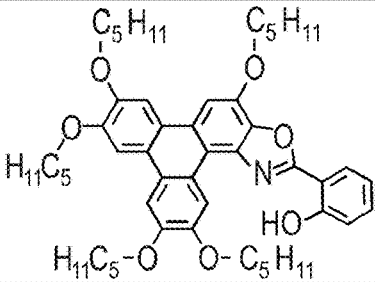
Figure 7E:
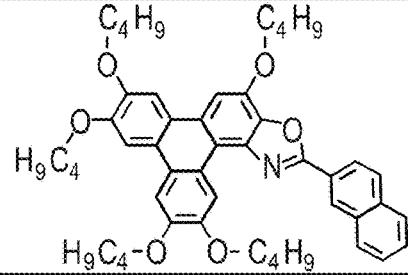
Figure 7E:
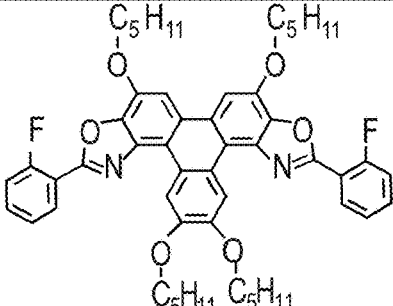
Figure 7E:
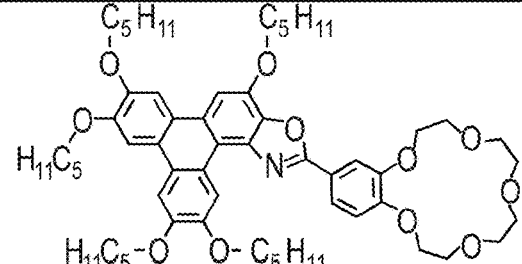
Figure 7E:
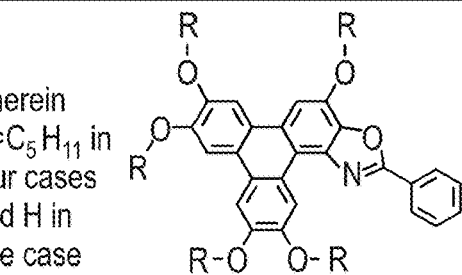
Figure 7E:
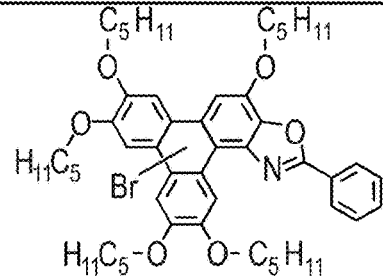
Figure 7G:
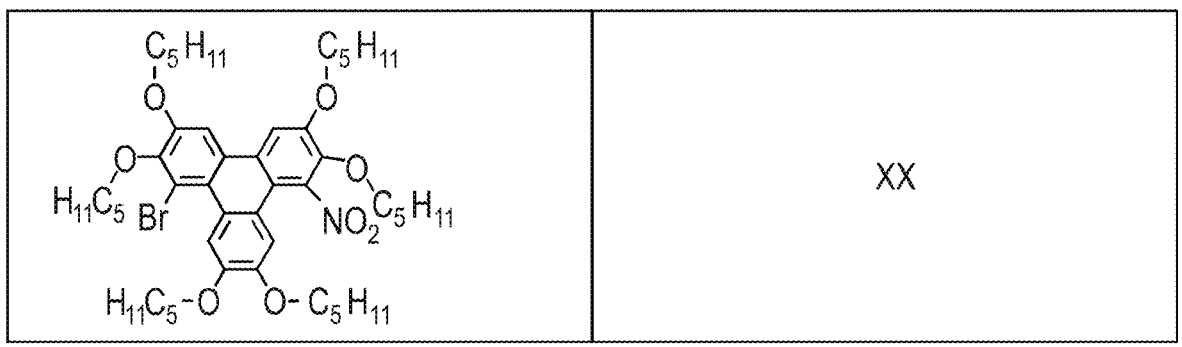

Referring now to FIG. 6, there is shown a schematic synthetic route 600 to produce Precursor 4, which is an amine. When R'=$C_5H_{11}$ then Precursor 4 is 2,3,6,7,10,11-hexakis(pentyloxy)-1,8-triphenylenediamine. Precursor 4 is synthesised from di-nitro triphenylene 601. Di-nitro triphenylene 601 is formed as a side product in the prior art method that was used to synthesis the mono-nitro intermediate 404 (shown in FIG. 4). Di-nitro triphenylene 601 may be isolated using flash column chromatography in an earlier fraction than the mono-nitro intermediate 404.

To further exemplify the invention, reference is also made to the following non-limiting Examples.

All compound names were generated using ChemDraw® software.

Referring to FIGS. 7A-7G there is shown Examples (Compounds 2-26) of the triphenylene derivative series 100. The methods for synthesising Compounds 2-26 are described below.

EXAMPLE 1—METHOD OF SYNTHESISING COMPOUND 1

Compound 1 was synthesised using the following method. A solution of Precursor 1 (100 mg; 0.13 mmol) in o-xylene (8 mL) was added to a flask. This was then heated and held at 175° C. for 16 h to afford Compound 1 (51% yield).

In the alternative, Compound 1 was synthesised using the following method. A solution of Precursor 1 (100 mg; 0.13 mmol) in dry PhMe (8 mL) was added to a flask containing rhodium octanoate dimer (8 mg; 0.01 mmol), under a $N_2$ atmosphere. This was then heated and held at reflux for 20 h. The reaction was cooled to room temperature and then evaporated to dryness in vacuo, the solid was then purified via flash column chromatography (silica; 95% n-hexane:5% ethyl acetate) to afford Compound 1 as a white solid (96 mg; 99%).

The name for Compound 1 is 8-butyl-2,3,6,11,12-pentakis(pentyloxy)triphenyleno[1,2-d]oxazole.

Compound 1 had the following characterisation data: $^1$H NMR (300 MHz, CDCl$_3$) δH: 10.01 (1H, s), 7.94 (1H, s), 7.90 (1H, s), 7.88 (1H, s), 7.85 (1H, s), 4.42 (2H, t, J 6.7 Hz), 4.37 (2H, t, J 6.7 Hz) 4.29-4.23 (6H, m), 3.09 (2H, t, J 7.5 Hz), 2.05-1.92 (10H, m), 1.62-1.43 (24H, m), 1.06-0.96 (18H, m) ppm. $^{13}$C NMR (100 MHz, CDCl3) δC: 165.6, 149.5, 149.1, 148.7, 148.3, 142.9, 140.1, 139.8, 124.6, 123.9, 123.5, 123.3, 116.3, 111.0, 108.3, 106.9, 106.8, 102.6, 69.9, 69.6, 69.5, 68.8, 29.2, 29.0, 28.8, 28.4, 28.3, 22.6, 22.4, 14.2, 13.9 ppm. ES+ MS m/z: 756.5 ([M+H]$^+$ 15%), 778.5 ([M$^+$ Na]$^+$ 100%). IR λ$^{-1}$ (neat): 3112 w (C—H), 2953 m (C—H), 1617 w (C=N), 1517 w (benzene ring), 1259 s (C—O), 1177 s (C—O), 1159 s (C—O) cm-1. Elemental analysis Found: C, 76.09; H, 9.17; N, 1.95. $C_{48}H_{69}NO_6$ requires C, 76.25; H, 9.20; N, 1.85%.

EXAMPLE 2—METHOD OF SYNTHESISING COMPOUND 2

Compound 2 was synthesised using the following method. A slurry of benzoic acid (160 mg; 1.31 mmol), palladium diacetate (0.005 mmol) and iodobenzene diacetate (0.16 mmol) in PhMe (5 mL) was heated at 70° C. under $N_2$ for 20 min. Precursor 2 (100 mg, 0.13 mmol) in PhMe (2 mL) was added and the reaction was heated and held at reflux for 72 h. The mixture was cooled to room temperature and diluted with CH$_2$Cl$_2$ (20 mL). The mixture was washed with 1M NaOH (2×20 mL) and the organic phase was dried in vacuo. The crude black solid was purified via flash column chromatography (60% n-hexane: 40% CH$_2$Cl$_2$) to afford Compound 2 as a white solid (35 mg; 34%).

The name for Compound 2 is 2,3,6,11,12-pentakis(pentyloxy)-8-phenyltriphenyleno[1,2-d]oxazole.

Compound 2 had the following characterisation data: $^1$H NMR (300 MHz, CDCl$_3$) δH: 10.13 (1H, s), 8.40-8.37 (2H, m), 7.92 (1H, s), 7.88 (1H, s), 7.87 (1H, s), 7.77 (1H, s), 7.57-7.55 (1H, m), 4.48-4.43 (4H, m), 4.30-4.23 (6H, m), 2.12-1.92 (10H, m), 1.69-1.54 (12H, m), 1.53-1.45 (12H, m), 1.04-0.96 (18H, m) ppm. $^{13}$C NMR (100 MHz, CDCl$_3$) δC: 161.4, 149.5, 149.0, 148.7, 148.3, 142.9, 140.5, 140.2, 131.2, 128.9, 127.5, 127.1, 124.7, 123.8, 123.4, 123.3, 116.4, 110.9, 108.2, 106.8, 106.6, 103.8, 69.8, 69.5, 68.9, 29.2, 29.0, 28.4, 28.3, 22.6, 22.6, 14.1 ppm. ES+MS m/z: 775.5 ([M]+ 22%), 776.5 ([M+H]+ 37%), 798.5 ([M+Na]+ 100%). Elemental analysis Found: C, 77.46; H, 8.44; N, 1.75%. $C_{50}H_{65}NO_6$ requires C, 77.38; H, 8.44; N, 1.80%.

EXAMPLE 3—METHOD OF SYNTHESISING COMPOUND 3

Compound 3 was synthesised using the following method. A solution of 2-naphthalene carboxylic acid (225 mg, 1.31 mmol), palladium diacetate (0.005 mmol) and iodobenzene diacetate (0.157 mmol) in PhMe (5 mL) was heated at 70° C. under $N_2$ for 20 min. A solution of Precursor 2 (100 mg; 0.131 mmol) in PhMe (2 mL) was added and heated under reflux for 48-72 h, whilst stirring. The solution was cooled to room temperature and diluted with CH$_2$Cl$_2$ (20 mL). The organic phase was washed with aqueous NaOH (1M; 2×20 mL), separated and the organic phase was dried in vacuo. The crude black solid was purified by flash column chromatography (silica; 40% CH$_2$Cl$_2$: 60% n-hexane) to afford Compound 3 as a yellow solid (35 mg; 32%).

The name for Compound 3 is 8-(naphthalen-2-yl)-2,3,6, 11,12-pentakis(pentyloxy)triphenyleno[1,2-d]oxazole.

Compound 3 had the following characterisation data: $^1$H NMR (300 MHz, CDCl$_3$) δH: 10.22 (1H, s), 8.89 (1H, s), 8.49 (1H, dd, J 8.6, 1.7), 8.05-7.99 (2H, m), 7.96-7.91 (5H, m), 7.62-7.59 (2H, m), 4.54 (2H, t, J 6.8), 4.51 (2H, t, J 6.8), 4.32-4.25 (6H, m), 2.17-1.93 (10H, m), 1.76-1.42 (20H, m), 1.06-0.97 (15H, m) ppm. $^{13}$C NMR (100 MHz, CDCl$_3$) δC: 161.7, 149.8, 149.3, 149.0, 148.6, 143.2, 140.9, 140.6, 135.0, 133.4, 129.3, 128.9, 128.3, 128.0, 127.9, 127.4, 127.2, 125.0, 125.0, 124.4, 124.2, 123.7, 123.6, 116.7, 111.2, 108.5, 107.1, 107.0, 103.9, 70.2, 70.1, 69.8, 69.2, 29.6, 29.5, 28.9, 28.8, 28.7, 23.1, 23.0, 14.6, 14.5 ppm. MALDI+ m/z: 825.5 ([M]+ 100%). IR λ–1 (neat): Elemental analysis Found: C, 78.95; H, 8.02; N, 1.83%. $C_{54}H_{67}NO_6$ requires C, 78.51; H, 8.17; N, 1.70%.

EXAMPLE 4—METHOD OF SYNTHESISING COMPOUND 4

Compound 4 was synthesised using the following method. A solution of 1-naphthalene carboxylic acid (225 mg, 1.31 mmol), palladium diacetate (0.005 mmol) and iodobenzene diacetate (0.157 mmol) in PhMe (5 mL) was heated at 70° C. under $N_2$ for 20 min. A solution of Precursor 2 (100 mg; 0.131 mmol) in PhMe (2 mL) was added and heated under reflux for 48-72 h, whilst stirring. The solution was cooled to room temperature and diluted with CH$_2$Cl$_2$ (20 mL). The organic phase was washed with aqueous NaOH (1M; 2×20 mL), separated and the organic phase was dried in vacuo. The crude black solid was purified by flash column chromatography (silica; 40% CH$_2$Cl$_2$: 60% n-hexane) to afford Compound 4 as a yellow solid (24 mg; 22%).

The name for Compound 4 is 8-(naphthalen-1-yl)-2,3,6,11,12-pentakis(pentyloxy)triphenyleno[1,2-d]oxazole.

Compound 4 had the following characterisation data: $^1$H NMR (300 MHz, CDCl$_3$) δH: 10.15 (1H, s), 9.82 (1H, d, J 8.3 Hz), 8.59 (1H, dd, J 7.3, 1.2 Hz), 8.08 (1H, d, J 8.3 Hz), 8.01-7.98 (3H, m), 7.94 (2H, m), 7.71-7.61 (3H, m), 4.54-4.45 (4H, m), 4.32-4.26 (6H, m), 2.10-1.94 (10H, m), 1.70-1.35 (20H, m), 1.04-0.87 (15H, m) ppm. $^{13}$C NMR (100 MHz, CDCl$_3$) δC: 161.3, 149.9, 149.6, 149.1, 148.8, 143.2, 141.0, 139.9, 134.5, 132.4, 131.0, 129.6, 129.2, 127.8, 127.5, 126.9, 126.7, 125.5, 125.0, 124.2, 124.1, 123.8, 117.0, 111.0, 108.6, 107.3, 107.2, 104.4, 70.2, 69.9, 69.1, 29.6, 29.5, 29.0, 28.8, 28.7, 23.0, 14.5 ppm. MALDI+ m/z: 826.7 ([M+H]+ 100%). Elemental analysis Found: C, 78.49; H, 8.23; N, 1.73%. C$_{54}$H$_{67}$NO$_6$ requires C, 78.51; H, 8.17; N, 1.70%.

EXAMPLE 5—METHOD OF SYNTHESISING COMPOUND 5

Compound 5 was synthesised using the following method. A solution of 2-anthracene carboxylic acid (290 mg, 1.31 mmol), palladium diacetate (0.005 mmol) and iodobenzene diacetate (0.157 mmol) in PhMe (5 mL) was heated at 70° C. under N$_2$ for 20 min. A solution of Precursor 2 (100 mg; 0.131 mmol) in PhMe (2 mL) was added and heated under reflux for 48-72 h, whilst stirring. The solution was cooled to room temperature and diluted with CH$_2$Cl$_2$ (20 mL). The organic phase was washed with aqueous NaOH (1M; 2×20 mL), separated and the organic phase was dried in vacuo. The crude black solid was purified by flash column chromatography (silica; 40% CH$_2$Cl$_2$: 60% n-hexane) to afford Compound 5 as a yellow solid (22 mg; 20%).

The name for Compound 5 is 8-(anthracen-2-yl)-2,3,6,11,12-pentakis(pentyloxy)triphenyleno[1,2-d]oxazole.

Compound 5 had the following characterisation data: $^1$H NMR (300 MHz, CDCl$_3$) δH: 10.20 (1H, s), 9.00 (1H, s), 8.58 (1H, s), 8.47 (1H, s), 8.39 (1H, dd, J 8.9, 1.6 Hz) 8.13-8.10 (2H, m), 8.07-8.02 (2H, m), 7.93 (1H, s), 7.90-7.89 (3H, m), 4.57-4.47 (4H, m), 4.31-4.24 (6H, m), 2.19-1.96 (10H, m), 1.76-1.44 (20H, m), 1.08-0.97 (15H, m) ppm. $^{13}$C NMR (100 MHz, CDCl$_3$) δC: 161.8, 149.8, 149.4, 149.0, 148.6, 143.2, 141.0, 140.6, 133.1, 132.6, 132.3, 131.2, 129.2, 128.7 128.6, 128.2 127.4, 126.8, 126.6, 126.3, 125.0, 124.4, 124.2, 123.8, 123.6, 116.7, 111.3, 108.5, 107.1, 107.0, 104.0, 70.2, 70.1, 69.8, 69.2, 30.1, 29.6, 29.5, 28.9, 28.8, 28.7, 23.1, 23.0, 14.7, 14.5 ppm. MALDI+ m/z: 876.5 ([M+H]+ 100%). Elemental analysis Found: C, 79.49; H, 7.88; N, 1.51. C$_{58}$H$_{69}$NO$_6$ requires C, 79.51; H, 7.94; N, 1.60%.

EXAMPLE 6—METHOD OF SYNTHESISING COMPOUND 6

Compound 6 was synthesised using the following method. A solution of 9-anthracene carboxylic acid (290 mg; 1.31 mmol), palladium diacetate (0.005 mmol) and iodobenzene diacetate (0.157 mmol) in o-xylene (5 mL) was heated to 70° C. under N$_2$ for 20 min. A solution of Precursor 2 (100 mg, 0.131 mmol) in o-xylene (2 mL) was added and heated to 140° C. for 72 h. The mixture was cooled to room temperature and diluted with CH$_2$Cl$_2$ (20 mL). The mixture was washed with 1M NaOH (2×20 mL) and the organic phase was dried in vacuo. The crude black solid was purified by flash column chromatography (silica; 40% CH$_2$Cl$_2$: 60% n-hexane) to afford Compound 6 as a yellow solid (13 mg; 11%).

The name for Compound 6 is 8-(anthracen-9-yl)-2,3,6,11,12-pentakis(pentyloxy)triphenyleno[1,2-d]oxazole.

Compound 6 had the following characterisation data: $^1$H NMR (300 MHz, CDCl$_3$) δH: 10.18 (1H, s), 8.70 (1H, s), 8.49-8.44 (2H, m), 8.15-8.09 (2H, m), 8.03 (1H, s) 8.02 (1H, s) 7.95 (1H, s), 7.94 (1H,$) 7.58-7.52 (4H, m), 4.50 (2H, t, J 6.7 Hz), 4.33-4.27 (6H, m), 4.17 (2H, t, J 6.7 Hz), 2.05-1.93 (8H, m), 1.79 (2H, p, J 6.7, 1.0 Hz) 1.66-1.37 (20H, m), 1.03-0.92 (15H, m) ppm. $^{13}$C NMR δC: (100 MHz, CDCl$_3$) 160.6, 150.0, 149.6, 149.2, 148.8, 143.5, 141.0, 140.7, 131.9, 131.7, 131.3, 129.1, 127.7, 127.6, 126.4, 125.9 124.2, 123.8, 121.1, 117.1, 111.3, 108.7, 107.3, 107.2, 104.6, 70.4, 70.3, 69.9, 69.2, 29.6, 29.5, 29.0, 28.8, 28.7, 28.6, 28.5, 23.0, 22.9, 22.6, 14.5, 14.4, 14.3 ppm. MALDI$^+$ m/z: 876.5 ([M+H]$^+$ 100%). Elemental analysis Found: C, 79.13; H, 7.83; N, 1.77%. C$_{58}$H$_{69}$NO$_6$ requires C, 79.51; H, 7.94; N, 1.60%.

EXAMPLE 7—METHOD OF SYNTHESISING COMPOUND 7

Compound 7 was synthesised using the following method. A solution of 4-fluorobenzoic acid (187 mg; 1.31 mmol), palladium diacetate (0.005 mmol) and iodobenzene diacetate (0.157 mmol) in o-xylene (5 mL) was heated to 70° C. under N$_2$ for 20 min. A solution of Precursor 2 (100 mg, 0.131 mmol) in o-xylene (2 mL) was added and heated to 140° C. for 72 h. The mixture was cooled to room temperature and diluted with CH$_2$Cl$_2$ (20 mL). The mixture was washed with 1M NaOH (2×20 mL) and the organic phase was dried in vacuo. The crude black solid was purified by flash column chromatography (silica; 40% CH$_2$Cl$_2$: 60% n-hexane) to afford Compound 7 as a yellow solid (13 mg; 9%).

The name for Compound 7 is 8-(4-fluorophenyl)-2,3,6,11,12-pentakis(pentyloxy)triphenyleno[1,2-d]oxazole.

Compound 7 had the following characterisation data: $^1$H NMR (300 MHz; CDCl$_3$) δH: 10.03 (s, 1H), 8.36-8.30 (m, 2H), 7.97-7.75 (m, 4H), 7.28-7.15 (m, 3H), 4.41 (t, J=6.6 Hz, 4H), 4.26 (m, 6H), 2.06-1.90 (m, 9H), 1.55 (m, 22H), 1.05-0.95 (m, 15H) ppm. $^{13}$C NMR (100 MHz; CDCl$_3$) δC: 166.0, 163.5, 160.6, 149.7, 149.1, 148.9, 148.5, 143.0, 140.5, 140.3, 129.8, 129.7, 127.3, 124.8, 123.9, 123.8, 123.5, 116.5, 116.3, 116.1, 111.1, 108.4, 107.0, 106.8, 103.7, 69.9, 69.8, 69.7, 69.5, 68.9, 29.7, 29.2, 29.0, 28.5, 28.4, 28.3, 22.6, 14.2, 14.1 ppm. $^{19}$F NMR (282 MHz, CDCl$_3$) δF: −108.0 ppm. MALDI+ m/z: 795.6 ([M+H+1]$^+$ 15%), 794.6 ([M+H]$^+$ 55%), 793.6 ([M]+ 100%). IR λ$^{-1}$ (neat): 2952 m (C—H), 2926 m (C—H), 2858 m (C—H), 1616 w (C=N), 1517 s (benzene ring), 1499 m (benzene ring), 1433 m (benzene ring), 1261 m (C—O), 1174 s (C—O) cm$^{-1}$.

EXAMPLE 8—METHOD OF SYNTHESISING COMPOUND 8

Compound 8 was synthesised using the following method. A solution of 3-fluorobenzoic acid (182 mg; 1.30 mmol), palladium diacetate (0.005 mmol) and iodobenzene diacetate (0.157 mmol) in o-xylene (5 mL) was heated to 70° C. under N$_2$ for 20 min. A solution of Precursor 2 (100 mg, 0.131 mmol) in o-xylene (2 mL) was added and heated to 140° C. for 72 h. The mixture was cooled to room temperature and diluted with CH$_2$Cl$_2$ (20 mL). The mixture was washed with 1M NaOH (2×20 mL) and the organic phase was dried in vacuo. The crude black solid was purified by flash column chromatography (silica; 40% CH$_2$Cl$_2$: 60% n-hexane) to afford Compound 8 as a yellow solid (13 mg; 11%).

The name for Compound 8 is 8-(3-fluorophenyl)-2,3,6,11,12-pentakis(pentyloxy)triphenyleno[1,2-d]oxazole.

Compound 8 had the following characterisation data: $^1$H NMR (300 MHz; CDCl$_3$) δH: 10.06 (s, 1H), 8.15 (d, J=7.9 Hz, 1H), 8.05 (dd, J=9.0, 1.9 Hz, 1H), 7.89 (m, 4H), 7.53 (m, 1H), 7.36-7.16 (m, 4H), 4.45 (m, 4H), 4.33-4.21 (m, 6H), 2.16-1.90 (m, 11H), 1.71-1.39 (m, 24H), 1.06-0.93 (m, 15H) ppm. $^{13}$C NMR (100 MHz; CDCl$_3$) δC: 164.3, 161.8, 160.1, 160.1, 149.6, 149.1, 148.8, 148.4, 142.9, 140.3, 140.3, 130.6, 130.5, 129.6, 129.6, 127.3, 124.8, 123.7, 123.4, 123.4, 123.2, 123.2, 118.3, 118.1, 116.4, 114.6, 114.3, 110.9, 108.2, 106.8, 106.7, 103.9, 69.9, 69.8, 69.6, 69.0, 29.4, 29.3, 29.2, 28.6, 28.5, 28.4, 22.8, 14.3 ppm. 19F NMR (282 MHz; CDCl3) δF: −111.8 ppm. ES+MS m/z: 817.5 ([M+H$^+$Na]$^+$ 50%), 816.5 ([M+Na]$^+$ 100%), 794.5 ([M]+ 55%). IR λ−1 (neat): 2952 m (C—H), 2925 m (C—H), 2856 m (C—H), 1617 w (C=N), 1518 s (benzene ring), 1434 s (benzene ring), 1262 s (C—O), 1174 s (C—O) cm−1. Elemental analysis Found: C, 75.62; H, 8.25; N, 1.78%. C$_{50}$H$_{64}$FNO$_6$ requires C, 75.63; H, 8.12; N, 1.76%.

EXAMPLE 9—METHOD OF SYNTHESISING COMPOUND 9

Compound 9 was synthesised using the following method. A solution of 2-fluorobenzoic acid (41.86 mg; 0.26 mmol), palladium diacetate (0.005 mmol) and iodobenzene diacetate (0.157 mmol) in o-xylene (5 mL) was heated to 70° C. under N$_2$ for 20 min. A solution of Precursor 2 (100 mg, 0.131 mmol) in o-xylene (2 mL) was added and heated to 140° C. for 72 h. The mixture was cooled to room temperature and diluted with CH$_2$Cl$_2$ (20 mL). The mixture was washed with 1M NaOH (2×20 mL) and the organic phase was dried in vacuo. The crude black solid was purified by flash column chromatography (silica; 40% CH$_2$Cl$_2$: 60% n-hexane) to afford Compound 9 as a yellow solid (7 mg; 10%).

The name for Compound 9 is 8-(2-fluorophenyl)-2,3,6,11,12-pentakis(pentyloxy)triphenyleno[1,2-d]oxazole.

Compound 9 had the following characterisation data: $^1$H NMR (300 MHz; CDCl3) δH: 10.16 (s, 1H), 8.38 (m, 1H), 7.92 (m, 4H), 7.63-7.47 (m, 1H), 7.43-7.28 (m, 2H), 4.47 (m, 4H), 4.27 (m, 5H), 2.13-1.91 (m, 9H), 1.69-1.39 (m, 21H), 1.00 (m, 14H) ppm. 13C NMR (100 MHz; CDCl3) δC: 162.4, 159.8, 157.6, 157.5, 149.7, 149.3, 148.8, 148.4, 142.9, 140.6, 140.5, 139.9, 132.9, 132.8, 130.3, 127.3, 124.8, 124.5, 123.9, 123.4, 123.4, 117.4, 117.2, 116.7, 116.0, 115.9, 110.9, 108.3, 107.0, 106.9, 104.4, 69.8, 69.5, 68.9, 29.2, 29.0, 28.4, 28.3, 22.6, 22.6, 14.1 ppm. 19F NMR (282 MHz; CDCl3) δF: −109.1 ppm. MALDI+ m/z: 795.6 ([M+1+H]+ 20%), 794.6 ([M+H]+ 65%), 793.6 ([M]+ 100%). IR λ−1 (neat): 2952 m (C—H), 2925 m (C—H), 2856 m (C—H), 1617 w (C=N), 1518 m (benzene ring), 1434 m (benzene ring), 1261 s (C—O), 1176 s (C—O) cm−1. Elemental analysis Found: C, 75.92; H, 8.26; N, 1.74%. C$_{50}$H$_{64}$FNO$_6$ requires C, 75.63; H, 8.12; N, 1.76%.

EXAMPLE 10—METHOD OF SYNTHESISING COMPOUND 10

Compound 10 was synthesised using the following method. A slurry of Precursor 2 (100 mg; 0.01 mmol), iodobenzene diacetate (51 mg; 0.16 mmol) and palladium diacetate (1 mg; 0.005 mmol) in a mixture of PhMe (5 mL) and acetic acid (1 mL) in PhMe (5 mL) under an N$_2$ atmosphere was heated and held at reflux for 72 h. The reaction was then cooled to room temperature and washed with 1M NaOH (1M; 2×10 mL). The organic phase was evaporated to dryness in vacuo. The solid was then purified via flash column chromatography (60% n-hexane: 40% CH$_2$Cl$_2$) to afford Compound 10 as a white solid (64 mg; 66%).

The name for Compound 10 is 8-methyl-2,3,6,11,12-pentakis(pentyloxy)triphenyleno[1,2-d]oxazole.

Compound 10 had the following characterisation data: $^1$H NMR δH: (400 MHz, CDCl$_3$) 9.94 (1H, s), 7.94 (1H, s), 7.90 (1H, s), 7.89 (1H, s), 7.85 (1H, s), 4.42 (2H, t, J 6.7), 4.38 (2H, t, J 6.8), 4.30-4.24 (6H, m), 2.81 (3H, s), 1.99 (10H, m), 1.65-1.53 (10H, m), 1.52-1.44 (10H, m), 1.03-0.96 (15H, m) ppm. $^{13}$C NMR δC: (100 MHz, CDCl$_3$) 162.4, 149.9, 149.4, 149.1, 148.8, 143.2, 140.8, 140.2, 127.2, 125.0, 124.2, 123.9, 123.7, 116.7, 111.6, 108.8, 107.3, 107.2, 102.9, 70.3, 70.2, 69.88, 69.40, 29.60, 29.5, 29.3, 28.8, 28.8, 28.6, 23.0, 15.2, 14.5 ppm. MALDI m/z: 714.5 ([M]+ 100%).

EXAMPLE 11—METHOD OF SYNTHESISING COMPOUND 11

Compound 11 was synthesised using the following method. A solution of Precursor 2 (200 mg, 0.263 mmol) and trimethylamine (0.2 mL, 1.44 mmol) in PhMe (7 mL) was heated at reflux under N$_2$ for 10 min. 2-Thiophenecarbonyl chloride (0.3 mL, 2.62 mmol) was added and heated under reflux for 90 min. The solution was cooled to room temperature and washed with 1 M HCl (30 mL) and the organic phase extracted with EtOAc (2×30 mL). The organic phase was dried in vacuo and the resultant black solid was heated at 240° C. for 10 mins before being cooled to room temperature. The crude black solid was purified by flash column chromatography (silica; 40% CH$_2$Cl$_2$: 60% n-hexane) to afford Compound 11 as a yellow solid (136 mg; 64%).

The name for Compound 11 is 2,3,6,11,12-pentakis(pentyloxy)-8-(thiophen-2-yl)triphenyleno[1,2-d]oxazole.

Compound 11 had the following characterisation data: $^1$H NMR δH: (300 MHz, CDCl$_3$) 10.03 (1H, s), 7.99 (1H, dd, J 3.7, 1.2), 7.92 (1H, s), 7.89 (1H, s), 7.88 (1H, s), 7.88 (1H, s), 7.58 (1H, dd J 5.0, 1.2), 7.25-7.22 (1H, dd, J 5.0, 3.7), 4.48-4.43 (4H, m), 4.31-4.23 (6H, m), 2.14-1.93 (10H, m), 1.71-1.42 (20H, m), 1.04-0.97 (15H, m) ppm. $^{13}$C NMR δC: (100 MHz, CDCl$_3$) 157.8, 149.8, 149.4, 149.0, 148.6, 143.0, 140.7, 140.1, 130.6, 130.1, 129.7, 128.5, 127.5, 125.0, 124.1, 123.7, 123.6, 116.6, 111.1, 108.5, 107.1, 107.1, 104.0, 70.2, 70.2, 70.1, 69.8, 69.1, 29.6, 29.5, 29.4, 28.9, 28.8, 28.8, 28.6, 23.0, 23.0, 14.6, 14.5, 14.5 ppm. MALDI m/z: 781.5 ([M]+ 100%).

EXAMPLE 12—METHOD OF SYNTHESISING COMPOUND 12

Compound 12 was synthesised using the following method. A solution of Precursor 2 (100 mg, 0.132 mmol), 4-Cyanobenzoyl chloride (109 mg, 0.658 mmol) and N,N-Diisopropylethylamine (0.1 mL, 0.574 mmol) in PhMe (5 mL) was heated to and held at reflux for 18 h under N$_2$. The reaction was cooled to room temperature and then evaporated to dryness in vacuo. The solid was then heated and held at 240° C. for 15 mins under N$_2$. The crude black solid was then cooled to room temperature and purified via flash column chromatography (silica, 40% CH$_2$Cl$_2$: 60% n-hexane) to afford Compound 12 as a yellow solid (40 mg, 38%).

The name for Compound 12 is 4-(2,3,6,11,12-pentakis(pentyloxy)triphenyleno[1,2-d]oxazol-8-yl)benzonitrile.

Compound 12 had the following characterisation data: $^1$H NMR δH: (300 MHz, CDCl$_3$) 9.96 (1H, s), 8.43-8.40 (2H, d, J 8.55), 7.90 (1H, s), 7.89 (1H, s), 7.88 (1H, s), 7.87 (1H, s), 7.83-7.80 (2H, d, J 8.55), 4.43-4.38 (4H, m), 4.30-4.23 (6H, m), 2.12-1.93 (10H, m), 1.67-1.42 (20H, m), 1.04-0.97 (15H, m) ppm. $^{13}$C NMR δC: (100 MHz, CDCl$_3$) 159.3, 150.0, 149.3, 149.1, 148.8, 143.1, 140.6, 140.4, 132.7, 131.4, 127.8, 127.6, 125.0, 123.7, 123.7, 123.4, 118.7, 116.6, 114.4, 111.0, 108.4, 106.9, 106.7, 104.4, 70.2, 70.0, 69.9, 69.8, 69.2, 29.6, 29.5, 29.4, 28.8, 28.8, 28.8, 28.7, 23.0, 14.6, 14.5 ppm. MALDI m/z: 800.4 ([M]+ 100%).

EXAMPLE 13—METHOD OF SYNTHESISING COMPOUND 13

Compound 13 was synthesised using the following method. A solution of 4-(trifluoromethyl)benzoic acid carboxylic acid (248 mg, 1.31 mmol), palladium diacetate (0.005 mmol) and iodobenzene diacetate (0.157 mmol) in PhMe (5 mL) was heated at 60° C. under N$_2$ for 30 min. A solution of Precursor 2 (100 mg; 0.132 mmol) in PhMe (2 mL) was added and heated under reflux for 48-72 h, whilst stirring. The solution was cooled to room temperature and diluted with CH$_2$Cl$_2$ (20 mL). The organic phase was washed with aqueous NaOH (1M; 2×20 mL), separated and the organic phase was dried in vacuo. The crude black solid was purified by flash column chromatography (silica; 40% CH$_2$Cl$_2$: 60% n-hexane) to afford Compound 13 as a yellow solid (6 mg; 5%).

The name for Compound 13 is 2,3,6,11,12-pentakis(pentyloxy)-8-(4-(trifluoromethyl)phenyl)triphenyleno[1,2-d]oxazole.

Compound 13 had the following characterisation data: $^1$H NMR δH: (300 MHz, CDCl$_3$) 10.04 (1H, s), 8.48-8.46 (2H, d, J 8.50), 7.92 (1H, s), 7.90 (1H, s), 7.89 (1H, s), 7.88 (1H, s), 7.83-7.80 (2H, d, J 8.50), 4.47-4.45 (4H, t, J 6.74), 4.31-4.24 (6H, m), 2.14-1.94 (10H, m), 1.70-1.43 (20H, m), 1.05-0.98 (15H, m) ppm. $^{19}$F NMR δF: (300 MHz, CDC13) 62.9 (s) ppm. $^{13}$C NMR δC: (100 MHz, CDCl$_3$) 159.3, 150.0, 149.3, 149.1, 148.8, 143.1, 140.6, 140.4, 132.7, 131.4, 127.8, 127.6, 125.0, 123.7, 123.7, 123.4, 118.7, 116.6, 114.4, 111.0, 108.4, 106.9, 106.7, 104.4, 70.2, 70.0, 69.9, 69.8, 69.2, 29.6, 29.5, 29.4, 28.8, 28.8, 28.8, 28.7, 23.0, 14.6, 14.5 ppm. MALDI m/z: 844.5 ([M+H]+ 100%).

EXAMPLE 14—METHOD OF SYNTHESISING COMPOUND 14

Compound 14 was synthesised using the following method. A solution of Precursor 2 (100 mg, 0.132 mmol), 2-iodobenzoyl chloride (175 mg, 0.658 mmol) and N,N-Diisopropylethylamine (0.1 mL, 0.574 mmol) in PhMe (5 mL) was heated to and held at reflux for 18 h under N$_2$. The reaction was cooled to room temperature and then evaporated to dryness in vacuo. The solid was then heated and held at 240° C. for 15 mins under N$_2$. The crude black solid was then cooled to room temperature and purified via flash column chromatography (silica, 40% CH$_2$Cl$_2$: 60% n-hexane) to afford Compound 14 as a yellow solid (39.9 mg, 35%).

The name for Compound 14 is 8-(2-iodophenyl)-2,3,6,11,12-pentakis(pentyloxy)triphenyleno[1,2-d]oxazole.

Compound 14 had the following characterisation data: $^1$H NMR δH: (300 MHz, CDCl$_3$) 10.07 (1H, s), 8.20-8.16 (1H, dd, J 7.90, 1.60), 8.18-8.15 (1H, dd, J 7.90, 1.25), 7.95 (1H, s), 7.94 (1H, s), 7.91 (2H, m), 7.58-7.53 (1H, td, J 7.66, 7.63, 1.25), 7.26-7.20 (1H, td, J 7.66, 7.63, 1.60), 4.52-4.44 (4H, m), 4.31-4.25 (6H, m), 2.06-1.94 (10H, m), 1.67-1.41 (20H, m), 1.03-0.92 (15H, m) ppm. $^{13}$C NMR δC: (100 MHz, CDCl$_3$) 160.9, 149.9, 149.6, 149.2, 149.1, 143.3, 142.0, 140.6, 140.4, 132.5, 132.1, 132.1, 128.5, 127.6, 125.1, 124.1, 124.0, 123.7, 117.2, 111.9, 108.6, 107.3, 107.1, 104.9, 95.0, 70.4, 70.2, 70.2, 70.1, 69.9, 29.6, 29.6, 29.5, 29.5, 28.9, 28.8, 28.7, 23.0, 23.0, 14.5 ppm. MALDI m/z: 901.6 ([M]+ 14%)

EXAMPLE 15—METHOD OF SYNTHESISING COMPOUND 15

Compound 15 was synthesised using the following method. A solution of Precursor 2 (100 mg, 0.132 mmol), 2-chlorobenzoyl chloride (175 mg, 0.658 mmol) and N,N-Diisopropylethylamine (0.1 mL, 0.574 mmol) in PhMe (5 mL) was heated to and held at reflux for 18 h under N$_2$. The reaction was cooled to room temperature and then evaporated to dryness in vacuo. The solid was then heated and held at 240° C. for 15 mins under N$_2$.

The crude black solid was then cooled to room temperature and purified via flash column chromatography (silica, 40% CH$_2$Cl$_2$: 60% n-hexane) to afford Compound 15 as a yellow solid (52.4 mg, 49%).

The name for Compound 15 is 8-(2-chlorophenyl)-2,3,6,11,12-pentakis(pentyloxy)triphenyleno[1,2-d]oxazole.

Compound 15 had the following characterisation data: $^1$H NMR δH: (300 MHz, CDCl$_3$) 10.06 (1H, s), 8.39-8.34 (1H, m), 7.92-7.90 (4H, m), 7.66 (1H, m), 7.51-7.44 (2H, m), 4.49-4.41 (4H, m), 4.30-4.25 (6H, m), 2.06-1.95 (10H, m), 1.67-1.43 (20H, m), 1.03-0.92 (15H, m) ppm. $^{13}$C NMR δC: (100 MHz, CDCl$_3$) 158.8, 149.6, 149.4, 148.9, 148.5, 142.9, 140.4, 139.9, 133.5, 131.7, 131.6, 127.3, 127.0, 126.2, 124.8, 123.9, 123.4, 116.8, 110.9, 108.2, 106.9, 104.6, 70.1, 70.0, 69.9, 69.6, 69.1, 29.8, 29.3, 29.3, 29.2, 28.5, 28.4, 22.7, 14.3 ppm. MALDI m/z: 809.7 ([M]$^+$ 95%)

EXAMPLE 16—METHOD OF SYNTHESISING COMPOUND 16

Compound 16 was synthesised using the following method. A solution of Precursor 2 (100 mg, 0.132 mmol), 2-bromobenzoyl chloride (144 mg, 0.658 mmol) and N,N-Diisopropylethylamine (0.1 mL, 0.574 mmol) in PhMe (5 mL) was heated to and held at reflux for 18 h under N$_2$. The reaction was cooled to room temperature and then evaporated to dryness in vacuo. The solid was then heated and held at 240° C. for 15 mins under N$_2$. The crude black solid was then cooled to room temperature and purified via flash column chromatography (silica, 40% CH$_2$Cl$_2$: 60% n-hexane) to afford Compound 16 as a yellow solid (25.8 mg, 21%).

The name for Compound 16 is 8-(2-bromophenyl)-2,3,6,11,12-pentakis(pentyloxy)triphenyleno[1,2-d]oxazole.

Compound 16 had the following characterisation data: $^1$H NMR δH: (300 MHz, CDCl$_3$) 10.03 (1H, s), 8.31-8.28 (1H, dd, J 7.91, 1.75), 7.91-7.89 (4H, m), 7.86-7.83 (1H, dd, J 7.91, 1.23), 7.54-7.49 (1H, td, J 7.70, 7.60, 1.23), 7.42-7.37 (1H, td, J 7.70, 7.57, 1.75) 4.49-4.39 (4H, m), 4.31-4.23 (6H, m), 2.06-1.95 (10H, m), 1.64-1.43 (20H, m), 1.03-0.95 (15H, m) ppm. $^{13}$C NMR δC: (100 MHz, CDCl$_3$): 159.5, 149.7, 149.4, 148.9, 148.6, 142.9, 140.3, 135.0, 132.2, 131.8, 128.3, 127.6, 127.4, 124.8, 123.9, 123.6, 123.5, 122.0, 116.9, 111.1, 108.2, 107.0, 104.7, 70.1, 70.0, 69.9, 69.6, 69.4, 29.3, 29.3, 29.2, 28.6, 28.5, 28.4, 22.7, 14.3 ppm. MALDI m/z: 855.7 ([M]+ 31%)

EXAMPLE 17—METHOD OF SYNTHESISING COMPOUND 17

Compound 17 was synthesised using the following method. A solution of 5-bromovaleric acid (773 mg, 4.27 mmol), palladium diacetate (0.005 mmol) and iodobenzene diacetate (0.512 mmol) in PhMe (10 mL) was heated at 70° C. under $N_2$ for 20 min. A solution of Precursor 2 (325 mg; 0.428 mmol) in PhMe (10 mL) was added and heated under reflux for 48-72 h, whilst stirring. The solution was cooled to room temperature and diluted with $CH_2Cl_2$ (20 mL). The organic phase was washed with aqueous NaOH (1M; 2×20 mL), separated and the organic phase was dried in vacuo. The crude black solid was purified by flash column chromatography (silica; 40% $CH_2Cl_2$: 60% n-hexane) to afford Compound 17 as a white solid (109 mg; 31%).

The name for Compound 17 is 8-(4-bromobutyl)-2,3,6,11,12-pentakis(pentyloxy)triphenyleno[1,2-d]oxazole.

Compound 17 had the following characterisation data: $^1$H NMR δH: (300 MHz, CDCl$_3$) 9.95 (1H, s), 7.92 (1H, s), 7.90 (1H, s), 7.89 (1H, s), 7.84 (1H, s), 4.43-4.34 (4H, m), 4.30-4.24 (6H, m), 3.55-3.50 (2H, t, J 6.29), 3.15-3.10 (2H, t, J 7.05), 2.35 (3H, s), 2.25-1.94 (12H, m), 1.64-1.45 (24H, m), 1.03-0.97 (15H, m) ppm. $^{13}$C NMR δC: (100 MHz, CDCl$_3$) 164.6, 149.6, 149.1, 148.8, 148.4, 142.9, 140.1, 139.7, 127.0, 124.7, 123.8, 123.5, 123.4, 116.3, 111.0, 108.4, 107.0, 102.7, 70.0, 69.9, 69.6, 69.6, 68.9, 33.0, 31.9, 29.3, 29.2, 29.2, 29.1, 28.6, 28.5, 28.4, 28.3, 22.7, 25.3, 22.7, 22.6, 14.2, 14.2, 14.1 ppm. ES+ m/z: 834.4 ([M+H]+ 95%), 836.4 ([M+H]+ 100%).

EXAMPLE 18—METHOD OF SYNTHESISING COMPOUND 18

Compound 18 was synthesised using the following method. A solution of Compound 17 (66 mg, 0.079 mmol) in acetone (10 mL) was heated to 50° C. and stirred under $N_2$, to this was added a solution of sodium azide (7 mg, 0.111 mmol) in water (5 mL) and left stirring under $N_2$ for 4 h. After this time a precipitate had formed and the solvent was removed under reduced pressure, the precipitate was then filtered under vacumm and dried to give Compound 18 as an off white solid (59 mg, 94%)

The name for Compound 18 is 8-(4-azidobutyl)-2,3,6,11,12-pentakis(pentyloxy)triphenyleno[1,2-d]oxazole.

Compound 18 had the following characterisation data: $^1$H NMR δH: (300 MHz, CDCl$_3$) 9.96 (1H, s), 7.94 (1H, s), 7.90 (1H, s), 7.90 (1H, s), 7.87 (1H, s), 4.45-4.40 (2H, t, J 6.70), 4.39-4.35 (2H, t, J 6.67), 4.30-4.24 (6H, m), 3.55-3.51 (2H, t, J 6.31), 3.17-3.12 (2H, t, J 7.11), 2.28-1.93 (12H, m), 1.65-1.41 (24H, m), 1.03-0.97 (15H, m) ppm. $^{13}$C NMR δC: (100 MHz, CDCl$_3$) 165.0, 149.6, 149.9, 149.4, 149.1, 148.7, 143.2, 140.4, 140.0, 127.3, 125.0, 124.1, 123.8, 123.7, 116.7, 111.3, 108.7, 107.3, 103.0, 70.3, 70.3, 69.9, 69.9, 69.2, 33.3, 32.3, 29.6, 29.5, 29.5, 29.4, 28.9, 28.8, 28.7, 28.6, 28.0, 25.6, 23.0, 23.0, 14.6, 14.5, 14.5 ppm. ES+ m/z: 819.5 ([M+Na]+ 100%).

EXAMPLE 19—METHOD OF SYNTHESISING COMPOUND 19

Compound 19 was synthesised using the following method. Compound 17 (21 mg, 0.025 mmol) was dissolved in anhydrous THF (4 mL) to this mixture potassium thioacetate (12 mg, 0.1 mmol) was added and stirred under $N_2$ for 6 h. The organic phase was then extracted with DCM (10 mL) and washed with water (2×10 mL). The organic phase was then dried in vacuo and the solid recrystalised with DCM:methanol (1 mL:5 mL). The resultant precipitate was filtered under suction and the solid washed with methanol to give Compound 19 as an off white solid (4 mg, 19%)

The name for Compound 19 is S-(4-(2,3,6,11,12-pentakis (pentyloxy)triphenyleno[1,2-d]oxazol-8-yl)butyl) ethanethioate.

Compound 19 had the following characterisation data: $^1$H NMR δH: (300 MHz, CDCl$_3$) 9.97 (1H, s), 7.94 (1H, s), 7.90 (1H, s), 7.89 (1H, s), 7.86 (1H, s), 4.45-4.35 (4H, m), 4.30-4.24 (6H, m), 3.14-3.09 (2H, t, J 7.44), 3.02-2.97 (2H, t, J 7.21), 2.35 (3H, s), 2.18-1.80 (12H, m), 1.65-1.42 (24H, m), 1.03-0.97 (15H, m) ppm. $^{13}$C NMR δC: (100 MHz, CDCl$_3$) 196.0, 165.2, 149.9, 149.4, 149.1, 148.7, 143.2, 140.4, 140.0, 127.2, 125.0, 124.2, 123.8, 123.6, 116.7, 111.4, 108.7, 107.3, 103.1, 70.3, 70.2, 69.9, 69.9, 69.2, 31.0, 30.1, 29.6, 29.5, 29.5, 29.4, 29.4, 29.1, 28.9, 28.8, 28.7, 28.6, 28.5, 26.2, 23.0, 23.0, 14.6, 14.5, 14.5, 14.5 ppm. MALDI m/z: 829.5 ([M]+ 100%).

EXAMPLE 20—METHOD OF SYNTHESISING COMPOUND 20

Compound 22 was synthesised using the following method. A solution of Compound 17 (260 mg, 0.311 mmol), Sodium Tert-butoxide (90 mg, 0.934 mmol), Potassium Iodide (40 mg, 0.311 mmol) and Ethylene Glycol (193 mg, 3.11 mmol) in MeCN (15 mL) was heated to and held at reflux for 48 h under $N_2$. The reaction was cooled to room temperature and then evaporated to dryness in vacuo. The crude solid was dissolved with $CH_2Cl_2$ (20 mL). The organic phase was washed with aqueous NaOH (1M; 2×20 mL) and then HCl (1M, 2×20 mL), separated and the organic phase was dried in vacuo. The crude black solid was then cooled to room temperature and purified via flash column chromatography (silica, 40% $CH_2Cl_2$: 60% n-hexane) to afford Compound 16 as a yellow solid (84 mg, 36%).

The name for Compound 20 is 8-(but-3-en-1-yl)-2,3,6,11,12-pentakis(pentyloxy)triphenyleno[1,2-d]oxazole.

Compound 20 had the following characterisation data: $^1$H NMR δH: (300 MHz, CDCl$_3$) 10.00 (1H, s), 7.92 (1H, s), 7.90 (1H, s), 7.89 (1H, s), 7.84 (1H, s), 6.14-6.00 (1H, ddt, J 16.95, 10.20, 6.45), 5.22 (1H, dd, J 16.95, 1.60), 5.10 (1H, dd, J 10.20, 1.60), 4.43-4.35 (4H, m), 4.30-4.24 (6H, m), 3.22-3.17 (2H, t, J 7.55), 3.17-3.12 (2H, t, J 7.11), 2.86-2.78 (2H, m), 2.08-1.94 (10H, m), 1.62-1.45 (20H, m), 1.03-0.97 (15H, m) ppm. $^{13}$C NMR δC: (100 MHz, CDCl$_3$) 165.0, 149.8, 149.4, 149.1, 148.7, 143.2, 140.4, 140.0, 137.0, 127.2, 125.0, 124.2, 123.8, 123.6, 116.7, 116.3, 111.4, 108.7, 107.3, 107.2, 103.0, 70.3, 70.2, 69.9, 69.9, 69.2, 30.9, 29.6, 29.5, 29.5, 29.3, 28.8, 28.8, 28.7, 28.6, 28.5, 23.0, 22.9, 14.5, 14.5, 14.5 ppm. ES+ m/z: 754.5 ([M+H]+ 100%).

EXAMPLE 21—METHOD OF SYNTHESISING COMPOUND 21

Compound 21 was synthesised using the following method. A solution of decanoic acid (0.132 mg, 0.236 mmol), palladium diacetate (0.005 mmol) and iodobenzene didecanoate (0.235 mmol) in PhMe (10 mL) was heated at 70° C. under $N_2$ for 20 min. A solution of Precursor 2 (100 mg; 0.132 mmol) in PhMe (10 mL) was added and heated under reflux for 48-72 h, whilst stirring. The solution was cooled to room temperature and diluted with $CH_2Cl_2$ (20 mL). The organic phase was washed with aqueous NaOH (1M; 2×20 mL), separated and the organic phase was dried in vacuo. The crude black solid was purified by flash column chromatography (silica; 40% $CH_2Cl_2$: 60% n-hexane) to afford Compound 21 as a white solid (42 mg; 39%).

The name for Compound 21 is 8-nonyl-2,3,6,11,12-pentakis(pentyloxy)triphenyleno[1,2-d]oxazole.

Compound 21 had the following characterisation data: $^1$H NMR δH: (300 MHz, $CDCl_3$) 10.02 (1H, s), 7.93 (1H, s), 7.90 (1H, s), 7.89 (1H, s), 7.84 (1H, s), 4.43-4.36 (4H, m), 4.30-4.24 (6H, m), 3.11-3.06 (2H, t, J 7.52), 2.10-1.94 (12H, m), 1.63-1.29 (32H, m), 1.02-0.97 (15H, m) 0.91-0.87 (3H, m) ppm. $^{13}$C NMR δC: (100 MHz, $CDCl_3$) 165.9, 149.8, 149.3, 149.0, 148.6, 143.2, 140.4, 140.1, 127.1, 124.9, 124.2, 123.8, 123.6, 123.6, 116.6, 111.3, 108.6, 107.2, 107.1, 102.9, 70.2, 69.9, 69.8, 69.1, 32.3, 29.9, 29.8, 29.7, 29.6, 29.5, 29.4, 29.0 28.9, 28.8, 28.6, 27.1 23.1, 23.0, 14.5, 14.5 ppm. ES+ m/z: 826.6 ([M+H]+ 100%).

EXAMPLE 22—METHOD OF SYNTHESISING COMPOUND 22

Compound 22 was synthesised using the following method. A solution of Precursor 2 (100 mg, 0.132 mmol), 4-(dimethylamino)benzoyl chloride (175 mg, 0.658 mmol) and N,N-Diisopropylethylamine (0.1 mL, 0.574 mmol) in PhMe (5 mL) was heated to and held at reflux for 18 h under $N_2$. The reaction was cooled to room temperature and then evaporated to dryness in vacuo. The solid was then heated and held at 240° C. for 15 mins under $N_2$. The crude black solid was then cooled to room temperature and purified via flash column chromatography (silica, 40% $CH_2Cl_2$: 60% n-hexane) to afford Compound 22 as a yellow solid (19 mg, 18%).

The name for Compound 22 is N,N-dimethyl-4-(2,3,6,11,12-pentakis(pentyloxy)triphenyleno[1,2-d]oxazol-8-yl)aniline.

Compound 22 had the following characterisation data: $^1$H NMR δH: (300 MHz, $CDCl_3$) 10.20 (1H, s), 8.27-8.24 (2H, d, J 8.60), 7.94 (1H, s), 7.90-7.85 (3H, m), 6.89-6.86 (2H, d, J 8.60), 4.56-4.45 (4H, m), 4.31-4.24 (6H, m), 3.11 (6H, s), 2.16-1.94 (10H, m), 1.71-1.42 (20H, m), 1.04-0.97 (15H, m) ppm. $^{13}$C NMR δC: (100 MHz, $CDCl_3$) 162.8, 152.2, 149.7, 149.3, 148.5, 143.1, 141.4, 140.2, 129.3, 127.4, 124.9, 124.5, 124.0, 123.6, 116.5, 112.4, 111.5, 108.6, 107.3, 107.2, 103.4, 70.2, 70.2, 69.9, 69.2, 40.9, 29.6, 29.6, 29.5, 29.4, 29.0, 28.8, 28.8, 28.7, 23.0, 23.0, 14.7, 14.5 ppm. ES+ m/z: 819.7 ([M]+ 100%).

EXAMPLE 23—METHOD OF SYNTHESISING COMPOUND 23

Compound 23 was synthesised using the following method. A solution of 4-nitrobenzoic acid (1 g, 6 mmol), palladium diacetate (0.005 mmol) and (diacetoxyiodo)benzene (51 mg, 0.157 mmol) in PhMe (10 mL) was heated at 70° C. under $N_2$ for 20 min. A solution of Precursor 2 (100 mg; 0.132 mmol) in PhMe (10 mL) was added and heated under reflux for 48-72 h, whilst stirring. The solution was cooled to room temperature and diluted with $CH_2Cl_2$ (20 mL). The organic phase was washed with aqueous NaOH (1M; 2×20 mL), separated and the organic phase was dried in vacuo. The crude black solid was purified by flash column chromatography (silica; 40% $CH_2Cl_2$: 60% n-hexane) to afford Compound 23 as an off-white solid (74 mg; 69%).

The name for Compound 23 is 8-(4-nitrophenyl)-2,3,6,11,12-pentakis(pentyloxy)triphenyleno[1,2-d]oxazole.

Compound 23 had the following characterisation data: $^1$H NMR δH: (300 MHz, $CDCl_3$) 9.66 (1H, s), 8.14-8.05 (4H, m), 7.74 (1H, s), 7.73 (1H, s), 7.70 (1H, s), 7.67 (1H, s), 4.30-4.19 (10H, m), 2.04-1.94 (10H, m), 1.63-1.47 (20H, m), 1.05-1.00 (15H, m) ppm. $^{13}$C NMR δC: (100 MHz, $CDCl_3$) 158.9, 150.0, 149.3, 149.1, 148.8, 143.0, 140.6, 140.4, 132.8, 127.8, 127.5, 125.0, 124.0, 123.6, 123.5, 123.3, 116.5, 110.8, 108.3, 106.8, 106.4, 104.3, 70.2, 69.9, 69.8, 69.7, 69.1, 29.6, 29.6, 29.5, 29.4, 28.9, 28.8, 28.8, 28.7, 23.0, 14.6, 14.5 ppm. MALDI m/z: 820.5 ([M]+ 100%).

EXAMPLE 24—METHOD OF SYNTHESISING COMPOUND 24

Compound 24 was synthesised using the following method. A solution of (diacetoxyiodo)benzene (51 mg, 0.157 mmol) and acetylsalicylic acid (550 mg, 3.031 mmol) in toluene (4 mL) was heated to 80° C. and stirred for 10 mins under $N_2$. Then Precursor 2 (100 mg, 0.131 mmol) was added to form a black solution which was then stirred for a further 10 mins. A solution of palladium diacetate (1 mg, 5 mol %) and acetylsalicylic acid (553 mg, 3.197 mmol) in toluene (4 mL) was heated to 110° C. and stirred for 10 mins under $N_2$ before being combined with the black solution. The resultant solution was left stirring at 110° C. for 72 h under $N_2$. The crude black solution was dried in vaccuo and purified by flash column chromatography (silica; 40% $CH_2Cl_2$: 60% n-hexane). The crude material was then evaporated to dryness in vacuo and then dissolved in a mixture of MeCN (10 mL) and 1M NaOH (10 mL). The solution was heated to 80° C. for 2 h. After cooling to room temperature the product was acidified using 1M HCl (20 mL) and extracted into $CH_2Cl_2$ (3×10 mL). The combined organic layer was evaporated to dryness in vacuo to afford Compound 24 as a white solid (2 mg. 2%)

The name for Compound 24 is 2-(2,3,6,11,12-pentakis(pentyloxy)triphenyleno[1,2-d]oxazol-8-yl)phenol.

Compound 24 had the following characterisation data: $^1$H NMR δH: (300 MHz, $CDCl_3$) 11.42 (1H, s), 9.35 (1H, s), 8.20-8.17 (1H, dd, J 8.01, 1.67), 7.90 (1H, s), 7.89 (1H, s), 7.88 (1H, s), 7.87 (1H, s), 7.52-7.46 (1H, ddd, J 8.51, 7.22, 1.67), 7.18-7.14 (1H, dd, J 8.51, 1.08), 7.08-7.05 (1H, ddd, J 8.01, 7.22, 1.08), 4.47-4.42 (2H, t, J 6.65), 4.39-4.35 (2H, t, J 6.71), 4.30-4.19 (6H, m), 2.09-1.94 (10H, m), 1.71-1.43 (20H, m), 1.05-0.98 (15H, m) ppm. MALDI m/z: 791 ([M]+ 100%).

EXAMPLE 25—METHOD OF SYNTHESISING COMPOUND 25

Compound 25 was synthesised using the following method.

Precursor 3 was synthesised using the following method. A solution of 2,3,6,7,10,11-hexabutoxy-1-nitrotriphenylene (1.70 g, 2.79 mmol), Sodium borohydride (1.70 g, 45.1. mmol) and Nickel(II) chloride hexahydrate (4.45 g, 18.7 mmol) in a 50/50 mix of MeO and THF (40 mL) was stirred at room temperature for 5 h under $N_2$. The crude black solid was then filtered and washed with $CHCl_3$ and the filtrate evaporated to dryness in vacuo to afford Precursor 3 as a brown solid (1.6 g, 85%).

The name for Precursor 3 is 2,3,6,7,10,11-hexabutoxytriphenylen-1-amine

Precursor 3 had the following characterization data: $^1$H NMR δH: (300 MHz, $CDCl_3$) 8.82 (1H, s), 7.83 (1H, s), 7.80 (1H, s), 7.78 (1H, s), 7.37 (1H, s), 4.57 (2H, s), 4.29-4.09 (12H, m), 2.01-1.81 (12H, m), 1.67-1.52 (12H, m), 1.13-

0.94 (18H, m) ppm. $^{13}$C NMR δC: (100 MHz, CDCl$_3$) 151.0, 149.5, 148.9, 148.0, 147.6, 138.4, 135.6, 127.0, 124.7, 124.5, 124.1, 124.0, 114.0, 110.3, 108.5, 108.2, 107.1, 97.4, 72.9, 69.7, 69.4, 69.1, 68.4, 32.7, 31.7, 31.7, 31.6, 31.6, 19.6, 19.6, 19.5, 19.5, 14.1 ppm. MALDI m/z: 675.8 ([M]+ 100%).

A solution of Precursor 3 (100 mg, 0.148 mmol), 2-napthoyl chloride (141 mg, 0.658 mmol) and N,N-Diisopropylethylamine (0.1 mL, 0.574 mmol) in PhMe (5 mL) was heated to and held at reflux for 18 h under N$_2$. The reaction was cooled to room temperature and then evaporated to dryness in vacuo. The solid was then heated and held at 240° C. for 15 mins under N$_2$. The crude black solid was then cooled to room temperature and purified via flash column chromatography (silica, 40% CH$_2$Cl$_2$: 60% n-hexane) to afford Compound 25 as a yellow solid (21 mg, 19%).

The name for Compound 25 is 2,3,6,11,12-pentabutoxy-8-(naphthalen-2-yl)triphenyleno[1,2-d]oxazole.

Compound 25 had the following characterisation data: $^1$H NMR δH: (300 MHz, CDCl$_3$) 10.01 (1H, s), 8.68 (1H, s), 8.31-8.27 (1H, dd, J 8.57, 1.65), 7.96-7.87 (3H, m), 7.80-7.79 (3H, m), 7.70 (1H, s), 7.58-7.55 (2H, m), 4.45-4.40 (2H, t, J7.01), 4.38-4.34 (2H, t, J6.67), 4.28-4.19 (6H, m), 2.15-1.91 (10H, m), 1.79-1.59 (10H, m), 1.18-1.07 (15H, m) ppm. $^{13}$C NMR δC: (100 MHz, CDCl$_3$) 161.6, 149.7, 149.3, 149.0, 148.5, 143.1, 140.8, 140.4, 134.9, 133.4, 129.2, 128.3, 127.8, 127.3, 127.1, 125.0, 124.9, 124.4, 124.1, 123.7, 123.6, 116.6, 111.3, 108.4, 107.1, 106.9, 103.7, 69.8, 69.6, 69.5, 68.9, 31.9, 31.9, 19.9, 19.8, 19.8, 14.5, 14.4, 14.4 ppm. MALDI m/z: 755.1 ([M]+ 100%).

EXAMPLE 26—METHOD OF SYNTHESISING COMPOUND 26

Compound 26 was synthesised using the following method. A solution of Precursor 4 (135 mg, 0.174 mmol) and palladium diacetate (0.0005 mmol) in PhMe (7 mL) was heated at reflux under N$_2$ for 10 min. 2-flourobenzoyl chloride (0.02 mL, 0.174 mmol) was added and heated under reflux for 40 h. The solution was cooled to room temperature and dried in vacuo and the resultant black solid was heated at 240° C. for 10 minutes before being cooled to room temperature. The crude black solid was purified by flash column chromatography (silica; 40% CH$_2$Cl$_2$: 60% n-hexane) to afford Compound 26 as an off-white solid (6 mg; 4%).

The name for Compound 26 is 2,9-bis(2-fluorophenyl)-4,7,12,13-tetrakis(pentyloxy)triphenyleno[1,2-d:8,7-d']bis(oxazole).

Compound 26 had the following characterisation data: $^1$H NMR δH: (300 MHz, CDCl$_3$) 10.09 (2H, s), 8.38-8.32 (2H, td, J 7.56, 7.52, 1.78), 7.82 (2H, m), 7.58 (2H, m), 7.36-7.31 (2H, m), 7.29-7.25 (2H, m), 4.48-4.39 (8H, m), 2.16-1.96 (8H, m), 1.70-1.44 (16H, m), 1.05-1.00 (12H, m) ppm. $^{19}$F NMR δF: (300 MHz, CDCl$_3$) 108.9 (s) ppm. MALDI m/z: 842.5 ([M]+ 100%).

EXAMPLE 27—METHOD OF SYNTHESISING COMPOUND 27

Compound 27 was synthesised using the following method. A solution of 4'-Carboxybenzo-15-crown-5 (600 mg, 1.92 mmol), Oxalyl chloride (2.0 mL, 23.6 mmol) and Dimethylformamide (0.01 ml, 0.129 mmol) was heated and held at reflux for 10 minutes under N$_2$. The reaction was cooled to room temperature and then evaporated to dryness in vacuo. A solution of Precursor 2 (100 mg, 0.132 mmol) and N,N-Diisopropylethylamine (0.1 mL, 0.574 mmol) in PhMe (5 mL) was added. The reaction was then heated and held at reflux for 72 h under N$_2$. The reaction was cooled to room temperature and then evaporated to dryness in vacuo. The solid was then heated and held at 240° C. for 15 mins under N$_2$. The crude black solid was then cooled to room temperature and purified via flash column chromatography (silica, 10% EtOAc: 90% n-hexane) to afford compound 27 as a brown solid (22 mg, 17%).

The name for Compound 27 is 8-(2,3,5,6,8,9,11,12-octahydrobenzo[b][1,4,7,10,13]pentaoxacyclopentadecin-15-yl)-2,3,6,11,12-pentakis(pentyloxy)triphenyleno[1,2-d]oxazole.

Compound 27 had the following characterisation data: $^1$H NMR δH: (300 MHz, CDCl$_3$) 10.10 (1H, s), 8.04-7.80 (6H, m), 6.99 (1H, d, J 8.35), 4.53-4.38 (4H, m), 4.33-4.17 (10H, m), 4.06-3.90 (4H, m), 3.89-3.73 (8H, m), 2.10-1.88 (10H, m), 1.69-1.44 (20H, m), 1.07-0.92 (15H, m) ppm. $^{13}$C NMR δC: (100 MHz, CDCl$_3$) 161.6, 152.1, 149.6, 149.1, 148.9, 148.4, 142.9, 140.7, 140.1, 127.2, 124.7, 124.0, 123.6, 123.4, 121.7, 120.5, 116.4, 113.2, 112.9, 111.1, 108.3, 107.0, 103.4, 71.3, 70.6, 70.5, 70.0, 70.0, 69.9, 69.6, 69.5, 69.2, 68.9, 68.7, 29.8, 29.4, 29.3, 29.3, 28.7, 28.5, 28.4, 22.8, 22.7, 14.3, 14.3 ppm. MALDI m/z: 965.9 ([M]+ 100%).

EXAMPLE 28—METHOD OF SYNTHESISING COMPOUND 28

Compound 28 was synthesised using the following method. A solution of Compound 2 (60 mg, 0.077 mmol) in degassed dichloromethane (5 mL) was stirred in a nitrogen purged 2 neck flask under nitrogen atmosphere at −20° C. Boron tribromide (1M solution in dichloromethane, 387 μL, 0.385 mmol, 5 eq) was added via syringe through a Suba-Seal® and the dark yellow solution was stirred for at room temperature for 24 h. Water (40 mL) was added to quench the reaction and the product was extracted with dichloromethane (10 mL), washed with water (2×20 mL) and dried over MgSO$_4$. The organic phase was evaporated to dryness and purified by column chromatography (Silica: 5% Ethyl acetate:Hexane) to afford Compound 28 as a brown solid (10 mg, 6%).

The name for Compound 28 is 2,3,11,12-tetrakis(pentyloxy)-8-phenyltriphenyleno[1,2-d]oxazol-6-ol.

Compound 28 had the following characterisation data: $^1$H NMR (300 MHz, CDCl$_3$) δH: 10.09 (1H, s), 8.48 (2H, dd, J 6.86, 2.85 Hz), 7.94 (1H, s), 7.90 (1H, s), 7.88 (1H, s), 7.83 (1H, s), 7.59-7.56 (3H, m), 5.95 (1H, s br), 4.48 (2H, t, J 6.60 Hz), 4.33 (2H, t, J 6.51 Hz), 4.26-4.24 (4H, m), 2.06-1.93 (8H, m), 1.64-1.43 (16H, m), 1.01-0.97 (12H, m) ppm. ES$^+$MS m/z: 728.39 ([M+Na]$^+$ 25%), 707.41 ([M+H+1]$^+$ 30%), 706.41 ([M+H]$^+$ 85%).

EXAMPLE 29—METHOD OF SYNTHESISING COMPOUND 29

Compound 29 was synthesised using the following method. Compound 2 (250 mg, 0.322 mmol) was disolved in dry dichloromethane (10 mL) and stired at 0° C. under a nirtogen atmosphere. 0.01M solution of Br$_2$ in dichloromethane (144 mL, 1.449 mmol) was then added over 2 hours (4×36 mL) and monitered by TLC. The reaction was quenched by addition of saturated sodium metabisulfate solution (100 mL). The product was extracted with dichloromethane (30 mL) washed with water (3×30 mL), dried over MgSO$_4$ and evaporated to dryness. The crude product was then purified by column chromatography (Silica 40% dichloromethane:hexane) to yield Compound 29 as a yellow solid (170 mg, 62%).

The name for Compound 29 is 1-bromo-2,3,6,11,12-pentakis(pentyloxy)-8-phenyltriphenyleno[1,2-d]oxazole.

Compound 29 had the following characterisaton data: $^1$H NMR (300 MHz, CDCl$_3$) δH: 10.06 (1H, s), 8.71 (1H, s), 8.56 (1H, s), 8.34-8.31 (2H, m), 7.60-7.58 (4H, m), 4.59 (2H, t J 6.5 Hz), 4.41 (2H, t J 6.8 Hz), 4.26-4.20 (6H, m), 2.06-1.90 (10H, m), 1.64-1.42 (20H, m), 1.02-0.94 (15H, m) ppm.

EXAMPLE 30—METHOD OF SYNTHESISING COMPOUND 30

Compound 30 was synthesised using the following method. Compound 29 (170 mg, 0.199 mmol), K$_2$CO$_3$ (410 mg, 2.97 mmol) and Pd(PPh$_3$)$_4$ (30 mg, 0.026 mmol) were dissolved in degassed 5:1 tertahydrofuran:Water mix (4 mL) under nitrogen atmosphere. (4-hydroxyphenyl)boronic acid (140 mg, 1.02 mmol) was then added and the reaction was heated to reflux under N$_2$ for 24 h. The product was extracted with dichloromethane (30 mL), washed with water (3×30 mL) and evaporated to dryness. The crude product was purified by column cromatography (Silica DCM:Hexane) to yield impure Compound 30 as a brown solid.

The name for Compound 30 is 4-(2,3,6,11,12-pentakis(pentyloxy)-8-phenyltriphenyleno[1,2-d]oxazol-1-yl)phenol.

Compound 30 had the following characterisation data: TOF LD$^+$ m/z: 869.49 ([M+1]$^{+\ 70}$%), 868.52 ([M]$^+$ 70%).

EXAMPLE 31—METHOD OF SYNTHESISING COMPOUND 31

Compound 31 was synthesised using the following method. Compound 10 (50.7 mg, 0.071 mmol) was added to a 2 neck round bottom flask, which was purged with nitrogen for 15 minutes. Dry dichloromethane (20 mL) was then added via syringe through a Suba-Seal® and the brown stirring solution was cooled to −78° C. Boron tribromide (1M solution in dichloromethane, 391 μL, 0.391 mmol, 5.5 equivalents) was added via syringe through a Suba-Seal® and the reaction was stirred for 4 h. The reaction mixture was poured over crushed ice and stirred until the ice had fully melted, 4 drops of hydrochloric acid (1M) were added and the product was extracted with ethyl acetate, washed with water (2×20 mL), and dried over MgSO$_4$ and evaporated to dryness. The crude product was used without further purification.

The name for Compound 31 is 8-methyltriphenyleno[1,2-d]oxazole-2,3,6,11,12-pentaol.

Compound 31 had the following characterisation data: ES$^+$ MS m/z: 503.26 ([M+2(OC$_5$H$_{11}$)]$^+$ 50%), 433.17 ([M+(OC$_5$H$_{11}$)]$^+$ 100%), 363.08 ([M]$^+$ 10%).

EXAMPLE 32—METHOD OF SYNTHESISING COMPOUND 32

Crude Compound 31 (26 mg, 0.071 mmol), potassium carbonate (74 mg, 0.533 mmol), potassium iodide (6 mg, 0.036 mmol) was dissolved in dry acetonitrile (35 mL). 1(-2-Bromoethoxy)-2-(2-methoxyethoxy)ethane (132 μL, 0.533 mmol) was then added via pipette and the reaction was heated to reflux and stirred under a CaCl$_2$ drying tube for 20 hours. The reaction was cooled to room temperature and the product was extracted with ethyl acetate (20 mL), washed with water (3×20 mL), brine (2×20 mL) and dried over MgSO$_4$ to yield crude Compound 32 as a brown solid.

The name for Compound 32 is 2,3,6,12-tetrakis(2-(2-(2-methoxyethoxy)ethoxy)ethoxy)-8-methyl-11-(pentyloxy) triphenyleno[1,2-d]oxazole.

Compound 32 had the following characterisation data: ES$^+$MS m/z: 1017.51 ([M]$^+$ 100%).

Advantageously, Compound 32 is water soluble.

EXAMPLE 33—METHOD OF SYNTHESISING COMPOUND 33

Figure 16:
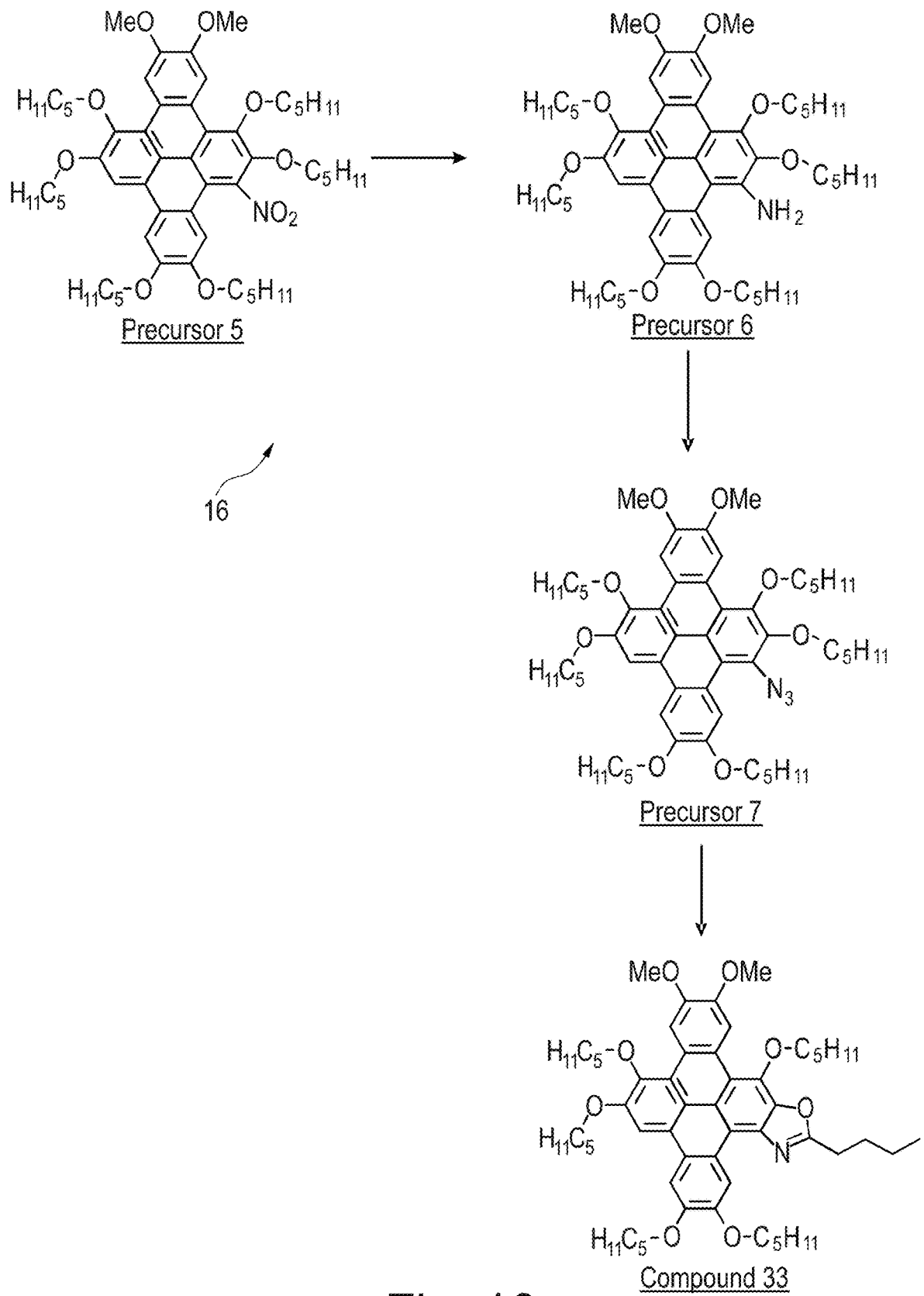
FIG. 16 is a synthetic route to Example 33 of the invention.

Referring now to FIG. 16, there is shown a synthetic route 16 to Compound 33.

Compound 33 was synthesised from Precursor 5 in the following method. The starting material to form Precursor 5 was obtained using the method described in *J. Mater. Chem. C*, 2017, 5, 669-682 (DOI: 10.1039/C6TC04530H).

Precursor 5 was synthesised in the following method. 5,6-dimethoxy-2,3,8,9,12,13-hexakis(pentyloxy)dibenzo [fg,op]tetracene (681 mg, 0.775 mmol) was dissolved in diethyl ether (20 ml) and then acetic acid (1.33 ml, 23.24 mmol, 30 eqiv) was added and the mixture stirred at room temperature in a nitrogen atmosphere for 10 minutes before the addition of fuming nitric acid (65 μL, 1.55 mmol, 2 equiv) was added. The reaction mixture was stirred under nitrogen for 20 minutes before the further addition of nitric acid (30 μL, 0.715 mmol, 0.92 equiv) and the reaction mixture was left for 20 minutes stirring at room temperature. The mixture was then quenched with water (10 ml) and the organic phase was washed with NaOH (1 M, 2×30 mL) and then dried in vacuo to provide Precursor 5 as a black solid (680 mg, 95%). This was used in the next step with no further purification.

The name for Precursor 5 is 5,6-dimethoxy-1-nitro-2,3,8,9,12,13-hexakis(pentyloxy)dibenzo[fg,op]tetracene.

Precursor 5 had the following characterisation data: $^1$H NMR (400 MHz, CDCl3) δ 9.16 (s, 1H), 9.01 (s, 1H), 7.95 (s, 1H), 7.84 (s, 1H), 7.58 (s, 1H), 4.53 (t, J=6.7 Hz, 2H), 4.32 (t, J=5.1 Hz, 2H), 4.29 (t, J=5.3 Hz, 2H), 4.18-4.14 (m, 2H), 4.14 (s, 3H), 4.13 (s, 3H), 3.95 (t, J=6.8 Hz, 2H), 3.95 (t, J=7.0 Hz, 2H), 2.11-1.82 (m, 12H), 1.69-1.29 (m, 24H), 1.08-0.84 (m, 18H). $^{13}$C NMR (101 MHz, CDCl3) δ 151.9, 149.6, 149.3, 148.7, 148.1, 147.9, 144.4, 143.2, 141.5, 124.9, 124.8, 124.7, 124.4, 123.1, 123.1, 122.3, 119.4, 118.6, 116.0, 109.5, 109.3, 107.6, 107.3, 104.9, 76.3, 74.5, 74.0, 69.5, 68.9, 68.8, 55.8, 30.3, 30.3, 29.9, 29.2, 29.0, 28.8, 28.4, 28.3, 28.2, 28.1, 22.6, 22.6, 22.6, 14.1, 14.0, 14.0. MALDI$^+$ m/z: 924.82 ([M+H]$^+$ 30%).

Precursor 6 was synthesised in the following method. Precursor 5 (680 mg, 0.736 mmol) and NiCl$_2$. 6H$_2$O (552 mg, 2.33 mmol, 3 equivalents) were dissolved in THF: MeOH (20 mL, 5:4 ratio), to make a yellow solution, and then NaBH$_4$ (586 mg, 15.5 mmol, 20 equivalents) was added over 15 minutes. The black reaction mixture was left stirring under a nitrogen atmosphere for 40 minutes after which time it was diluted with chloroform and the precipitate was gravity filters to leave a brown organic phase, which was then dried in vacuo to provide Precursor 6 as brown solid (614 mg, 93%).

The name for Precursor 6 is 5,6-dimethoxy-2,3,8,9,12,13-hexakis(pentyloxy)dibenzo[fg,op]tetracen-1-amine.

Precursor 6 had the following characterisation data: $^1$H NMR (300 MHz, CDCl3) δ 9.09 (s, 1H), 8.98 (s, 1H), 8.67 (s, 1H), 7.97 (s, 1H), 7.90 (s, 1H), 4.76 (s, 2H), 4.40 (t, J=6.8 Hz, 2H), 4.34 (t, J=6.5 Hz, 2H), 4.28 (t, J=6.6 Hz, 2H), 4.20 (t, J=6.6 Hz, 2H), 4.11 (s, 3H), 4.08 (s, 3H), 3.99 (t, J=7.0

Hz, 2H), 3.93 (t, J=7.0 Hz, 2H), 2.07-1.88 (m, 12H), 1.66-1.34 (m, 24H), 1.06-0.88 (m, J=22.0, 12.0, 7.1 Hz, 18H). $^{13}$C NMR (101 MHz, CDCl$_3$) δ 151.2, 148.5, 148.2, 148.0, 146.8, 143.8, 139.8, 136.9, 125.4, 125.0, 124.5, 124.4, 123.6, 123.5, 122.6, 120.5, 113.9, 111.8, 110.0, 109.4, 108.6, 108.4, 104.3, 73.9, 73.8, 69.7, 69.2, 69.0, 55.7, 30.4, 30.3, 29.7, 29.3, 29.1, 29.0, 28.5, 28.4, 28.3, 22.7, 22.6, 22.6, 14.1, 14.0. MALDI$^+$ m/z: 893.79 ([M+H]$^+$ 100%).

Precursor 7 was synthesised in the following method. Precursor 6 (147 mg, 0.181 mmol) was dissolved in dry dichloromethane (20 mL) and dry acetonitrile (20 mL). The solution was cooled to 0° C. under a nitrogen atmosphere then tert-butyl nitrite (34 µL, 0.309 mmol, 1.7 equivalents) and TMSN$_3$ (36 µL, 0.273 mmol, 1.5 equivalents) were added and the reaction mixture stirred 0° C. for 10 minutes and then at room temperature for 20 minutes. The solution was then dried in vacuo and purified via flash column chromatography (silica, 30% DCM, 70% n-hexane) to provide Precursor 7 as a while solid (120 mg, 72%).

The name for Precursor 7 is 1-azido-5,6-dimethoxy-2,3, 8,9,12,13-hexakis(pentyloxy)dibenzo[fg,op]tetracene.

Precursor 7 had the following characterisation data: $^1$H NMR (300 MHz, CDCl3) δ 9.12 (s, 1H), 9.03 (s, 1H), 8.98 (s, 1H), 8.01 (s, 1H), 7.89 (s, 1H), 4.45 (t, J=6.7 Hz, 2H), 4.38-4.32 (m, 2H), 4.29 (t, J=6.0 Hz, 2H), 4.11 (s, 3H), 4.09 (s, 3H), 4.01 (t, 2H), 3.94 (t, J=6.6 Hz, 2H), 2.13-1.84 (m, 12H), 1.69-1.32 (m, 24H), 1.04-0.87 (m, 18H). $^{13}$C NMR (101 MHz, CDCl3) δ 151.57, 148.85, 148.03, 147.99, 147.89, 147.88, 146.27, 144.06, 127.30, 125.39, 124.82, 123.99, 123.85, 123.33, 123.17, 122.79, 120.18, 119.39, 117.58, 112.56, 109.38, 109.10, 107.51, 104.74, 75.30, 74.36, 73.97, 69.64, 69.14, 69.01, 55.81, 30.39, 30.32, 29.53, 29.25, 29.08, 28.94, 28.45, 28.33, 28.23, 28.22, 22.70, 22.62, 22.57, 14.10, 14.01.

Compound 33 was synthesised using the following method. Precursor 7 (100 mg; 0.13 mmol) was dissolved in dry toluene (5 mL) was added to a flask containing rhodium octanoate dimer (5 mg; 0.01 mmol), under a nitrogen atmosphere. This mixture was then heated to reflux and stirred for 20 hours. The reaction was cooled to room temperature and then dried in vacuo, the solid was then purified via flash column chromatography (silica; 95% n-hexane: 5% ethyl acetate) to provide Compound 33 as a white solid (58 mg, 50%).

The name of Compound 33 is 2-butyl-12,13-dimethoxy-5,6,9,10,15-pentakis(pentyloxy)dibenzo[4,5:9,10]pyreno[1,2-d]oxazole.

Compound 33 had the following characterisation data: $^1$H NMR (300 MHz, CDCl3) δ 10.08 (s, 1H), 9.28 (s, 1H), 9.15 (s, 1H), 8.16 (s, 1H), 8.02 (s, 1H), 4.42 (t, J=6.0 Hz, 2H), 4.37 (d, J=5.8 Hz, 2H), 4.35-4.29 (m, J=6.7, 3.3 Hz, 4H), 4.12 (s, 3H), 4.11 (s, 3H), 3.98 (t, J=6.9 Hz, 2H), 3.18 (t, J=7.5 Hz, 2H), 2.09-1.92 (m, 10H), 1.67-1.36 (m, 24H), 1.07-0.90 (m, 18H). $^{13}$C NMR (101 MHz, CDCl3) δ 166.1, 151.3, 149.5, 148.8, 147.8, 147.7, 144.0, 142.4, 138.4, 137.1, 125.5, 124.9, 124.1, 124.0, 123.7, 123.5, 123.0, 119.9, 118.8, 116.1, 111.3, 109.6, 109.4, 107.1, 104.8, 74.5, 74.0, 69.8, 69.0, 68.8, 55.8, 55.7, 30.3, 30.1, 29.3, 29.1, 28.9, 28.7, 28.5, 28.4, 28.3, 28.2, 22.6, 22.5, 22.3, 14.1, 14.0, 13.8. MALDI$^+$ m/z: 889.16 ([M+H]$^+$ 100%).

EXAMPLE 34—METHOD OF SYNTHESISING COMPOUND 34

Precursor 6 (47 mg; 0.053 mmol), benzoyl chloride (30 µL, 0.265 mmol, 5 equivalents), and diisopropylehtylamine (46 µL, 0.265 mmol, 5 equiv) were dissolved in dry toluene (5 mL) and the mixture was heated to reflux under a nitrogen atmosphere. The reaction mixture was stirred for 1 hour at which point the mixture was dried in vacuo then the solid was heated to 240° C. for 10 minutes. The reaction was cooled to room temperature and the solid was then purified via flash column chromatography (silica; 40% DCM, 60% n-hexane) to afford Compound 34 a white solid (16 mg, 33%).

The name of Compound 34 is 12,13-dimethoxy-5,6,9,10, 15-pentakis(pentyloxy)-2-phenyldibenzo[4,5:9,10]pyreno [1,2-d]oxazole.

Compound 34 had the following characterisation data: $^1$H NMR (300 MHz, CDCl3) δ 9.29 (s, 1H), 9.19 (s, 1H), 8.48-8.43 (m, 2H), 8.17 (s, 1H), 8.03 (s, 1H), 7.65-7.59 (m, 3H), 4.53 (t, J=6.9 Hz, 2H), 4.44-4.33 (m, 6H), 4.14 (s, 3H), 4.12 (s, 3H), 3.99 (t, J=6.9 Hz, 2H), 2.15-1.90 (m, 10H), 1.71-1.36 (m, 24H), 1.06-0.80 (m, 18H). $^{13}$C NMR (101 MHz, CDCl3) δ 166.6, 161.8, 151.4, 149.5, 148.9, 147.9, 147.9, 144.1, 142.5, 138.5, 137.7, 132.9, 131.5, 129.5, 129.0, 128.4, 127.6, 127.4, 125.6, 124.8, 124.3, 124.0, 123.8, 123.5, 123.3, 119.8, 119.7, 116.4, 111.3, 109.7, 109.4, 106.9, 104.8, 74.7, 74.1, 69.8, 69.0, 64.5, 55.8, 55.7, 30.4, 30.2, 29.7, 29.3, 29.1, 28.9, 28.5, 28.5, 28.4, 25.6, 22.6, 22.5, 14.2, 14.1, 14.1, 14.1, 14.0. ES$^+$ m/z: 910.54 ([M+H]$^+$ 100%).

EXAMPLE 35—METHOD OF SYNTHESISING COMPOUND 35

Precursor 6 (100 mg; 0.111 mmol) 4-cyanobenzoyl chloride (92 mg, 0.555 mmol, 5 equiv), and diisopropylehtylamine (90 µL, 0.555 mmol, 5 equiv) were dissolved in dry toluene (5 mL) and the mixture was heated reflux under a nitrogen atmosphere. The reaction mixture was stirred for 1 hour at which point the mixture was dried in vaccuo then the solid was heated to 240° C. for 10 minutes. The reaction was cooled to room temperature and the solid was then purified via flash column chromatography (silica; 40% DCM, 60% n-hexane) to afford Compound 35 as a white solid (17 mg, 16%).

The name of Compound 35 is 4-(12,13-dimethoxy-5,6,9, 10,15-pentakis(pentyloxy)dibenzo[4,5:9,10]pyreno[1,2-d] oxazol-2-yl)benzonitrile.

Compound 35 had the following characterisation data: $^1$H NMR (300 MHz, CDCl$_3$) δ 10.02 (s, 1H), 9.27 (s, 1H), 9.15 (s, 1H), 8.43 (d, J=8.3 Hz, 2H), 8.13 (s, 1H), 7.99 (s, 1H), 7.84 (d, J=8.3 Hz, 2H), 4.45 (t, J=6.8 Hz, 2H), 4.36 (dt, J=13.0, 6.4 Hz, 6H), 4.14 (s, 3H), 4.12 (s, 3H), 3.97 (t, J=6.9 Hz, 2H), 2.12-1.90 (m, 10H), 1.65-1.38 (m, 24H), 1.06-0.88 (m, 18H). $^{13}$C NMR (100 MHz, CDCl$_3$) δ 159.8, 151.9, 149.9, 149.5, 148.5, 148.3, 144.6, 143.0, 138.6, 137.6, 133.0, 131.5, 128.0, 125.8, 124.8, 124.4, 123.9, 123.8, 123.8, 121.1, 119.9, 118.6, 117.0, 114.7, 111.5, 110.1, 109.8, 107.1, 105.2, 75.1, 74.4, 70.1, 69.3, 56.2, 56.1, 30.7, 30.5, 30.0, 29.6, 29.5, 29.3, 28.9, 28.8, 28.7, 28.7, 23.0, 22.9, 22.9, 14.6, 14.5, 14.4. MALDI$^+$ m/z: 934.55 ([M+H]$^+$ 100%).

Method of Synthesising Compound XX

Compound XX was synthesised using the following method. Compound 404 (wherein R'=C$_5$H$_{11}$) shown in FIG. 4 (550 mg, 0.632 mmol) was dissolved in dry dichloromethane under a nitrogen atmosphere at 0° C. 0.01M solution of Br$_2$ in dichloromethane (256 mL, 2.528 mmol) was then added over 1 h (4×64 mL) and monitered by TLC. The reaction was stired overnight and then quenched by addition of saturated sodium metabisulfate solution (100 mL). The product was extracted with dichloromethane (30 mL), washed with water (3×30 mL), dried over MgSO$_4$ and evaporated to dryness. The crude product was then purified by column chromatography (Silica 40% dichloromethane: hexane) to yield Compound XX as a yellow solid (220 mg, 36%).

The name for Compound XX is 1-bromo-8-nitro-2,3,6,7,10,11-hexakis(pentyloxy)triphenylene.

Compound XX had the following characterisation data:
$^1$H NMR (300 MHz, CDCl$_3$) δH: 8.78 (1H, s), 7.79 (1H, s), 7.69 (1H, s), 7.42 (1H, s), 4.25-4.17 (8H, m), 4.12-4.06 (4H, m), 1.97-1.77 (12H, m), 1.57-1.40 (24H, m), 1.00-0.93 (18H, m) ppm. ES$^+$MS m/z: 867.43 ([M]$^+$ 25%).

It is understood that the method of brominating Compound XX may be applied to the phenoxazoles of the invention, for example, to add further functionality to the molecules.

Properties of Triphenylene Derivative Series 100

The triphenylene derivative series 100 of the present invention exhibits a number of advantageous properties that are useful in many applications. Some of these advantageous properties are demonstrated below in a non-limiting way.

Figure 8:
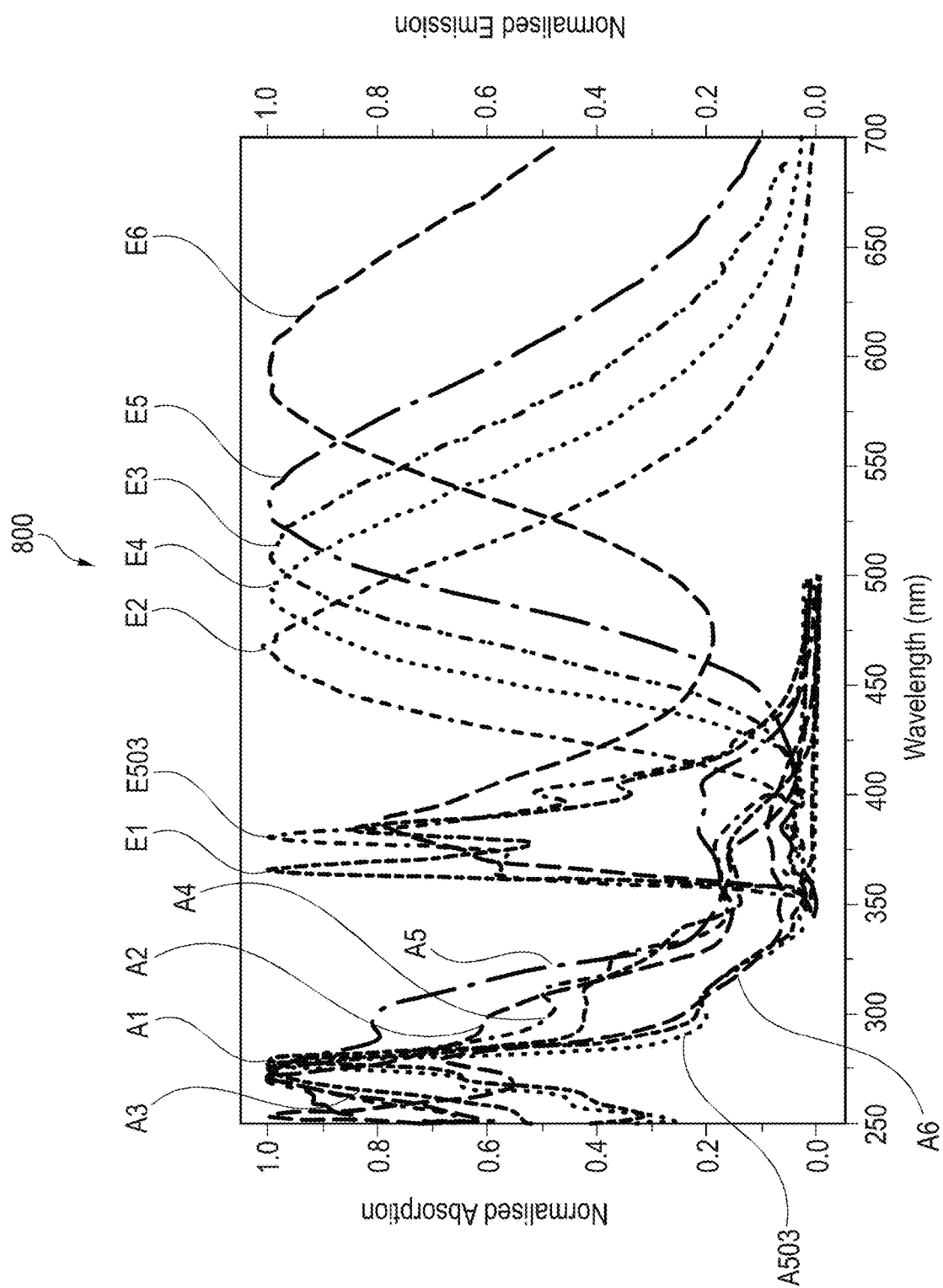
FIG. 8 is a normalised absorption and emission spectra for the triphenylene derivatives according to examples of the invention.

Referring to FIG. 8, there is shown the normalised absorption and emission spectra 800 for Compounds 1 to 6 of Examples 1 to 6, and for compound 403. The solvent used to record the spectra was acetonitrile.

There is shown the absorption spectra (designated with the prefix A) for Compounds 1 to 6 (A1, A2, A3, A4, A5, A6) and the emission spectra (designated with the prefix E) for Compounds 1 to 6 (E1, E2, E3, E4, E5, E6). The full emission spectrum E6 for Compound 6 could not be detected due to equipment limitations.

The absorption spectra A403 and emission spectra E403 of intermediate compound 403 shown in FIG. 4 (2,3,6,7,10,11-hexakis(pentyloxy)triphenylene) was also recorded and used as a reference.

Referring also to Table 1, there is shown luminescent data for the Compounds 1 to 6. There is shown the maximum absorption values λmax (nm), the maximum emission values λmax (nm), the pseudo Stokes shift pSS (cm$^{-1}$), the quantum yield ϕ, and the brightness (M$^{-1}$ cm$^{-1}$). The luminescent data shown in Table 1 was recorded for each of the Compounds 1 to 6 individually in ethyl acetate, octan-1-ol, and acetonitrile.

Referring also to Table 2, there is shown further luminescent data for Compounds 1 to 6. There is shown the molar extinction coefficients (E×10$^3$) (M$^{-1}$ cm$^{-1}$) alongside the maximum absorption values αmax (nm), recorded at a concentration of 1×10$^{-7}$ mol dm$^{-3}$ individually in ethyl acetate, octan-1-ol, and acetonitrile.

TABLE 2

Luminescent Absorption data for Compounds 1 to 6

| | Ethyl acetate | | Octan-1-ol | | Acetonitrile | |
|---|---|---|---|---|---|---|
| | ε × 10$^3$ (M$^{-1}$ cm$^{-1}$) | λmax (nm) | ε × 10$^3$ (M$^{-1}$ cm$^{-1}$) | λmax (nm) | ε × 10$^3$ (M$^{-1}$ cm$^{-1}$) | λmax (nm) |
| Compound 1 | 160 ± 15 | 278 | 120 ± 12 | 278 | 58 ± 6 | 278 |
| Compound 2 | 110 ± 11 | 270 | 105 ± 10 | 271 | 66 ± 6 | 271 |
| Compound 3 | 117 ± 12 | 275 | 122 ± 12 | 275 | 84 ± 8 | 275 |
| Compound 4 | 164 ± 16 | 272 | 128 ± 13 | 272 | 85 ± 9 | 273 |
| Compound 5 | 105 ± 10 | 272 | 106 ± 11 | 270 | † | 270 |
| Compound 6 | 158 ± 10 | 253 | 152 ± 15 | 255 | 106 ± 11 | 253 |

† No value could be obtained because of Compound 5 poor solubility in acetonitrile The triphenylene derivative series 100, which are exemplified as Compounds 1 to 6, exhibit many advantageous luminescent properties (as demonstrated by the data in Tables 1 and 2, and FIG. 8) which are discussed below.

Large Stokes Shift

Compounds 1 to 6 exhibit large Stokes shifts in comparison with many commercially available dyes, e.g. the Alexa Fluor series (J Histochem Cytochem. Vol. 51(12): 1699-1712, 2003). It is believed that the Stokes shifts of Compounds 1 to 6 (Compound 6 in particular) are some of the largest Stokes shifts observed for known luminescent organic compounds.

Additionally, the advantageous luminescent properties such as the Stokes shift may be altered or 'tuned' by variation of the R group within the triphenylene derivative series 100.

For example, as shown in Table 1 and FIG. 8, the maximum absorption wavelength remains relatively con-

TABLE 1

Luminescent data for Compounds 1 to 6

| Solvent | ε$_r$ | Viscosity (cP) | | Compound 1 | Compound 2 | Compound 3 | Compound 4 | Compound 5 | Compound 6 |
|---|---|---|---|---|---|---|---|---|---|
| Ethyl acetate | 6.0 | 0.45 | Absorption λ$_{max}$ (nm) | 281 | 270 | 272 | 275 | 272 | 253 |
| | | | Emission λ$_{max}$ (nm) | 367 | 467 | 494 | 510 | 536 | 594 |
| | | | pSS (cm$^{-1}$) | 8300 | 15600 | 16500 | 16800 | 18100 | 22700 |
| | | | Φ | 0.18 ± 0.01 | 0.46 ± 0.04 | 0.55 ± 0.05 | 0.48 ± 0.04 | 0.51 ± 0.04 | † |
| | | | Brightness (M$^{-1}$ cm$^{-1}$) | 29 ± 5 | 51 ± 5 | 92 ± 9 | 56 ± 5 | 53 ± 5 | † |
| Octan-1-ol | 10.3 | 7.36 | Absorption λ$_{max}$ (nm) | 281 | 271 | 272 | 275 | 270 | 255 |
| | | | Emission λ$_{max}$ (nm) | 367 | 473 | 497 | 515 | 526 | 384 |
| | | | pSS (cm$^{-1}$) | 8300 | 15800 | 16600 | 17000 | 18000 | 13200 |
| | | | Φ | 0.30 ± 0.03 | 0.61 ± 0.06 | 0.71 ± 0.07 | 0.55 ± 0.05 | 0.56 ± 0.05 | † |
| | | | Brightness (M$^{-1}$ cm$^{-1}$) | 36 ± 7 | 64 ± 6 | 91 ± 9 | 67 ± 7 | 50 ± 5 | † |
| Acetonitrile | 37.5 | 0.38 | Absorption λ$_{max}$ (nm) | 281 | 270 | 273 | 275 | 270 | 253 |
| | | | Emission λ$_{max}$ (nm) | 367 | 492 | 524 | 543 | 592 | 630 |
| | | | pSS (cm$^{-1}$) | 8300 | 16700 | 17600 | 18000 | 20200 | 23650 |
| | | | Φ | 0.20 ± 0.02 | 0.46 ± 0.04 | 0.51 ± 0.05 | 0.36 ± 0.04 | 0.21 ± 0.02 | † |
| | | | Brightness (M$^{-1}$ cm$^{-1}$) | 12 ± 2 | 38 ± 4 | 44 ± 4 | 30 ± 3 | ‡ | † |

† No value could be obtained
‡ No value could be obtained due to poor solubility and therefore no ε data.

stant for each of the Compounds 1 to 6. However, the maximum emission wavelength undergoes a red shift as the R group is varied, i.e. the R group is changed from an alkyl group (Compound 1, wherein R=$C_4H_9$) to a phenyl group (Compound 2, wherein R=Ph) or a polycyclic aromatic hydrocarbon (Compounds 3 to 6, wherein R=naphthalene or anthracene). This 'tunable' characteristic is not observed with many other commercially available dyes.

It should be noted that by Stokes shift, we also mean a 'pseudo' Stokes shift. The IUPAC definition of the Stokes shift requires that the difference in the band maxima of the absorption and luminescence arise from the same electronic transition. However, it is widely referred to in the literature in general terms to mean the difference in excitation and emission wavelengths, regardless of electronic transition.

Without wishing to be bound by theory, we believe that the triphenylene derivative series 100 of the present invention are push-pull twisted internal charge transfer systems, wherein the triphenylene moiety when substituted with five electron-donating alkoxy groups (shown in FIG. 1 as $C_5H_{11}$), provides a 'push' moiety. The R group provide a 'pull' moiety when conjugatively coupled to the triphenylene moiety further by the oxazole unit. Therefore, further stabilisation of the excited state may be achieved by increasing the electron withdrawing nature of the R group. As the energy of the excited state is lowered, this increases the Stokes shift. Advantageously, the triphenylene derivative series 100 of the present invention may be tuned to provide this characteristic, as required depending upon the application.

Emission across the entire Visible Spectrum, which varies with R group structure Advantageously, the emission spectra of Compounds 1 to 6 span a large portion of the visible spectrum. The R group need not be limited to those disclosed, and may be any alkyl or aryl group. In particular, variation of the R group with, for example, a different aromatic hydrocarbon group has been shown to result in a shift in the emission spectra. The shift in emission, and consequently the resulting visible colour of a specific triphenylene derivative, within the triphenylene derivative series 100, may be predicted with a good level of certainty for variation of the R group. Advantageously, this provides a huge number of analogues, for example wherein R is an aryl group, so that the emission is a colour within the visible spectrum, and this visible colour may be 'tuned' by slight structural alteration to the R group of the triphenylene derivative series 100 of the present invention.

High Brightness

Compounds 1 to 6 exhibit very large molar extinction coefficients (E) of over 100,000 $M^{-1}$ $cm^{-1}$. This is comparable to commercially available dyes, for example, the Alexa Fluor series, e.g. Alexa Fluor 635 has a molar extinction coefficient of 140,000 $M^{-1}$ $cm^{-1}$.

Compounds 1 to 6 also advantageously exhibit high quantum yields ϕ and high brightness values. The quantum yield ϕ in this case is defined as the ratio of the number of photons emitted to the number of photons absorbed.

Consequently, the Compounds 1 to 6 exhibit high brightness values, the brightness being defined as the product of the molar extinction coefficient and fluorescence quantum yield.

Additionally, it has surprisingly been found that Compound 22 has a quantum yield of 93%.

Photoemission in the Solid State

Figure 9:
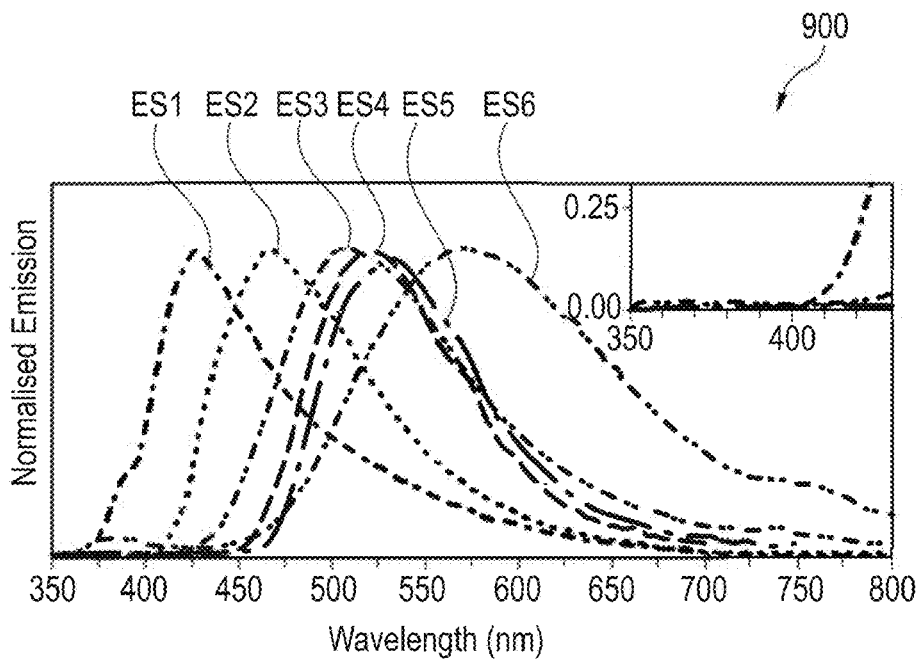
FIG. 9 is a photoemission of the triphenylene derivatives in the solid state according to some examples of the invention.

Referring now to FIG. 9, there is shown a graph of the normalised photoemission 900 of Compounds 1 to 6 in the solid state. There is shown the photoemission in the solid state (designated with the prefix ES) for Compounds 1 to 6 (ES1, ES2, ES3, ES4, ES5, ES6).

Referring also to Table 3, there is shown a comparison of the photoemission of the Compounds 2 to 6 in the solid state and in ethyl acetate, and the difference between these values Δ.

TABLE 3

| | Photoemission data for Compounds 2 to 6 | | | | |
|---|---|---|---|---|---|
| | Compound 2 Emission Max (nm) | Compound 3 Emission Max (nm) | Compound 4 Emission Max (nm) | Compound 5 Emission Max (nm) | Compound 6 Emission Max (nm) |
| Ethyl acetate | 467 | 508 | 492 | 537 | 594 |
| Solid state | 467 | 520 | 509 | 533 | 575 |
| Δ | 0 | +12 | +17 | −7 | −19 |

Advantageously, the photoemission does not substantially change when Compounds 2 to 6 are dissolved in ethyl acetate in comparison to in the solid state. This demonstrates predictability and stability of photo-emissive behaviour.

Liquid Crystal Behaviour

Referring to Table 4 there is shown the DSC (Differential scanning calorimetry) thermal analysis for Compounds 1 to 6.

TABLE 4

| DSC properties of Compounds 1 to 6 | | | | | |
|---|---|---|---|---|---|
| Compound | Heating (° C.) | | | Cooling (° C.) | |
| Phase | Cr-X | X-$Col_h$ | $Col_h$-I | I-$Col_h$ | $Col_h$-Cr |
| Compound 1 | 95 | 99 | 141 | 137 | 59 |
| Compound 2 | 103 | 110 | 189 | 185 | 78 |
| Compound 3 | 86 | 96 | 168 | 161 | 43 |
| Compound 4 | 88 | 96 | 197 | 196 | 152* |
| Compound 5 | | 162 | 185 | 151 | 83 |
| Compound 6† | | 172 | 182 | 151 | 134 |
| | | Cr-$Col_x$ | $Col_x$-I | I-$Col_x$ | $Col_x$-Cr |

†Compound 6 phase changes displayed in bold underneath the temperature

There is shown the phase transition for each of the Compounds 1 to 6, wherein Cr means crystalline, X means an unknown endothermic event, $Col_h$ means hexagonal columnar phase, and $Col_x$ means unknown liquid crystalline state. This shows that Compounds 1 to 6 are mesogenic, i.e. have liquid crystallinity.

Figure 10:
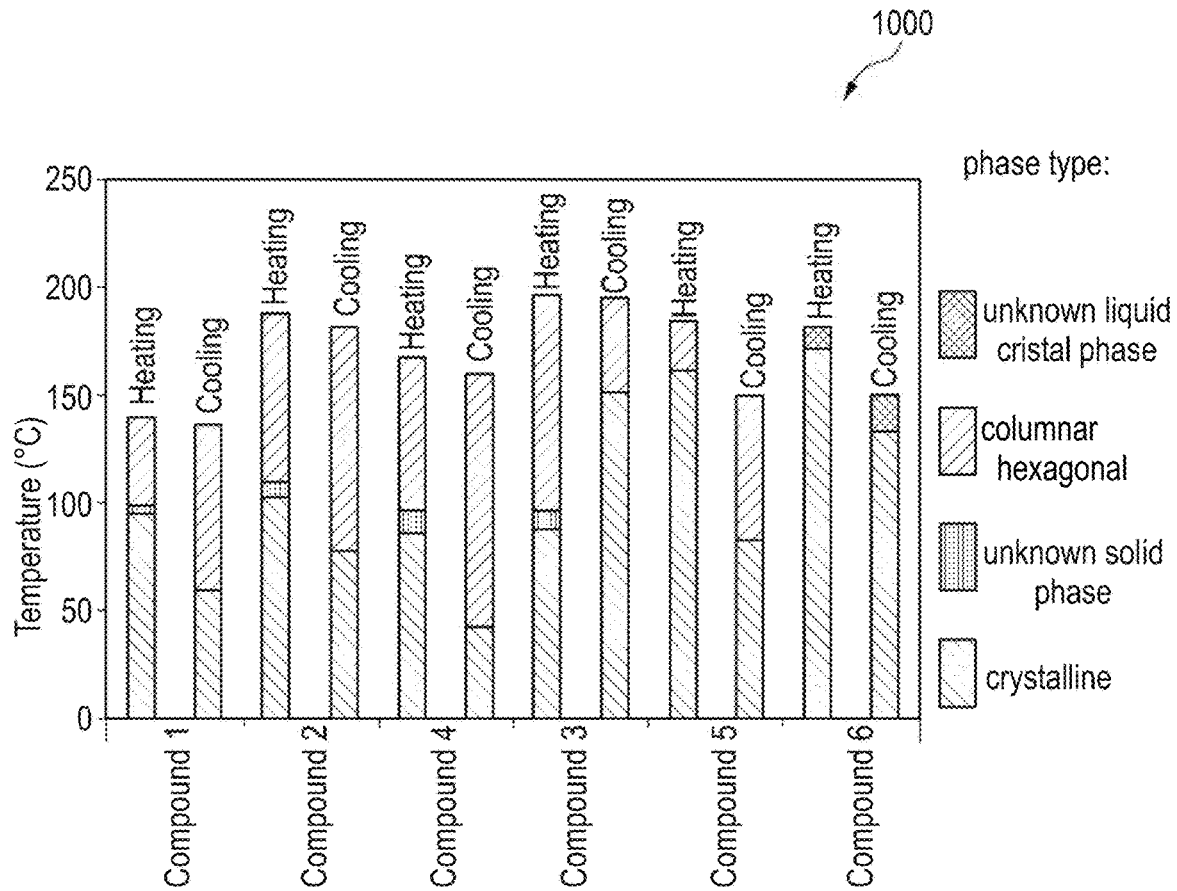
FIG. 10 is a graph showing DSC (Differential scanning calorimetry) thermal analysis data for the triphenylene derivatives according to some examples of the invention.

Referring also to FIG. 10 there is shown a DSC (Differential scanning calorimetry) thermal analysis plot 1000 of phase type of Compounds 1 to 6, shown for both heating and cooling.

The crystalline phase, the unknown solid phase, the columnar hexagonal phase, and the unknown liquid crystal phase are shown.

Photoconductivity

Referring to Table 5 there is shown the values for the average conductivity and the average photoconductivity of Compounds 1 to 6, when irradiated at 350 nm at room temperature. The molar absorptivity constant ($E_{350\ nm}$) at 350 nm in ethyl acetate is also provided. The conductivity and photoconductivity were also recorded for compound 403 shown in FIG. 4, which is used as a reference.

TABLE 5

Conductivity and photoconductivity for Compounds 1 to 6

| Compound | ($\epsilon_{350\,nm}$) × $10^3$ in ethyl acetate $M^{-1}\,cm^{-1}$ | Average Conductivity (S $cm^{-1}$) | Average Photoconductivity (S $cm^{-1}$) |
|---|---|---|---|
| Reference 403 | 3.6 | $2.4 \times 10^{-13}$ | $1.98 \times 10^{-11}$ |
| Compound 1 | 6.4 | $5.3 \times 10^{-13}$ | $2.0 \times 10^{-10}$ |
| Compound 2 | 19 | $6.6 \times 10^{-12}$ | $3.1 \times 10^{-9}$ |
| Compound 3 | 26 | $4.1 \times 10^{-12}$ | $6.9 \times 10^{-9}$ |
| Compound 4 | 16 | $1.7 \times 10^{-11}$ | $2.3 \times 10^{-9}$ |
| Compound 5 | 19 | $9.3 \times 10^{-12}$ | $1.5 \times 10^{-9}$ |
| Compound 6 | 11 | $2.0 \times 10^{-12}$ | $1.1 \times 10^{-10}$ |

Advantageously, Compounds 1 to 6 show an increase in conductivity, i.e. the photoconductivity values, upon light irradiation. The conductivity and the photoconductivity is much higher for the triphenylene derivatives comprising an oxazole moiety, when compared to reference compound 403, which does not comprise an oxazole moiety. More advantageously, the photoconductivity increases significantly when the R group is a polycyclic aromatic hydrocarbon, i.e. for Compound 2, wherein R=Ph, and for Compounds 3 and 4, wherein R=naphthalene.

Figure 11:
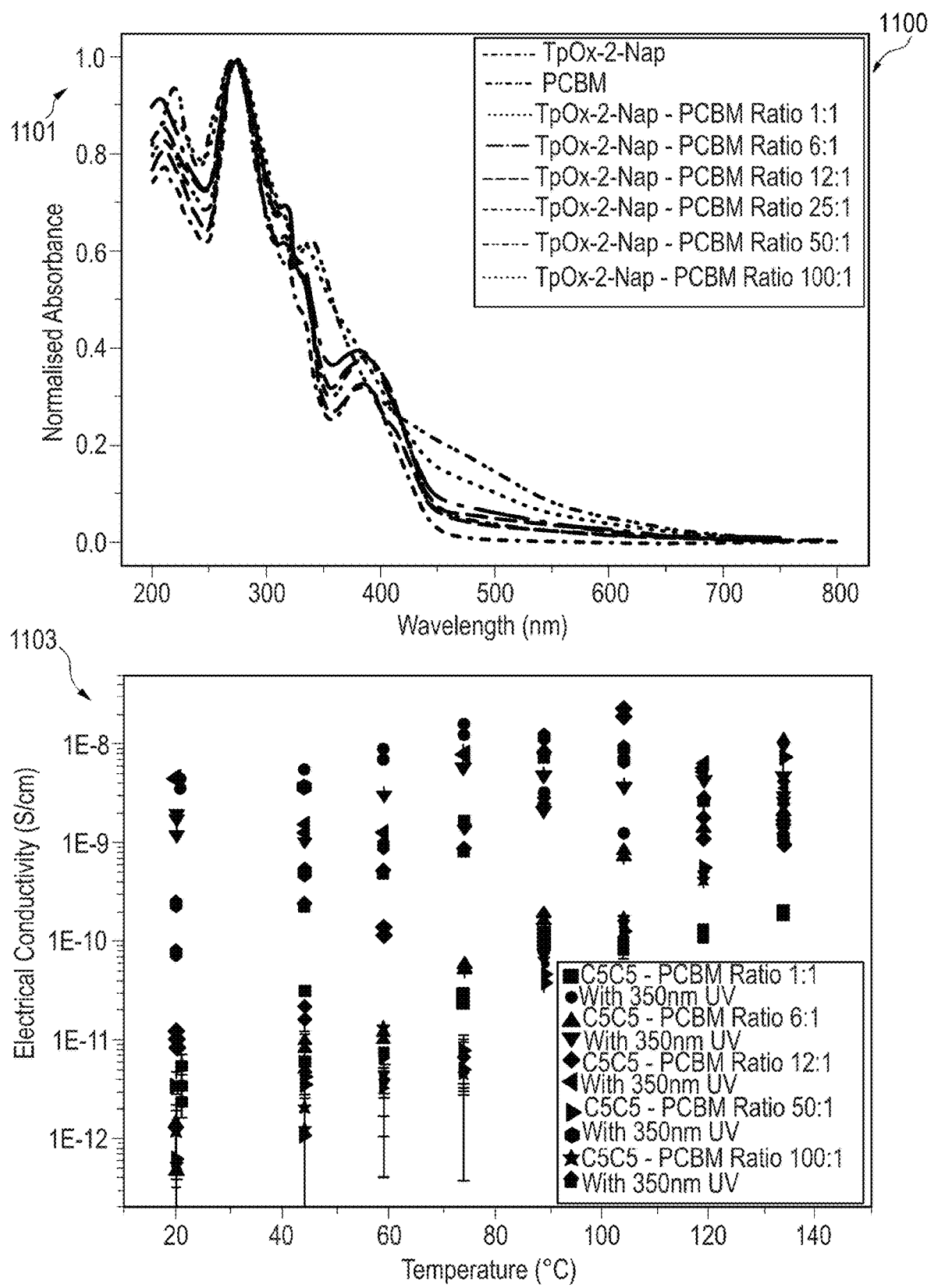
FIG. 11 is data from photoconductivity experiments performed on the triphenylene derivatives according to some examples of the invention.
Figure 11:
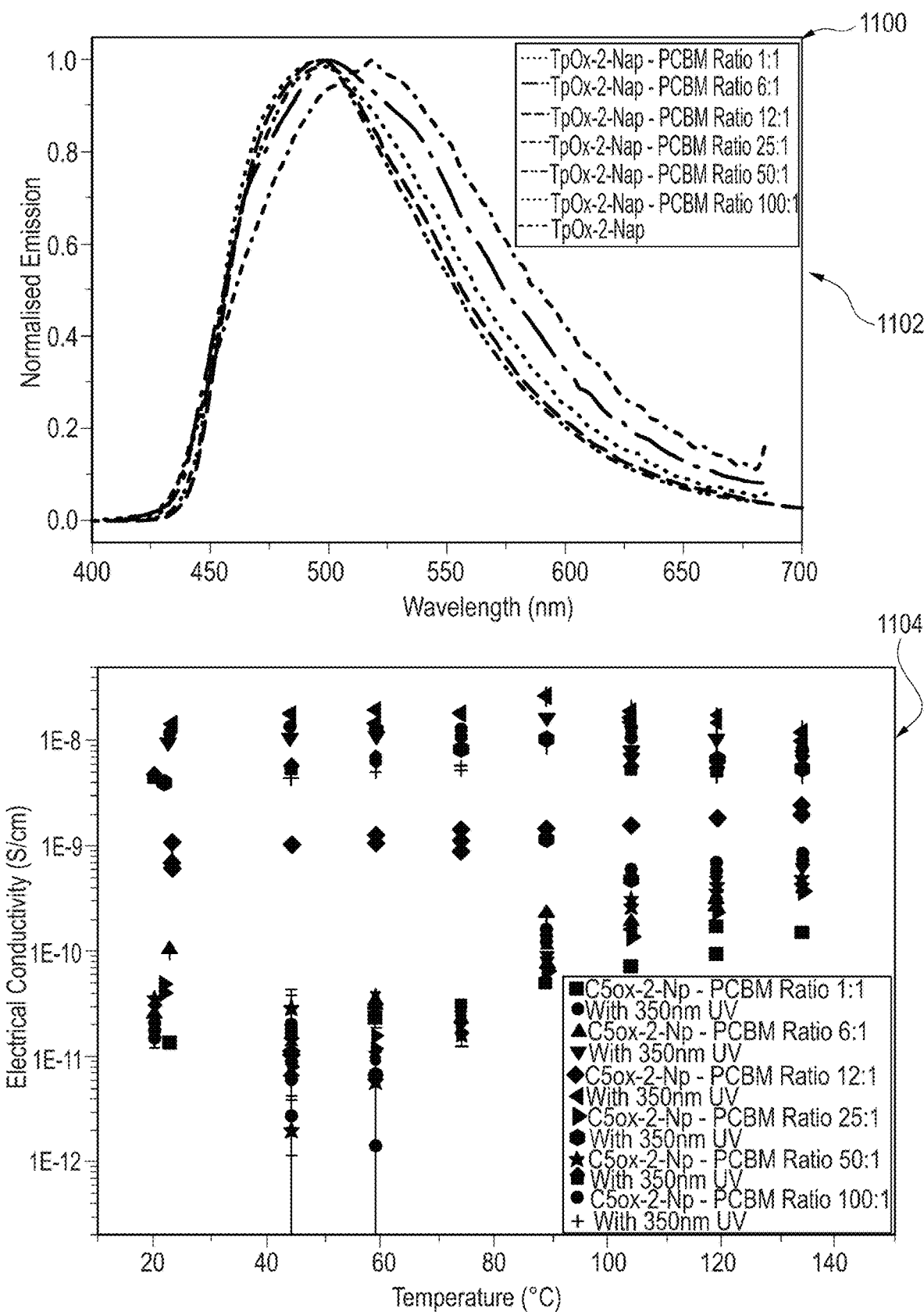

Referring also to FIG. 11 there is shown a photoconductivity experiment 1100 for Compound 3 in comparison with the reference compound 403 (shown in FIG. 4). The absorbance spectra 1101 and emission spectra 1102 of Compound 3 was measured in the presence of phenyl-C61-butyric acid methyl ester (PCBM) at different ratios. The graph 1103 shows measurements of the electrical conductivity at different temperatures with light irradiation at 350 nm for the reference compound 403. The graph 1104 shows measurements of the electrical conductivity at different temperatures with light irradiation at 350 nm for Compound 3.

Surprisingly, Compound 3 displays improved conductivity, and photoconductivity, when the oxazole moiety is introduced. This is in comparison with the conductivity and photoconductivity of reference compound 403, which does not comprise an oxazole moiety substituted with an R group, as is characteristic of the triphenylene derivative series 100 of the present invention.

It has also been shown that compounds within the triphenylene derivative series 100 of the present invention do not undergo any appreciable photobleaching. The aforementioned properties make the triphenylene derivatives of the present invention highly suitable for use in solar cells.

Figure 12:
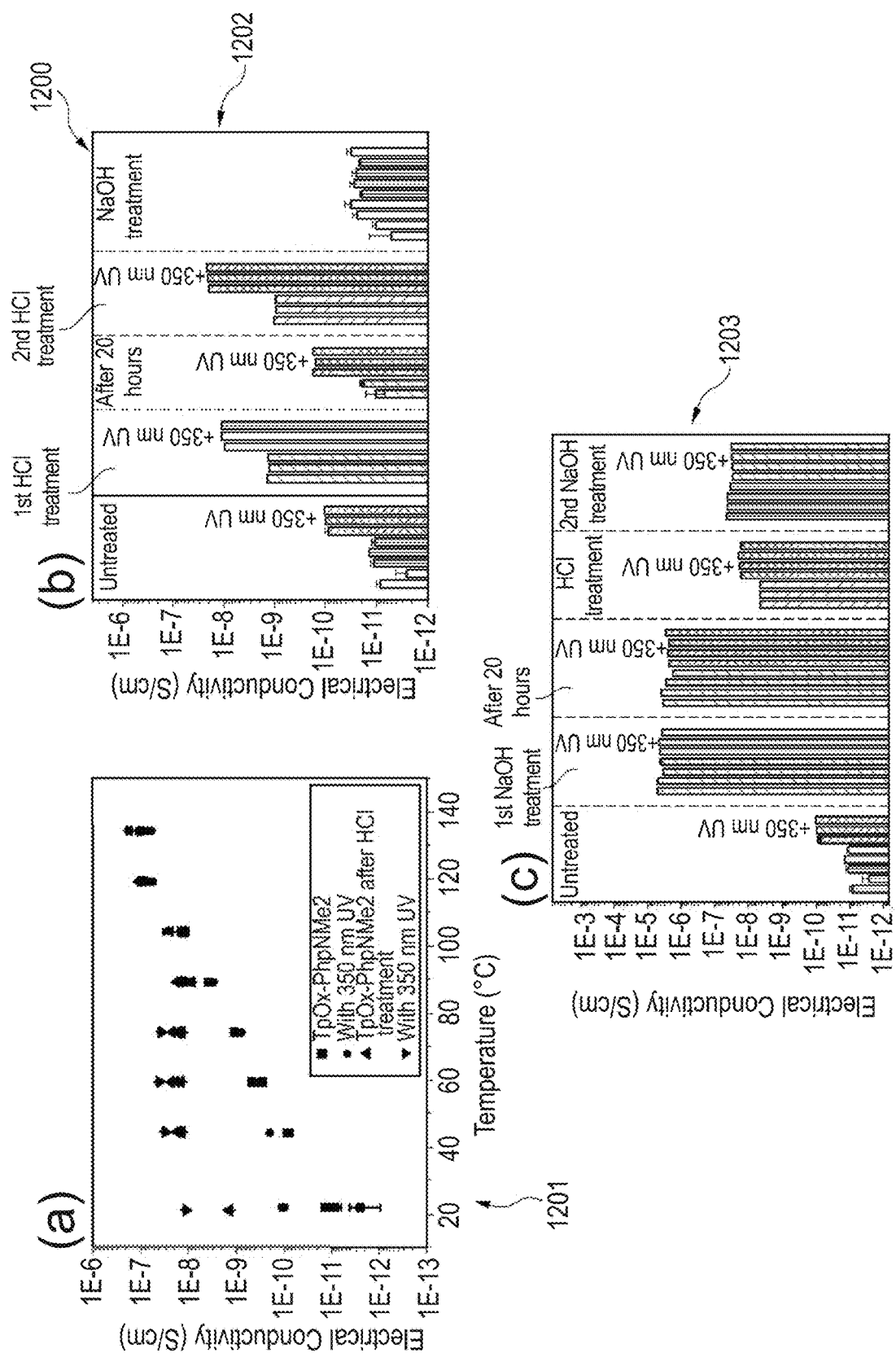
FIG. 12 is graphical data showing the electrical conductivity of a triphenylene derivative according to an example of the invention.

Referring now to FIG. 12, there is shown a photoconductivity experiment 1200 for Compound 22. There is shown a graph 1201, a graph 1202, and a graph 1203.

The graph 1201 shows the electrical conductivity measurements for Compound 22 at different temperatures. Electrical conductivity measurements were recorded for Compound 22 in the presence and absence of irradiating UV light at 350 nm, and after treatment with HCl in the presence and absence of irradiating UV light at 350 nm.

The graph 1202 shows the electrical conductivity measurements for Compound 22 at different pH values. The electrical conductivity was measured for Compound 22: (i) untreated; (ii) after a first treatment with HCl; (iii) after 20 hours; (iv) after a second treatment with HCl; (v) and after treatment with NaOH.

The graph 1203 shows the electrical conductivity measurements for Compound 22 at different pH values. The electrical conductivity was measured for Compound 22: (i) untreated; (ii) after a first treatment with NaOH; (iii) after 20 hours; (iv) after treatment with HCl; (v) after a second treatment with NaOH.

Figure 13:
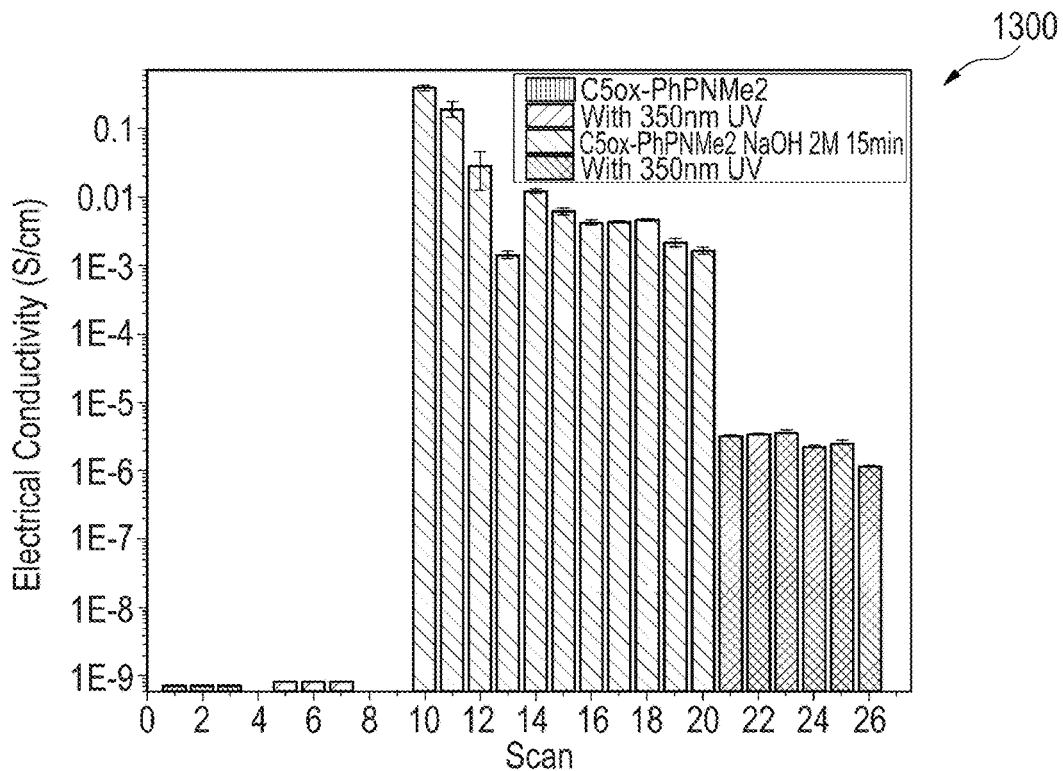
FIG. 13 is a graph showing the electrical conductivity of triphenylene derivative according to an example of the invention.

Referring now to FIG. 13, there is shown a photoconductivity experiment 1300 for Compound 22. The electrical conductivity was measured for Compound 22: (i) untreated;
(ii) untreated in the presence of UV light at 350 nm; (iii) after treatment with NaOH (2M for 15 minutes); (iv) after treatment with NaOH (2M for 15 minutes) in the presence of UV light at 350 nm.

Figure 14:
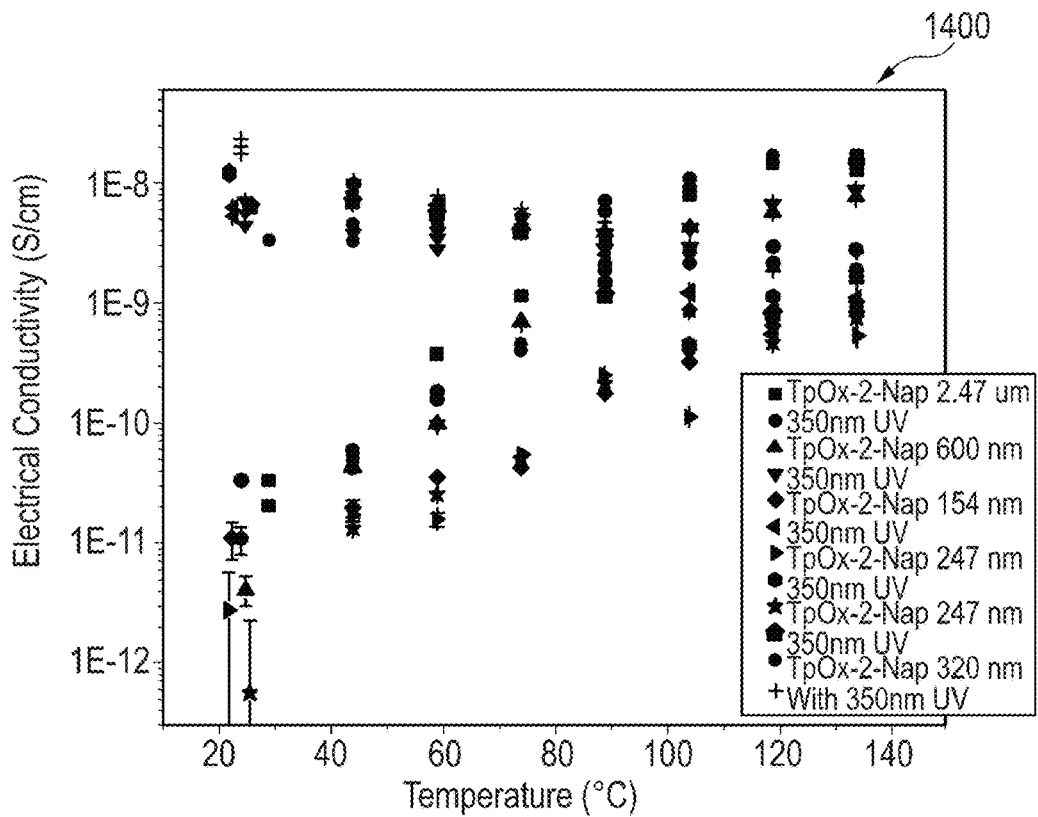
FIG. 14 is a graph showing the electrical conductivity of triphenylene derivative according to an example of the invention.

Referring now to FIG. 14, there is shown a photoconductivity experiment 1400 for Compound 3. The electrical conductivity was measured at different temperatures.

Application of Triphenylene Derivative Series 100 in Electroluminescent Devices

The triphenylene derivatives of the present invention may also be used in a functional layer of an OLED (Organic Light Emitting Diode). It has been shown that the triphenylene derivatives of the present invention may exhibit excellent emitting, charge transporting, and/or charge blocking abilities.

Figure 15:
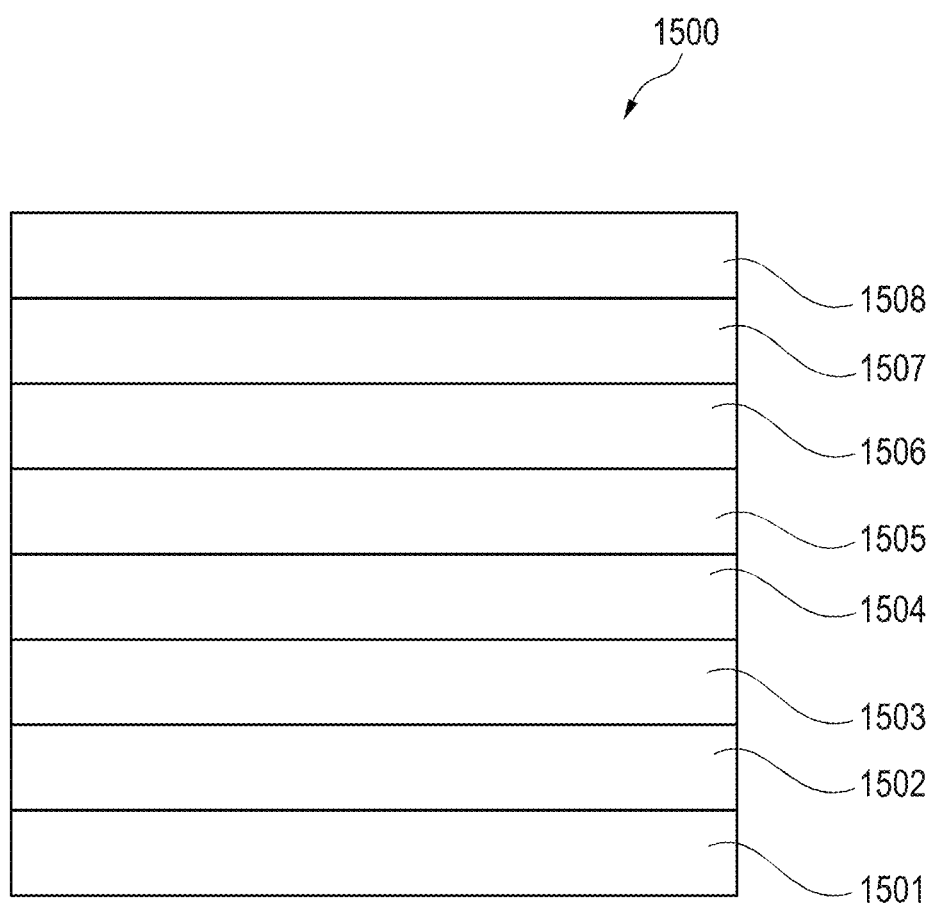
FIG. 15 is an OLED according to a further aspect of the invention.

Referring now to FIG. 15, there is shown an OLED 1500. The OLED 1500 comprises the following successive layers: a substrate 1501, an anode 1502, an optional hole transport layer 1503, an optional electron blocking layer 1504, an emissive layer 1505, an optional hole blocking layer 1506, an optional electron transport layer 1507, and a cathode 1508.

Each layer described above may comprise any suitable material known to those skilled in the art, and may comprise more than one type of material or layer. For example, the substrate 1501 may comprise glass, quartz, polymers, and so on. The thickness is not critical and may be, for example, between 25 to 1000 microns depending on the application of the device. The anode 1502 may comprise any electrically conductive material, e.g. metal, or a conductive metal oxide such as ITO (indium tin oxide). The hole transport layer 1503 may comprise, for example, 1,4-bis[(1-naphthyphenyl)-amino]biphenyl (NPD). The emissive layer 1505 may comprise aluminium tris(8-hydroxyquinoline). The hole blocking layer 1506 may comprise 2,9-dimethyl-4,7-diphenyl-1,10-phenanthroline (bathocuproine, BCP). The electron transport layer 1507 may comprise, for example, metal chelates such as, for example, aluminium tris(8-hydroxyquinoline). The cathode 1508 may comprise any metal, for example, aluminium, lithium, magnesium, and/or calcium.

The emissive layer 1505 comprises the triphenylene derivatives of the present invention, e.g. the triphenylene derivative series 100.

An OLED 1500 may be fabricated in the following manner:

The anode 1502 is patterned upon the clean substrate 1501.

The substrate 1501, which is patterned with the anode 1502, is treated with oxygen for 1 to 5 minutes.

The substrate 1501, which is patterned with the anode 1502, is placed in a thermal evaporator and the pressure is reduced to below $6 \times 10^{-6}$ torr.

The hole transport layer 1503, the electron blocking layer 1504, the emissive layer 1505, the hole blocking layer 1506, the electron transport layer 1507, and the cathode 1508 are successively formed in the listed order by thermal evaporation.

It will be appreciated by those skilled in the art that several variations to the aforementioned embodiments are envisaged without departing from the scope of the invention. For example, the R group of the triphenylene derivative series 100 and Precursors 1 and 2 need not be restricted to $C_5H_{11}$, and may be any stable alkyl or aryl group capable of alkylating the phenol moiety of the triphenylene moiety.

Advantageously, the triphenylene derivative series 100 of the present invention may be further functionalised, for example, by derivatisation of functional groups within the R group. This provides the possibility of using the triphenylene derivative of the present invention as biotags or probes, for example.

It will also be appreciated by those skilled in the art that any number of combinations of the aforementioned features and/or those shown in the appended drawings provide clear advantages over the prior art and are therefore within the scope of the invention described herein.

The invention claimed is:

1. Polycyclic aromatic hydrocarbon derivatives, represented by the following formula:

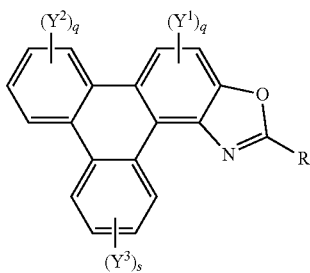

wherein R independently represents an aromatic group and/or an aliphatic group;
p is an integer of 1 to 2;
q and s are independently integers of 1 to 4;
$Y^1$, $Y^2$, and $Y^3$ independently represent a hydrogen atom, a deuterium atom, a fluorine atom, a chlorine atom, a bromine atom, a carbon atom, an alkylated oxygen atom, an alkylated nitrogen atom, a hydroxyl group, a cyano group, a nitro group, an alkyl group and/or an aryl group.

2. Polycyclic aromatic hydrocarbon derivatives, represented by the following formula:

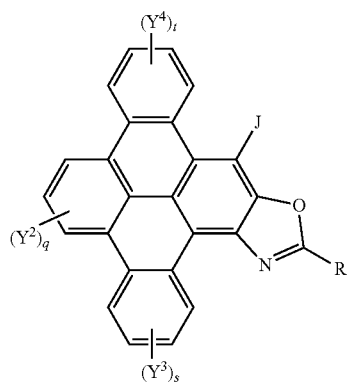

wherein R independently represents an aromatic group and/or an aliphatic group;

q is independently an integer of 1 to 3;
s is independently an integer of 1 to 4;
t is independently an integer of 1 to 4;
$Y^2$, $Y^3$, and $Y^4$ and J independently represent a hydrogen atom, a deuterium atom, a fluorine atom, a chlorine atom, a bromine atom, a carbon atom, an alkylated oxygen atom, an alkylated nitrogen atom, a hydroxyl group, a cyano group, a nitro group, an alkyl group and/or an aryl group.

3. Polycyclic aromatic hydrocarbon derivatives, wherein the polycyclic aromatic hydrocarbon derivatives are triphenylene derivatives represented by the following formula:

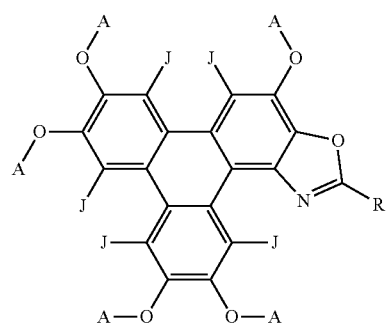

wherein R independently represents an aromatic group and/or an aliphatic group;
A independently represents a hydrogen atom, an aryl group, an alkyl group comprising 1 to 20 carbons or an alkyl ether;
J independently represent a hydrogen atom, a deuterium atom, a fluorine atom, a chlorine atom, a bromine atom, a carbon atom, an alkylated oxygen atom, an alkylated nitrogen atom, a hydroxyl group, a cyano group, a nitro group, an alkyl group and/or an aryl group.

4. Polycyclic aromatic hydrocarbon derivatives, represented by the following formula:

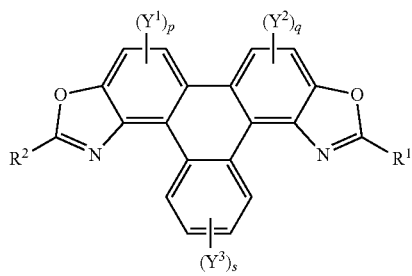

wherein $R^1$ and $R^2$ independently represents an aromatic group and/or an aliphatic group;
p and q are independently an integer of 1 to 2;
s is an integer of 1 to 4;
$Y^1$, $Y^2$, and $Y^3$ independently represent a hydrogen atom, a deuterium atom, a fluorine atom, a chlorine atom, a bromine atom, a carbon atom, an alkylated oxygen atom, an alkylated nitrogen atom, a hydroxyl group, a cyano group, a nitro group, an alkyl group and/or an aryl group.

5. Polycyclic aromatic hydrocarbon derivatives, represented by the following formula:

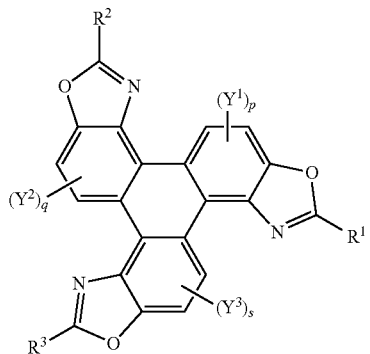

wherein R¹, R², R³ independently represent an aromatic group and/or an aliphatic group;

p, q, and s are each independently an integer of 1 to 2;

Y¹, Y², and Y³ independently represent a hydrogen atom, a deuterium atom, a fluorine atom, a chlorine atom, a bromine atom, a carbon atom, an alkylated oxygen atom, an alkylated nitrogen atom, a hydroxyl group, a cyano group, a nitro group, an alkyl group and/or an aryl group.

6. Polycyclic aromatic hydrocarbon derivatives according to claim 1, wherein R is an alkyl group.

7. Polycyclic aromatic hydrocarbon derivatives according to claim 1, wherein R is an aromatic group.

8. Polycyclic aromatic hydrocarbon derivatives according to claim 7, wherein R is a heterocyclic aromatic group.

9. Polycyclic aromatic hydrocarbon derivatives according to claim 7, wherein R is a polycyclic aromatic hydrocarbon.

10. Polycyclic aromatic hydrocarbon derivatives according to claim 1 selected from the following structures:

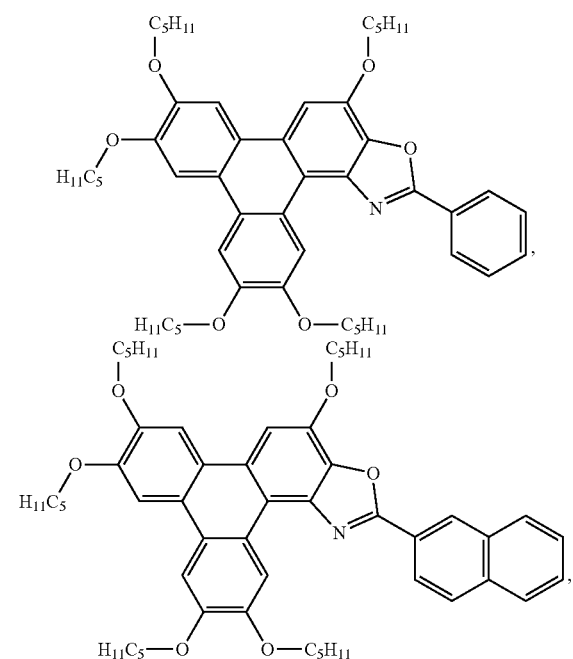

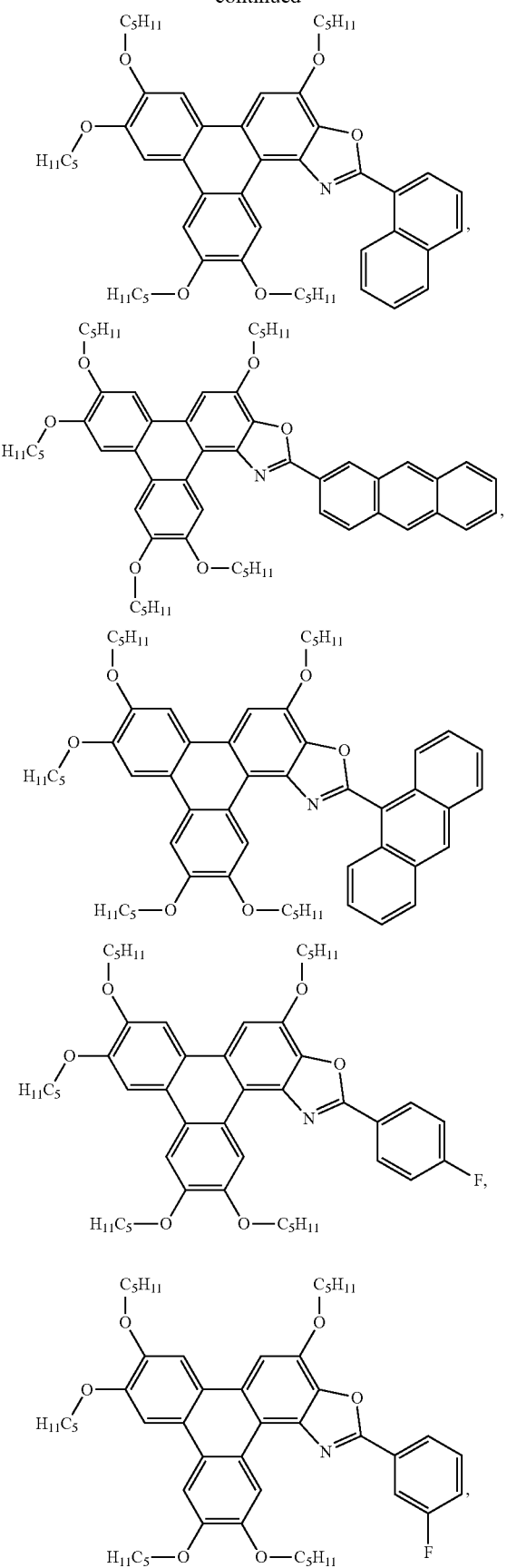

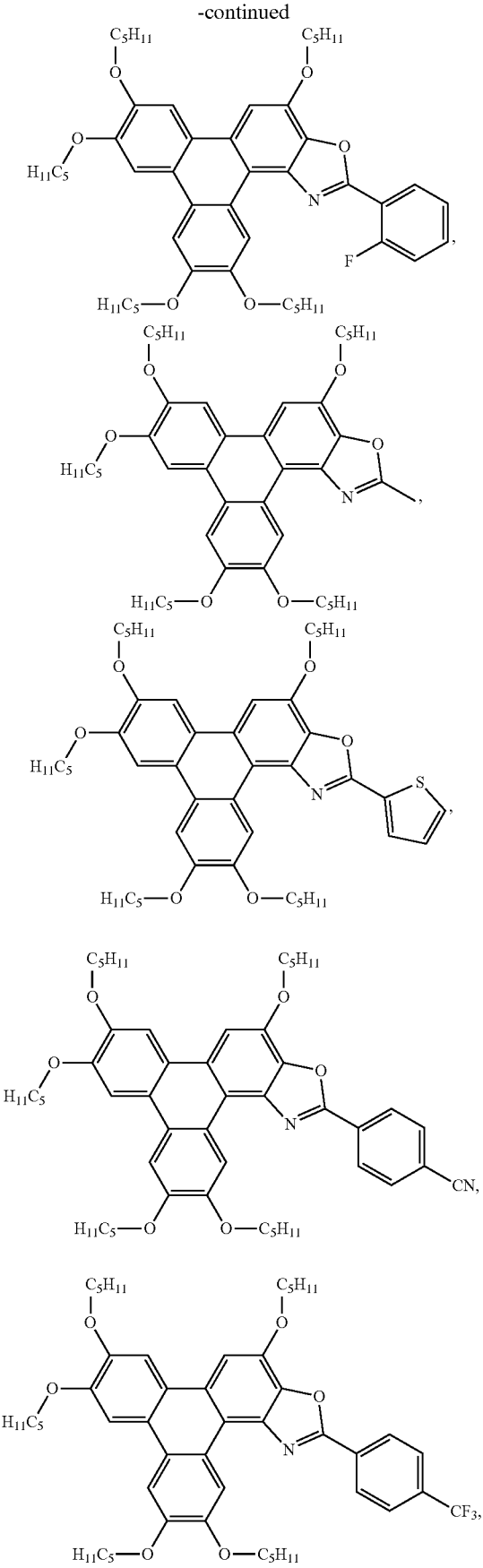
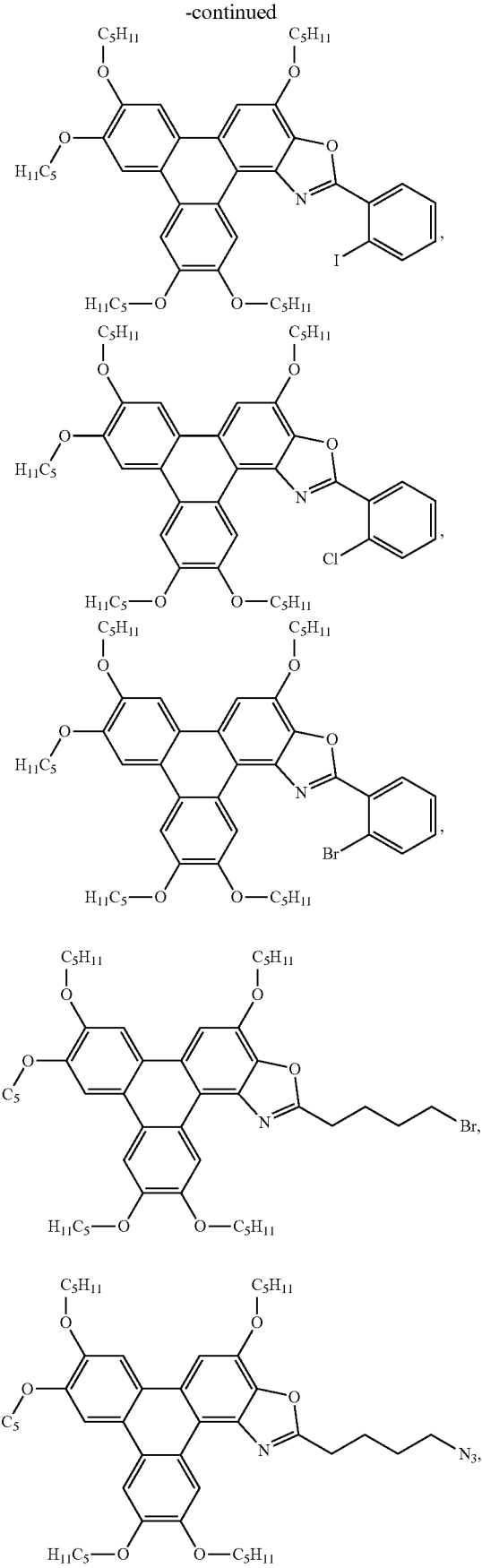

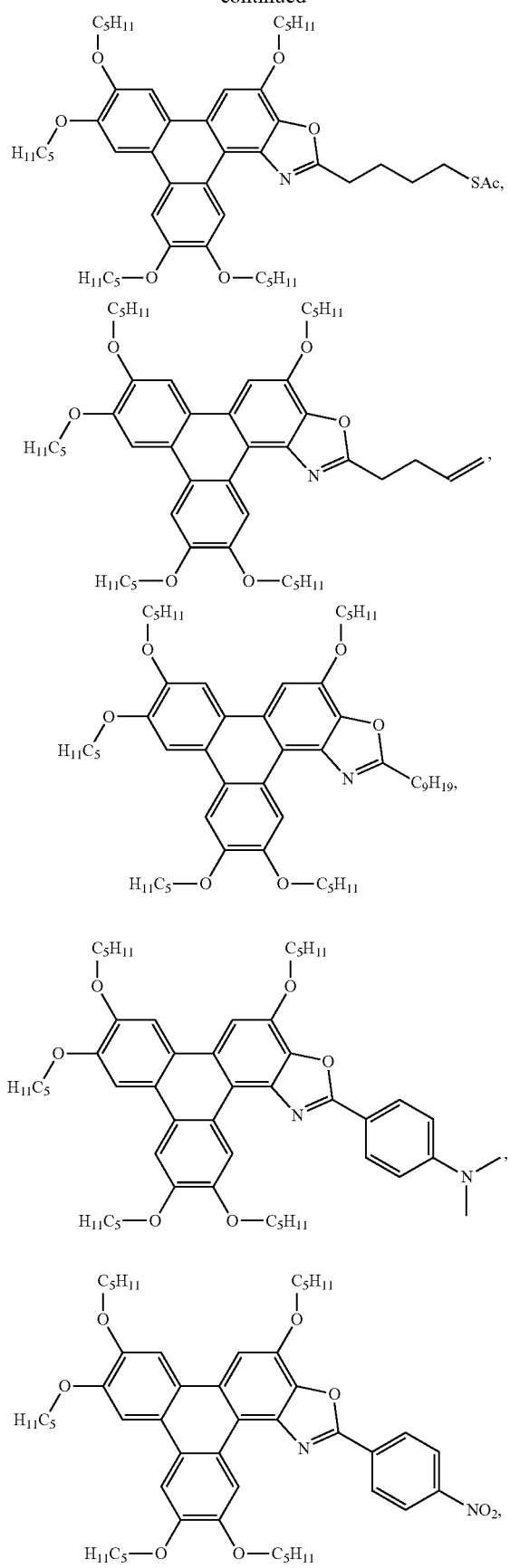
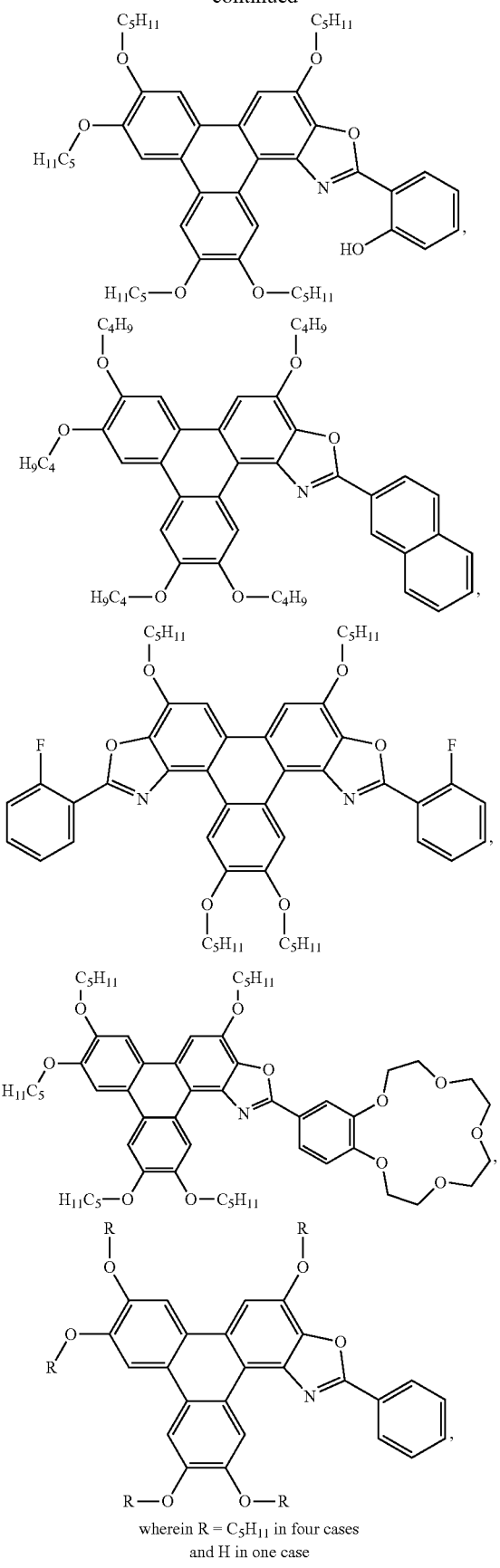
wherein R = C₅H₁₁ in four cases and H in one case

55
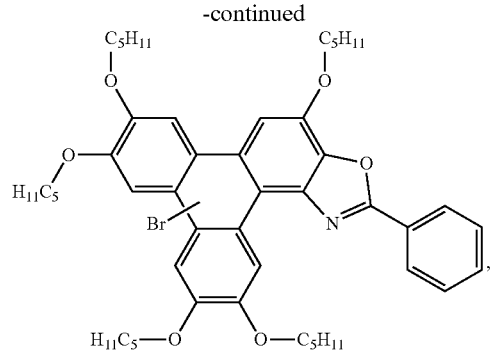
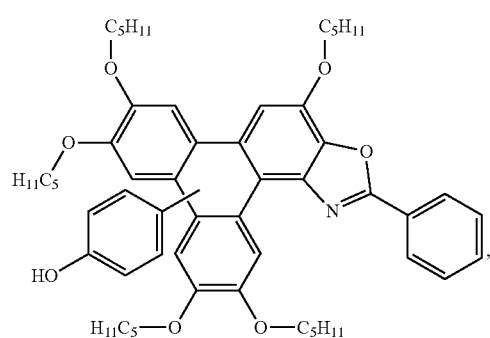
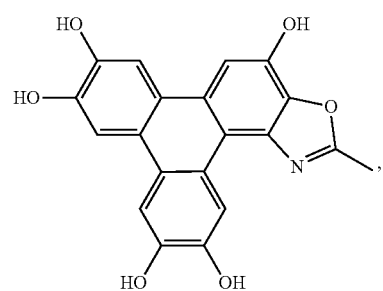
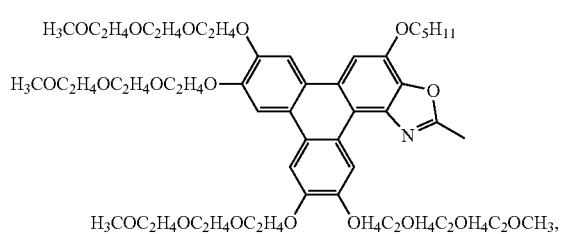
56
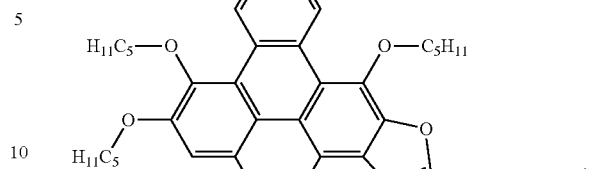
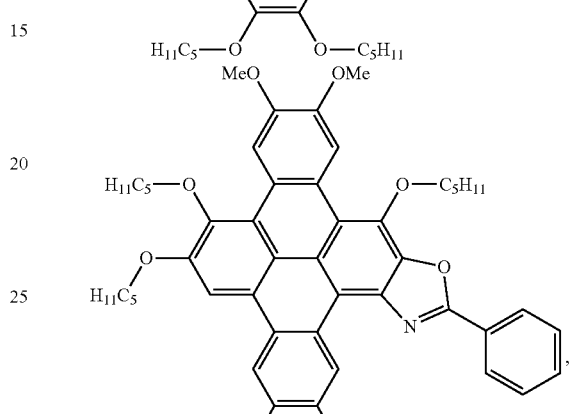
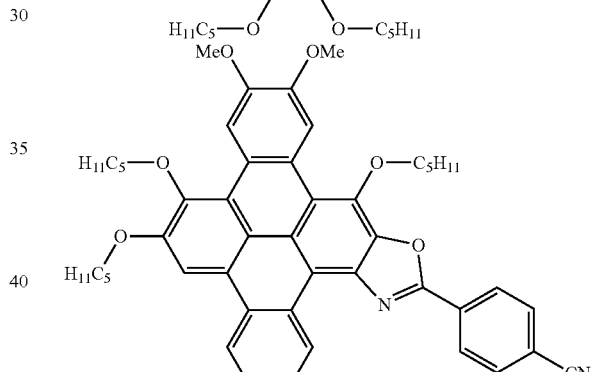
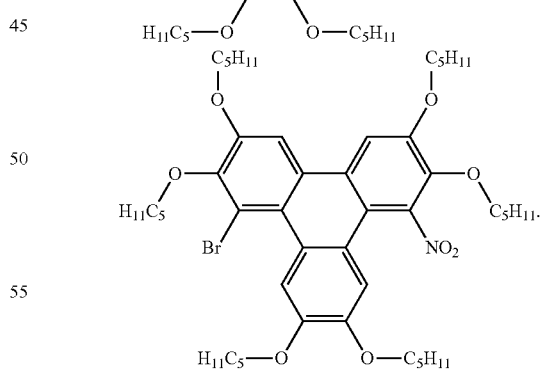
* * * * *